(12) United States Patent
Day et al.

(10) Patent No.: US 9,644,213 B2
(45) Date of Patent: May 9, 2017

(54) METHOD OF ENHANCING PLANT DROUGHT TOLERANCE BY EXPRESSION OF NDR1

(71) Applicant: BOARD OF TRUSTEES OF MICHIGAN STATE UNIVERSITY, East Lansing, MI (US)

(72) Inventors: Brad Day, DeWitt, MI (US); Patricia Santos, Okemos, MI (US); Caleb Knepper, Salinas, CA (US)

(73) Assignee: BOARD OF TRUSTEES OF MICHIGAN STATE UNIVERSITY, East Lansing, MI (US)

( * ) Notice: Subject to any disclaimer, the term of this patent is extended or adjusted under 35 U.S.C. 154(b) by 94 days.

(21) Appl. No.: 14/384,094

(22) PCT Filed: Mar. 8, 2013

(86) PCT No.: PCT/US2013/029898
§ 371 (c)(1),
(2) Date: Sep. 9, 2014

(87) PCT Pub. No.: WO2013/134651
PCT Pub. Date: Sep. 12, 2013

(65) Prior Publication Data
US 2015/0047070 A1    Feb. 12, 2015

Related U.S. Application Data
(60) Provisional application No. 61/608,747, filed on Mar. 9, 2012.

(51) Int. Cl.
*C12N 15/82* (2006.01)
(52) U.S. Cl.
CPC ............. *C12N 15/8273* (2013.01)
(58) Field of Classification Search
None
See application file for complete search history.

(56) References Cited

U.S. PATENT DOCUMENTS

| 6,166,295 A * | 12/2000 | Staskawics | ........ C12N 15/8281 435/410 |
| 2011/0107457 A1* | 5/2011 | Frank | ................. C12N 15/8285 800/279 |

FOREIGN PATENT DOCUMENTS

WO    98/22594 A1    5/1998

OTHER PUBLICATIONS

Knepper et al, Plant Physiology, May 2011, vol. 156, pp. 286-300, cited in the IDS filed Feb. 20, 2015.*
Coppinger et al, The Plant Journal, 2004, vol. 40, pp. 225-237, cited in the IDS filed Sep. 20, 2015.*
Chern et al, Evidence for a disease-resistance pathway in rice similar to the NPR1-mediated signaling pathway in Arabidopsis. Plant J. 27:101-113, 2001.*
International Search Report and Written Opinion received for PCT Patent Application No. PCT/US2013/029898, mailed on May 21, 2013, 13 pages.
Coppinger et al., "Overexpression of the Plasma Membrane-Localized NDR1 Protein Results in Enhanced Bacterial Disease Resistance in *Arabidopsis thaliana*", The Plant Journal, vol. 40, No. 2, Oct. 2004, pp. 225-237.
Hundertmark et al., "The Reduction of Seed-Specific Dehydrins Reduces Seed Longevity in *Arabidopsis thaliana*", Seed Science Research, vol. 21, 2011, pp. 165-173.
Knepper et al., "Arabidopsis NDR1 is an Integrin-Like Protein with a Role in Fluid Loss and Plasma Membrane-Cell Wall Adhesion", Plant Physiology, vol. 156, May 2011, pp. 286-300.
Singh et al., "Solution Structure of a Late Embryogenesis Abundant Protein (LEA14) from *Arabidopsis thaliana*, a Cellular Stress-Related Protein", Protein Science, vol. 14, No. 10, 2005, pp. 2601-2609.
International Preliminary Report on Patentability received for PCT Patent Application No. PCT/US2013/029898, mailed on Sep. 18, 2014, 8 pages.

* cited by examiner

*Primary Examiner* — Eileen B O Hara
(74) *Attorney, Agent, or Firm* — Clark IP Law, PLC

(57) ABSTRACT

A method of producing improved drought tolerance in a plant by introducing into a plant or plant part a vector having a nucleic acid molecule which expresses or increases a polypeptide that confers drought tolerance compared to a plant in which no vector with the nucleic acid is introduced. The polypeptide is a NON-RACE-SPECIFIC DISEASE RESISTANCE 1 (NDR1).

13 Claims, 13 Drawing Sheets
(2 of 13 Drawing Sheet(s) Filed in Color)

```
AGTTATCTTAACTTTCAAGATCGATACTAACCAATTGAATATTGTATTGT
TAACTGTGCAAAATATTTTAGTACGACTTTGCGAGTCAGTTTAGTCTGTT
AAAAATTATTTTGTTTGGGTCATAAAAACTATCTATATCTTTGCATGAAA
CAGCACTACAGTCTACATCAGATTTATAATTTAAAAAGACGCGGTAGTAT
TTTAAAACATTTTGTTTCGTTTATTCATTTATTGTGAAAGTTGACATCGA
TTACATCAAACAATAATCTTTTCTAGATCATTTTCCTAACGAATCTATTC
AGTGAACCATGTGACACAATTTACATTGGTTGGTAGTAATATAAGAATTT
CACATGTGGTATATTATAAATAATTTTAGTTTCACATAATTTTAATCAA
AGAAATTTAATTGATATGTTTAATATTAATAATGTTAAAAATATAAAT
AAATATTAAAGCTTAGAGTTAATAATATTTTAAAC:TTTTACTATAGTTG
ACACTTTTAAAAATCTAATATAAACTATACCTGGTAAAACTAAATAGTTT
AACTAAAAAATGAATCAAACAATATAAGAGATATTCAAAGCAGTTTAACA
ATATCTAGTCTTAGATTTACTCATGCGGATTCCAGAATAATTTGGATACT
AGTTCTCTGTTTCAGTTCAGAGTTATTGCATTTTCATAAATAAAGCGAAT
ATGAATTTAGTTTTATCAATCTAGTAGATTTTCAGTTTTTTATTTATCAA
ACAATTATTTCAGTTTCTTTTTTCAGGTTTTATCAATCTAGTAGATTTTC
AGTTTTTTGTTTATCAAACAATTATTTCAGTTTCTTTTTTCAGTTTATGT
TCGATAACAATGTTTTAGATATACGATAATCAAGTAGTTCGAATTACCTT
GACATTTCTAGATTGAATTTTCCAAACAAAGTTTACATATATATATATAT
ATATATATATAGCGGATTGCTCATTGCCATTGGTTGTGAAATCAAGAATT
AATGTGGATGGTAAGATGTAAACTTCTTACAAAAAGTCTATTTAGGAGAA
CGAAAACGTGTGAAGGTCTTGTTTTCCTAAGGTTTCGTTTGGGTCTCTT
TTATTTTGTACCTTGTAATTCTCTTGGCCCTTTAGCCAACTAAGCACATT
TTGGGATTGAATATATATTTAAAAAAATATATATATATATATATATATTA
AGAAAATTACTTTTGAAATTTGTATTTTGATTAGTGTTGCTAATTATGGT
TTAAGCATGAGAGTCCATCCAATTCGACCCGAGTCCTATATACAGTATGG
TTCAGCAAAAGGGTTTGGGCCTGGCCATAGTTTTTTATGGCAACAAGCTA
TATGAAACCATATATAATAAATACAATTTCGTATTTTGATACAGTCAGTA
TGAGACTAGAAAAACTAGCCACTAGGCCACTGACCAAAAAATAAAATAAG
AAAAAAACTAATCTTTATCTCACCATATTTTAGATCTTTGAAATTCCAA
AAACATAATTAGAGTTTCTCTTTCCTTAGTTTCTTGTGTAGTTTGTATGT
TTCAGTAGGGTTTTTTTCCTTATTTTATGTAAATAAATGGAATAAGATTC
AGTTTTCTGTTATGGGACATCCCTCGTTAATTCTTGTTTTGGTTCTTTTT
GATAACCCAAAGTTTATATAGGTTTTTTTTAATTTATCTTCTTACGTCC
ATTAATTTGTTTTTGTTTTGTTATGTATTTGGCTAAACGCGTGTGTGCGT
GTGTGTCCTACTGAGTCGTCTCTTTTGAGTCAACTTGAAATATCAACCAA
TCAGCAAACCAAAATCTTATAACATCATCTTCTTCATCTTTCCGACAAAA
ATACCAAATTCTTGAAAACAAAAAAAAAATG
                              +1
```

Figure 9

SEQUENCE LISTING

<160> NUMBER OF SEQ ID NOS: 3

<210> SEQ ID NO 1
<211> LENGTH: 219
<212> TYPE: PRT
<213> ORGANISM: Arabidopsis thaliana

<400> SEQUENCE: 1

```
Met Asn Asn Gln Asn Glu Asp Thr Glu Gly Gly Arg Asn Cys Cys Thr
 1               5                  10                  15

Cys Cys Leu Ser Phe Ile Phe Thr Ala Gly Leu Thr Ser Leu Phe Leu
            20                  25                  30

Trp Leu Ser Leu Arg Ala Asp Lys Pro Lys Cys Ser Ile Gln Asn Phe
        35                  40                  45

Phe Ile Pro Ala Leu Gly Lys Asp Pro Asn Ser Arg Asp Asn Thr Thr
    50                  55                  60

Leu Asn Phe Met Val Arg Cys Asp Asn Pro Asn Lys Asp Lys Gly Ile
65                  70                  75                  80

Tyr Tyr Asp Asp Val His Leu Asn Phe Ser Thr Ile Asn Thr Thr Lys
                85                  90                  95

Ile Asn Ser Ser Ala Leu Val Leu Val Gly Asn Tyr Thr Val Pro Lys
            100                 105                 110

Phe Tyr Gln Gly His Lys Lys Ala Lys Lys Trp Gly Gln Val Lys
        115                 120                 125

Pro Leu Asn Asn Gln Thr Val Leu Arg Ala Val Leu Pro Asn Gly Ser
    130                 135                 140

Ala Val Phe Arg Leu Asp Leu Lys Thr Gln Val Arg Phe Lys Ile Val
145                 150                 155                 160

Phe Trp Lys Thr Lys Arg Tyr Gly Val Glu Val Gly Ala Asp Val Glu
                165                 170                 175

Val Asn Gly Asp Gly Val Lys Ala Gln Lys Lys Gly Ile Lys Met Lys
            180                 185                 190

Lys Ser Asp Ser Ser Phe Pro Leu Arg Ser Ser Phe Pro Ile Ser Val
        195                 200                 205

Leu Met Asn Leu Leu Val Phe Phe Ala Ile Arg
    210                 215
```

<210> SEQ ID NO 2
<211> LENGTH: 1728
<212> TYPE: DNA
<213> ORGANISM: Arabidopsis thaliana

<400> SEQUENCE: 2

| | | |
|---|---|---|
| tgaccaaatt cttgaaaaca aaaaaaaaat gaataatcaa atgaagaca cagaaggtgg | 60 |
| tcgaaactgt tgtacttgct gcttaagctt catcttcaca gctggtctca cctctctttt | 120 |
| cttatggctt agtctccgtg cggacaaacc caaatgctca atccaaaact ttttcattcc | 180 |
| tgccctcgga aaagacccaa attcacgaga caataccact ctaaatttca tggttcgttg | 240 |
| tgacaatccg aataaagaca aaggaatcta ctacgacgat gtccacctta atttttccac | 300 |
| catcaacacg accaagatca attcatctgc tcttgtctta gttggtaact acacagtgcc | 360 |
| taagttctat caaggacaca agaagaaggc caagaagtgg ggtcaagtaa agccgctaaa | 420 |
| tgaccaaatt cttgaaaaca aaaaaaaaat gaataatcaa atgaagaca cagaaggtgg | 480 |
| tcgaaactgt tgtacttgct gcttaagctt catcttcaca gctggtctca cctctctttt | 540 |
| cttatggctt agtctccgtg cggacaaacc caaatgctca atccaaaact ttttcattcc | 600 |

```
tgccctcgga aaagacccaa attcacgaga caataccact ctaaatttca tggttcgttg      660
tgacaatccg aataaagaca aaggaatcta ctacgacgat gtccacctta atttttccac      720
catcaacacg accaagatca attcatctgc tcttgtctta gttggtaact acacagtgcc      780
taagttctat caaggacaca agaagaaggc caagaagtgg ggtcaagtaa agccgctaaa      840
tgaccaaatt cttgaaaaca aaaaaaaaat gaataatcaa aatgaagaca cagaaggtgg      900
tcgaaactgt tgtacttgct gcttaagctt catcttcaca gctggtctca cctctctttt      960
cttatggctt agtctccgtg cggacaaacc caaatgctca atccaaaact ttttcattcc     1020
tgccctcgga aaagacccaa attcacgaga caataccact ctaaatttca tggttcgttg     1080
tgacaatccg aataaagaca aaggaatcta ctacgacgat gtccacctta atttttccac     1140
catcaacacg accaagatca attcatctgc tcttgtctta gttggtaact acacagtgcc     1200
taagttctat caaggacaca agaagaaggc caagaagtgg ggtcaagtaa agccgctaaa     1260
caaccagacg ttttacgag cggttttgcc taatggatcg gctgttttca ggttggatct      1320
caagactcaa gttagattca agattgtttt ttggaaaact aagaggtatg gggttgaagt     1380
tggagctgat gttgaagtca acggtgatgg agtaaaagct cagaagaaag gaattaagat     1440
gaagaaatct gattcttctt ttccattaag aagctctttt ccgattagtg ttttgatgaa     1500
tttactcgta ttctttgcta ttcgttaact tcattaatgg tgttgatttt caggtttttc     1560
atttcttggt tttgttgatt tgattattg actattcat gagtttgtt gtgatcctta     1620 gttccatttt cttcattgca taatttatcc cttattttt tgttttaac tatgtattag     1680

tttccatcaa caaattcta tttgaaaatc attttatcca ttttttat                       1728
```

<210> SEQ ID NO 3
<211> LENGTH: 1249
<212> TYPE: DNA
<213> ORGANISM: Arabidopsis thaliana

<400> SEQUENCE: 3

```
agttatctta actttcaaga tcgatactaa ccaattgaat attgtattgt taactgtgca       60
aaatatttta gtacgacttt gcgagtcagt ttagtctgtt aaaaattatt ttgtttgggt      120
cataaaaact atctatatct ttgcatgaaa cagcactaca gtctacatca gatttataat      180 ttaaaagac gcggtagtat tttaaaacat tttgtttcgt ttattcattt attgtgaaag       240
ttgacatcga ttacatcaaa caataatctt ttctagatca ttttcctaac gaatctattc      300
agtgaaccat gtgacacaat ttacattggt tggtagtaat ataagaattt cacatgtggt      360
atattataaa ataattttag tttcacataa ttttaatcaa agaaatttaa tttgatatgt      420
ttaatattaa taatgttaaa aatataaaat aaatattaaa gcttagagtt aataatattt      480
taaactttta ctatagttga cacttttaaa aatctaatat aaactatacc tggtaaaact      540
aaatagttta actaaaaaat gaatcaaaca atataagaga tattcaaagc agtttaacaa      600
tatctagtct tagatttact catgcggatt ccagaataat ttggatacta gttctctgtt      660
tcagttcaga gttattgcat tttcataaat aaagcgaata tgaatttagt tttatcaatc      720
tagtagattt tcagtttttt attatcaaa саататттс аgтттсттт ттсаggттт        780

atcaatctag tagatttca gttttttgtt tatcaaacaa ttatttcagt ttcttttttc     840

agttatgtt cgataacaat gttttagata tacgataatc aagtagttcg aattaccttg      900

асатттста атт gaattttt ccaaacaaag tttacatata tatatatata tatatata    960
```

-continued

```
gcggattgct cattgccatt ggttgtgaaa tcaagaatta atgtggatgg taagatgtaa    1020
acttcttaca aaaagtctat ttaggagaac gaaaacgtgt gaaggtcttg ttttcctaag    1080
gtttcgtttt gggtctcttt tattttgtac cttgtaattc tcttggccct ttagccaact    1140
aagcacattt tgggattgaa tatatattta aaaaaatata tatatatata tatatattaa    1200
gaaaattact tttgaaattt gtattttgat tagtgttgct aattatggt               1249
```

METHOD OF ENHANCING PLANT DROUGHT TOLERANCE BY EXPRESSION OF NDR1

RELATED APPLICATIONS

This application is a U.S. National Stage Filing under 35 U.S.C. 371 from International Application No. PCT/US2013/029898, having an International Filing Date of Mar. 8, 2013 and published in English as WO2013/134651 on Sep. 12, 2013, which application claims the benefit under 35 U.S.C. 119 (e) of U.S. Provisional Application Ser. No. 61/608,747 filed on Mar. 9, 2012, which applications and publications are hereby incorporated by reference herein in their entireties.

STATEMENT OF GOVERNMENT RIGHTS

This invention was made with government support under IOS0641319 and IOS1146128 awarded by the National Science Foundation The government has certain rights in the invention.

BACKGROUND

Drought or water deficiency adversely affects plant health and this is a problem for economically important plants. Means to improve plant tolerance to drought have included selecting or cross breeding, identifying and controlling expression of genes critical to drought tolerance.

SUMMARY

Disclosed is the NON-RACE SPECIFIC DISEASE RESISTANCE1 (NDR1) gene and protein that is shown to confer drought tolerance and may be used to increase drought tolerance in plants.

In one embodiment, the NON-RACE-SPECIFIC DISEASE RESISTANCE1 (NDR1) polypeptide and those polypeptides have at least 80% homology, and nucleic acid molecules encoding NDR1 are used to provide drought tolerance in plants. Fragments of the polypeptide which increase drought tolerance may be used in the disclosed methods.

Another embodiment provides a method of producing a plant having drought tolerance, the method comprising
a) introducing into at least one plant or plant part a vector comprising a nucleic acid molecule which expresses or increases a polypeptide that confers drought tolerance, the polypeptide selected from the group consisting of,
  i) a nucleotide sequence of SEQ ID NO: 2 or variants thereof;
  ii) a nucleotide sequence that encodes a polypeptide comprising the amino acid sequence of SEQ ID NO: 1;
  iii) a polypeptide encoding a NON-RACE-SPECIFIC DISEASE RESISTANCE1 (NDR1);
  ii) a sequence having at least 80% identity to the amino acid sequence of SEQ ID NO: 1, and
  iii) a functional fragment of SEQ ID NO: 1;
b) selecting at least one plant or plant part having improved drought tolerance from a plurality of plants or plant parts into which the vector has been introduced compared to a plant in which no vector has been introduced.

BRIEF DESCRIPTION OF DRAWINGS

The patent or application file contains at least one drawing executed in color. Copies of this patent or patent application publication with color drawing(s) will be provided by the Office upon request and payment of the necessary fee.

FIG. 9 shows the promoter sequence of the NDR1 gene (SEQ ID NO: 3). The TATA box is bold, the CAAT box in italics and the transcription start site indicated by underlining

DETAILED DESCRIPTION

Figure 1:
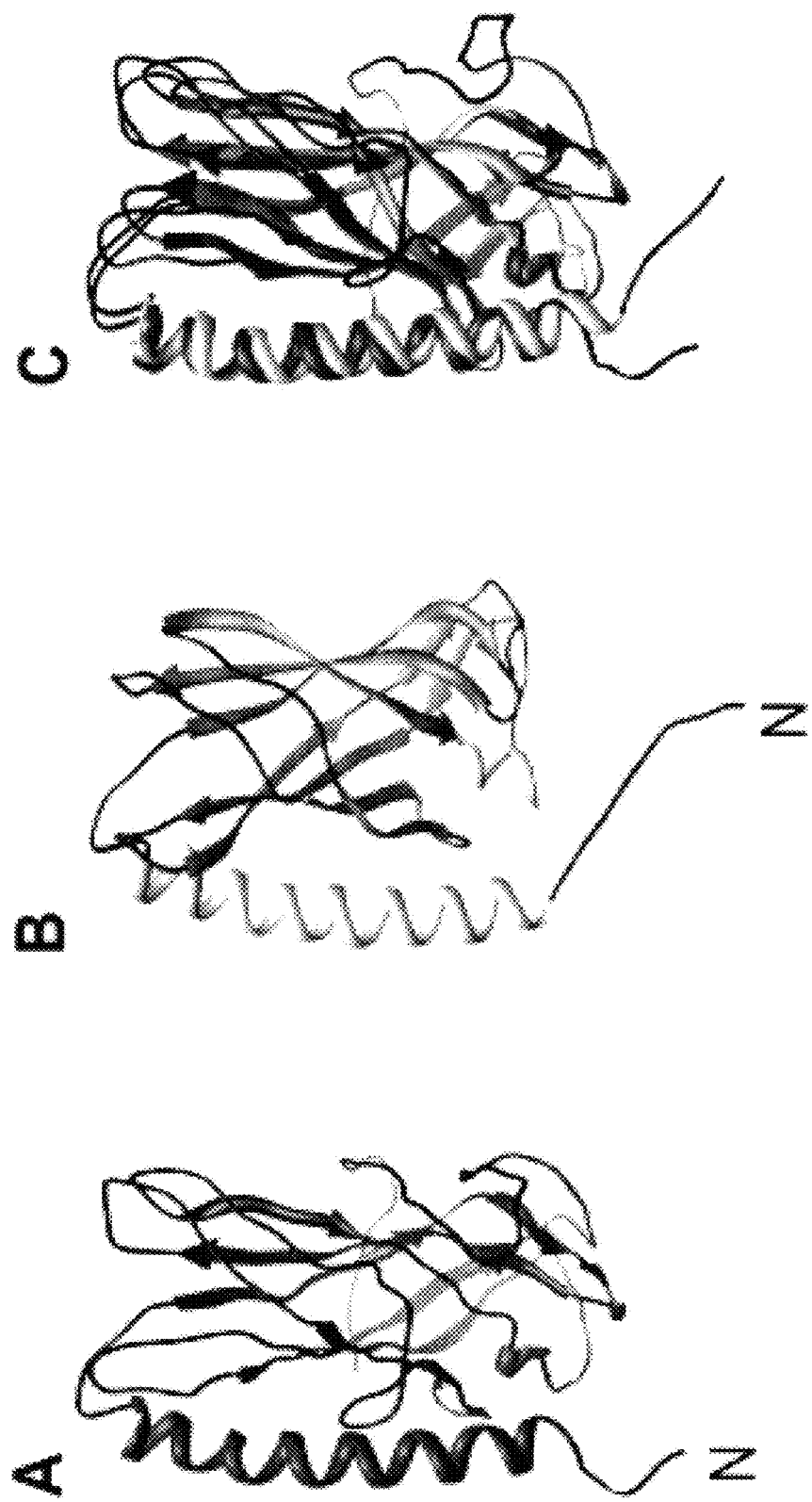
FIGS. 1A-1C are drawings showing homology modeling of NDR1 with the integrin-like late embryogenesis protein, LEA14. (A) Predicted structure of NDR1. (B) The solved structure of LEA14 (pdb_1yyc; Singh et al., 2005). (C) NDR1 predicted structure threaded onto the solved structure of LEA14 highlighting the predicted structural homology. 'N' denotes amino-terminal.

The NON-RACE-SPECIFIC DISEASE RESISTANCE1 (NDR1) polypeptide when expressed in plants can increase plant tolerance to drought compared to a plant not expressing or expressing at lower levels NDR1. In one embodiment, the polypeptide is that shown at GenBank Accession No. AT3G20600, shown here as SEQ ID NO: 1. In another embodiment the polypeptide is a fragment of the NDR1 polypeptide wherein the fragment provides improved plant drought tolerance. In another embodiment, expression of a polypeptide having at least 80%, 85%, 90% or 95% homology to the NRD1 polypeptide is expressed in a plant to increase drought tolerance. Further embodiments provide that a nucleic acid molecule encoding NDR1, or which encode a polypeptide having at least 95% homology to NDR1 or fragments thereof which, when expressed, provide improved drought tolerance are introduced into a plant such that the polypeptide is expressed. The nucleic acid molecule may be obtained by any convenient method, whether isolated from a plant or synthetically produced, for example.

The NDR1 protein shows 31% identity to LEA14 (GenBank Acc. No. AT1G01470) and 95% homology to the LEA14 protein. Analysis of the NDR1 gene and protein showed the presence of an RGD motif.

The promoter of NDR1 was also isolated (SEQ ID NO:3 and FIG. 9). In an embodiment, the disclosed promoter may be used to drive the NDR1 gene or fragments, or may be used to drive expression of a different operably linked nucleic acid molecule. Analysis of the NDR1 promoter showed the presence of ABRE and LTRE cis-acting regulatory elements.

NDR1 is a plasma membrane-localized protein that may undergo multiple posttranslational modifications, including C-terminal processing (e.g. glycosylphosphatidylinositol anchoring) and N-linked glycosylation. Unlike most glycosylphosphatidylinositol-anchored proteins, NDR1 appears to be anchored at the C terminus, which terminus may be resistant to cleavage by phospholipase C and therefore possibly positions NDR1 within the plasma membrane as a "double anchored" protein.

Drought stress is stress resulting from exposure to less than optimal moisture conditions or fluid loss. Fluid loss in a plant can result from any condition that causes the plant to lose fluid, such as increased saline conditions, wounding, heating, infection and the like. NDR1 has been shown to be able to regulate fluid loss in plant cells. When NDR1 expression is effected, the mutant plant may not respond to water loss or conditions that otherwise may trigger stomata to react (viz., the stomata do not close, remaining open). Seed also may not recover from low moisture conditions.

Improved drought tolerance can be determined by any convenient method, including any of a variety of plant health measurements or any improvement in adverse impact on plants caused by drought. By way of example, increased drought tolerance may include increased survival rates, plant growth rate, plant length, weight, leaf area, flower fertility, pollen fertility, seed weight or yield, seed germination or any combination of these, as compared to a plant not expressing or expressing at lower levels the NDR1 polypeptide. Improvement in fluid loss can be measured by transpiration rates, change in stomata and stomatal efficiency. In an example, a plant expressing NDR1 may be compared to an isoline not expressing NDR1, or expressing NDR1 at lower levels.

The NDR1 polypeptide levels may be increased by NDR1 polypeptide expression or overexpression. Where the plant lacks NDR1, a nucleic acid molecule may be introduced which expresses the polypeptide and in other embodiments expression of the NDR1 polypeptide may be increased. The term "over-expression" refers to the expression of a nucleic acid encoding a polypeptide (e.g., a gene) in a transformed plant cell at higher levels (therefore producing an increased amount of the polypeptide encoded by the gene) than the "wild type" plant cell (e.g., a substantially similar cell that is not transfected with the gene) under substantially similar conditions. As used herein, the terms "increasing", "increased expression" or the like are considered relative terms, viz. in comparison with the wild-type or unaltered state. Thus, to over-express or increase expression of a NDR1 nucleic acid refers to increasing or inducing the production of the NDR1 polypeptide encoded by the nucleic acid, which may be done by a variety of approaches, such as increasing the number of genes encoding for the polypeptide, increasing the transcription of the gene (such as by placing the gene under the control of a stronger driving or constitutive promoter), or increasing the transcription or translation of the gene, use of enhancers, splicing introns, use of small RNAs (see, for example U.S. Publication 2012/0036594), selecting a plant having high expression and further cultivation and selection, introducing or impacting another nucleic acid molecule or polypeptide that impacts NDR1 expression, or a combination of these or other approaches. Expression levels can be measured by observing drought tolerance or by quantifying expression by any of the known methods, such as RT-PCR, for example. For example, in the ndr1 mutant it has been identified that specific induction of mRNA expression of genes associated with drought perception and abscisic acid metabolism, demonstrating that the ndr1 mutant may be compromised in regulating drought tolerance.

Expression of NDR1 polypeptide may be controlled by any of a variety of methods. Means of increasing or inhibiting a protein are well known to one skilled in the art and, by way of example, may include, antisense suppression, transgenic expression, use of hairpin formations, co-suppression methods including but not limited to RNA interference, gene activation or suppression using transcription factors or repressors, mutagenesis including transposon tagging, directed and site-specific mutagenesis, chromosome engineering, homologous recombination or the like. In the case of use with homologous recombination, no in vivo construct will be required. Examples of such systems available include use of the Mu transposon, Chandler et al. (1994) The Maize Handbook Ch. 118 Springer-Verlag; RNA interference (U.S. Pat. No. 5,034,323); use of hairpins, (Smith et al. (2000) Nature 407:319-320) and ribozymes (Steinecke et al. (1992) EMBOL J. 11: 15); and zinc-finger targeted molecules (WO 01/52620). By "antisense DNA nucleotide sequence" is intended a sequence that is in inverse orientation to the 5'-to-3' normal orientation of that nucleotide sequence. When delivered into a plant cell, expression of the antisense DNA sequence prevents normal expression of the DNA nucleotide sequence for the targeted gene. See, for example, U.S. Pat. Nos. 5,107,065 and 6,617,496 and Stone, et al. (1999) "A breakdown of Brassica self-incompatibility in ARC 1 antisense transgenic plants" Science 286:1729-1731. Such antisense nucleic acid molecules have been widely used and are adapted to the particular system used and the nucleic acid molecule to which it is targeted. In one example, the antisense nucleotide sequence encodes an RNA transcript that is complementary to and capable of hybridizing with the endogenous messenger RNA (mRNA) produced by transcription of the plant nucleotide sequence that disrupts function or formation of a plant cell or targeted gene. Such an antisense DNA can be transcribed into an RNA sequence capable of binding to the coding or noncoding portion(s) of the target RNA, so as to neutralize the translation of the target RNA. Such antisense genes can be antisense to a gene, for example, which otherwise disrupts function or formation of a plant cell or targeted gene.

The polynucleotide for use in antisense suppression may correspond to all or part of the complement of the sequence encoding the target polypeptide, all or part of the complement of the 5' or 3' untranslated region of the target polypeptide transcript, or all or part of the complement of both the coding sequence and the untranslated regions of a transcript encoding the target polypeptide. In addition, the antisense polynucleotide may be fully complementary (e.g., 100% identical to the complement of the target sequence) or partially complementary (e.g., less than 100% identical to the complement of the target sequence) to the target sequence. Antisense suppression may be used to inhibit the expression of multiple proteins in the same plant. Furthermore, portions of the antisense nucleotides may be used to disrupt the expression of the target gene. Generally, sequences of at least 20 nucleotide, 50 nucleotides, 100 nucleotides, 200 nucleotides, 300, 500, 550, 500, 550, or greater may be used or any amount in-between.

Co-suppression is another phenomena that may be used, where a sequence that is substantially homologous to the corresponding transcript of the target nucleic acid molecule may be provided and may suppress expression of the target nucleic acid molecule. See, for example, Jorgensen et al., Genetic engineering of novel plant phenotypes, U.S. Pat. No. 5,034,323.

In another example, inhibition of the expression of a target polypeptide may be obtained by double-stranded RNA (dsRNA) interference. For dsRNA interference, a sense RNA molecule like that described above for co-suppression and an antisense RNA molecule that is fully or partially complementary to the sense RNA molecule are expressed in the same cell, resulting in inhibition of the corresponding endogenous messenger RNA expression.

Expression of the sense and antisense molecules can be accomplished by designing the expression cassette to include both a sense sequence and an antisense sequence. Alternatively, separate expression cassettes may be used for the sense and antisense sequences. Multiple plant lines transformed with the dsRNA interference expression cassette or expression cassettes are then screened to identify plant lines that show the greatest inhibition of polypeptide expression.

In some embodiments, inhibition of one or more target polypeptide expressions may be obtained by hairpin RNA (hpRNA) interference or intron-containing hairpin RNA (ihpRNA) interference. These methods are considered efficient at inhibiting the gene expression. See, Waterhouse and Helliwell (2003) Nat. Rev. Genet. 4:29-38 and the references cited therein.

For hpRNA interference, the expression cassette is designed to express an RNA molecule that hybridizes with itself to form a hairpin structure that includes a single-stranded loop region and a base-paired stem. The base-paired stem region includes a sense sequence corresponding to all or part of the endogenous messenger RNA encoding the gene whose expression is to be inhibited, and an antisense sequence that is fully or partially complementary to the sense sequence. Thus, the base-paired stem region of the molecule generally determines the specificity of the RNA interference. hpRNA molecules are considered efficient at inhibiting gene expression, and the RNA interference they induce may be inherited by subsequent plant generations. See, for example, Chuang and Meyerowitz (2000) Proc. Natl. Acad. Sci. USA 97:5985-5990; Stoutjesdijk et al. (2002) Plant Physiol. 129:1723-1731; and Waterhouse and Helliwell (2003) Nat. Rev. Genet. 5:29-38. Methods for using hpRNA interference to inhibit or silence the expression of genes are described, for example, in Chuang and Meyerowitz (2000) Proc. Natl. Acad. Sci. USA 97:5985-5990; Stoutjesdijk et al. (2002) Plant Physiol. 129:1723-1731; Waterhouse and Helliwell (2003) Nat. Rev. Genet. 5:29-38; Pandolfini et al. BMC Biotechnology 3:7, and U.S. Patent Publication No. 20030175965. Hairpin RNAs having the ability to suppress gene expression have been described (see, e.g., Matzke et al. (2001) Curr. Opin. Genet. Devel. 11:221-227; Scheid et al. (2002) Proc. Natl. Acad. Sci., USA 99:13659-13662; Waterhouse and Helliwell (2003); Aufsaftz et al (2002) Proc. Nat'l. Acad. Sci. 99(4):16499-16506; and Sijen et al., Curr. Biol. (2001) 11:436-440). A transient assay for the efficiency of hpRNA constructs to silence gene expression in vivo has been described by Panstruga et al. (2003) Mol. Biol. Rep. 30:135-150.

For ihpRNA, the interfering molecules have the same general structure as for hpRNA, but the RNA molecule additionally includes an intron that is capable of being spliced in the cell in which the ihpRNA is expressed. The use of an intron minimizes the loop size in the hairpin RNA molecule following splicing, and this increases the interference efficiency. See, for example, Smith et al. (2000) Nature 507:319-320.

In some methods, inhibition of one or more target polypeptides may be obtained by RNA interference or by gene expression encoding a micro RNA (miRNA). miRNAs are regulatory agents consisting of about 22 ribonucleotides. miRNA are considered efficient at inhibiting endogenous gene expression. See, for example Javier et al. (2003) Nature 525: 257-263.

For miRNA interference, the expression cassette is designed to express an RNA molecule that is modeled on an endogenous miRNA gene. The miRNA gene encodes an RNA that forms a hairpin structure containing a 22-nucleotide sequence that is complementary to another endogenous gene (target sequence). For suppression of target polypeptide expression, the 22-nucleotide sequence is selected from a target transcript sequence and contains 22 nucleotides of said target polypeptide sequence in sense orientation and 21 nucleotides of a corresponding antisense sequence that is complementary to the sense sequence. miRNA molecules are highly efficient at inhibiting the expression of endogenous genes, and the RNA interference they induce is inherited by subsequent generations of plants.

In a still further example, a polynucleotide encodes a zinc finger protein that binds to a gene encoding a target polypeptide, resulting in reduced expression of the gene. In particular examples, the zinc finger protein binds to a regulatory region of a target polypeptide gene. In other examples, the zinc finger protein binds to a messenger RNA encoding a target polypeptide and prevents its translation. Methods of selecting sites for targeting by zinc finger proteins have been described, for example, in U.S. Pat. No. 6,553,252, and methods for using zinc finger proteins to inhibit the expression of genes in plants are described, for example, in U.S. Pat. No. 7,151,201.

As used herein, the terms "nucleic acid" or "polynucleotide" refer to deoxyribonucleotides or ribonucleotides and polymers thereof in either single-or double-stranded form. As such, the terms include RNA and DNA, which can be a gene or a portion thereof, a cDNA, a synthetic polydeoxyribonucleic acid sequence, or the like, and can be single-stranded or double-stranded, as well as a DNA/RNA hybrid. Furthermore, the terms are used herein to include naturally-occurring nucleic acid molecules, which can be isolated from a cell, as well as synthetic molecules, which can be prepared, for example, by methods of chemical synthesis or by enzymatic methods such as by the polymerase chain reaction (PCR). Unless specifically limited, the terms encompass nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g. degenerate codon substitutions) and complementary sequences as well as the sequence explicitly indicated. Specifically, degenerate codon substitutions may be achieved by generating sequences in which the third position of one or more selected (or all) codons is substituted with mixed-base or deoxyinosine residues (Batzer et al. (1991) Nucleic Acid Res. 19:5081; Ohtsuka et al. (1985) J. Biol. Chem. 260:2605-2608; Rossolini et al. (1994) Mol. Cell. Probes 8:91-98). The term "nucleic acid" is used interchangeably with gene, cDNA, and mRNA encoded by a gene.

"Conservatively modified variants" applies to both amino acid and nucleic acid sequences. With respect to particular nucleic acid sequences, "conservatively modified variants" refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given polypeptide. For instance, the codons CGU, CGC, CGA, CGG, AGA, and AGG all encode the amino acid arginine. Thus, at every position where an arginine is specified by a codon, the codon can be altered to any of the corresponding codons described without altering the encoded polypeptide. Such nucleic acid variations are "silent substitutions" or "silent variations," which are one species of "conservatively modified variations." Every polynucleotide sequence described herein which encodes a polypeptide also describes every possible silent variation, except where otherwise noted. Thus, silent substitutions are an implied feature of every nucleic acid sequence which encodes an amino acid. One of skill will recognize that each codon in a nucleic acid (except AUG, which is ordinarily the only codon for methionine) can be modified to yield a functionally identical molecule by standard techniques. In some embodiments, the nucleotide sequences that encode a protective polypeptide are preferably optimized for expression in a particular host cell (e.g., yeast, mammalian, plant, fungal, and the like) used to produce the polypeptide or RNA.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" referred to herein as a "variant" where the alteration results in the substitution of an amino acid with a chemically similar amino acid. Conservative substitution tables providing functionally similar amino acids are well known in the art. See, for example, Davis et al., Basic Methods in Molecular Biology Appleton & Lange, Norwalk, Conn. (1994). Such conservatively modified variants are in addition to and do not exclude polymorphic variants, interspecies homologs, and alleles.

The disclosed nucleic acid molecules and polypeptides can be used to isolate corresponding sequences from other organisms, particularly other plants, or to synthesize synthetic sequences. In this manner, methods such as polymerase chain reaction (PCR), hybridization, synthetic gene construction and the like can be used to identify or generate such sequences based on their sequence homology to the sequences set forth herein. Sequences identified, isolated or constructed based on their sequence identity to the whole of or any portion of the NDR1 sequences or promoter sequences set forth is encompassed here. Synthesis of sequences can be affected by means of mutually priming long oligonucleotides. See for example, Wosnick et al. (1987) Gene 60:115. In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed (See e.g., Sambrook, J., Fritsch, E. F. and Maniatis, T. (1989) Molecular Cloning: A Laboratory Manual, 2nd Edition. Cold Spring Harbor Laboratory Press, Plainview, N. Y; Innis, M., Gelfand, D. and Sninsky, J. (1995) PCR Strategies. Academic Press, New York; Innis, M., Gelfand, D. and Sninsky, J. (1999) PCR Applications: Protocols for Functional Genomics, Academic Press, New York. Moreover, current techniques which employ the PCR reaction permit the synthesis of genes as large as 1.8 kilobases in length. See Adang et al. (1993 Plant Molec. Biol. 21:1131) and Bambot et al. (1993) PCR Methods and Applications 2:266. Known methods of PCR include, but are not limited to, methods using paired primers, nested primers, degenerate primers, gene-specific primers, vector-specific primers, partially-mismatched primers, and the like. In addition, genes can readily be synthesized by conventional automated techniques.

In hybridization techniques, all or part of a known nucleotide sequence is used as a probe that selectively hybridizes to other corresponding nucleotide sequences present in a population of cloned genomic DNA fragments or cDNA fragments (e.g., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the disclosed DNA sequences. Methods for probe preparation for hybridization and for construction of cDNA and genomic libraries are generally known in the art and are disclosed (e.g., Sambrook et al., 1989).

For example, the nucleic acid sequence disclosed herein, or one or more portions thereof, may be used as a probe capable of specifically hybridizing to corresponding sequences. To achieve specific hybridization under a variety of conditions, such probes include sequences that are unique among the sequences to be screened and are preferably at least about 10 nucleotides in length, and most preferably at least about 20 nucleotides in length. Such sequences may alternatively be used to amplify corresponding sequences from a chosen plant by PCR. This technique may be used to isolate sequences from a desired plant or as a diagnostic assay to determine the presence of sequences in a plant. Hybridization techniques include hybridization screening of DNA libraries plated as either plaques or colonies (Sambrook et al., 1989). Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about or 1.0 M Na ion, typically about 0.01 to 1 M Na ion concentration (or other salts) at pH 7 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 50° C. Exemplary high stringency conditions include hybridization in 50% formamide, 1 M NaCl, 0.1% SDS at 37° C., and a wash in 0.1×SSC at 60 to 65° C.

In general, sequences that correspond to the disclosed nucleotide sequences and hybridize to the nucleotide sequence disclosed herein will be at least 50% homologous, 70% homologous, and even 85%, 86%, 87%, 88%, 89%, 90%, 91%, 92%, 93%, 94%, 95%, 96%, 97%, 98%, 99% homologous or more with the disclosed sequence. That is, the sequence similarity between probe and target may range at least or about 50% to about 99% sequence similarity including any range or value therebetween.

Specificity is typically the function of post-hybridization washes, the critical factors being the ionic strength and temperature of the final wash solution. For DNA-DNA hybrids, the Tm can be approximated from the equation of Meinkoth and Wahl, Anal. Biochem., 138:267-284 (1984): $Tm=81.5° C.+16.6 (\log M)+0.41 (\% GC)-0.61 (\% form)-500/L$; where M is the molarity of monovalent cations, % GC is the percentage of guanosine and cytosine nucleotides in the DNA, % form is the percentage of formamide in the hybridization solution, and L is the length of the hybrid in base pairs. The Tm is the temperature (under defined ionic strength and pH) at which 50% of the complementary target sequence hybridizes to a perfectly matched probe. Tm is reduced by about 1° C. for each 1% of mismatching; thus, Tm, hybridization or wash conditions can be adjusted to hybridize to sequences of the desired identity. For example, if sequences with ≥90% identity are sought, the Tm can be decreased 10° C. Generally, stringent conditions are selected to be or about 5° C. lower than the thermal melting point (Tm) for the specific sequence and its complement at a defined ionic strength and pH. However, severely stringent conditions can utilize a hybridization or wash at 1, 2, 3, or 4° C. lower than the thermal melting point (Tm); moderately stringent conditions can utilize a hybridization or wash at 6, 7, 8, 9, or 10° C. lower than the thermal melting point (Tm); low stringency conditions can utilize a hybridization or wash at 11, 12, 13, 14, 15, or 20° C. lower than the thermal melting point (Tm). Using the equation, hybridization and wash compositions, and desired Tm, those of ordinary skill will understand that variations in the stringency of hybridization or wash solutions are inherently described. If the desired degree of mismatching results in a Tm of less than 45° C. (aqueous solution) or 32° C. (formamide solution) it is preferred to increase the SSC concentration so that a higher temperature can be used. An extensive guide to the hybridization of nucleic acids is found in Tijssen (1993) Laboratory Techniques in Biochemistry and Molecular Biology "Hybridization with Nucleic Acid Probes" Part I, Chapter 2 (Elsevier, New York); and Ausubel et al., eds. (1995) Current Protocols in Molecular Biology, Chapter 2 (Greene Publishing and Wiley-Interscience, New York). See Sambrook et al. (1989) Molecular Cloning: A Laboratory Manual (2d ed., Cold Spring Harbor Laboratory Press, Plainview, N.Y.) and Haymes et al. (1985) In: Nucleic Acid Hybridization, a Practical Approach, IRL Press, Washington, D.C.

Included herein are the isolated sequences that have drought tolerance activity and which hybridize under stringent conditions to the sequences disclosed herein, or to fragments thereof.

The following terms are used to describe the sequence relationships between two or more nucleic acids or polynucleotides: (a) "reference sequence", (b) "comparison window", (c) "sequence identity" and (d) "percentage of sequence identity."

(a) As used herein, "reference sequence" is a defined sequence used as a basis for sequence comparison. A reference sequence may be a subset or the entirety of a specified sequence; for example, as a segment of a full-length promoter sequence, or the complete promoter sequence.

(b) As used herein, "comparison window" makes reference to a contiguous and specified segment of a polynucleotide sequence, wherein the polynucleotide sequence in the comparison window may include additions or deletions (e.g., gaps) compared to the reference sequence (which does not include additions or deletions) for optimal alignment of the two sequences. Generally, the comparison window is at least 20 contiguous nucleotides in length, and optionally can be 30, 40, 50, 100, or longer. Those of skill in the art understand that to accurately reflect the similarity to a reference sequence due to inclusion of gaps in the polynucleotide sequence a gap penalty is typically introduced and is subtracted from the number of matches.

Methods of alignment of sequences for comparison are well known in the art. Thus, the determination of percent identity between any two sequences can be accomplished using a mathematical algorithm.

Optimal alignment of sequences for comparison can use any means to analyze sequence identity (homology) known in the art, e.g., by the progressive alignment method of termed "PILEUP" (Morrison, (1997) Mol. Biol. Evol. 14:428-441, as an example of the use of PILEUP); by the local homology algorithm of Smith & Waterman (Adv. Appl. Math. 2: 482 (1981)); by the homology alignment algorithm of Needleman & Wunsch (J. Mol. Biol. 48:443-453 (1970)); by the search for similarity method of Pearson (Proc. Natl. Acad. Sci. USA 85: 2444 (1988)); by computerized implementations of these algorithms (e.g., GAP, BEST FIT, FASTA, and TFASTA in the Wisconsin Genetics Software Package, Genetics Computer Group, 575 Science Dr., Madison, Wis.); ClustalW (CLUSTAL in the PC/Gene program by Intelligenetics, Mountain View, Calif., described by, e.g., Higgins (1988), Gene 73: 237-244; Corpet (1988), Nucleic Acids Res. 16:10881-10890; Huang, Computer Applications in the Biosciences 8:155-165 (1992); and Pearson (1994), Methods in Mol. Biol. 24:307-331); Pfam (Sonnhammer (1998), Nucleic Acids Res. 26:322-325); TreeAlign (Hein (1994), Methods Mol. Biol. 25:349-364); MEG-ALIGN, and SAM sequence alignment computer programs; or, by manual visual inspection.

Another example of algorithm that is suitable for determining sequence similarity is the BLAST algorithm, which is described in Altschul et al, (1990) J. Mol. Biol. 215: 403-410. The BLAST programs (Basic Local Alignment Search Tool) of Altschul, S. F., et al., (1993) J. Mol. Biol. 215:403-410) searches under default parameters for identity to sequences contained in the BLAST "GENEMBL" database. A sequence can be analyzed for identity to all publicly available DNA sequences contained in the GENEMBL database using the BLASTN algorithm under the default parameters.

Software for performing BLAST analyses is publicly available through the National Center for Biotechnology Information, www.ncbi.nlm nih gov/; see also Zhang (1997), Genome Res. 7:649-656 for the "PowerBLAST" variation. This algorithm involves first identifying high scoring sequence pairs (HSPs) by identifying short words of length W in the query sequence that either match or satisfy some positive valued threshold score T when aligned with a word of the same length in a database sequence. T is referred to as the neighborhood word score threshold (Altschul et al (1990), J. Mol. Biol. 215: 403-410). These initial neighborhood word hits act as seeds for initiating searches to find longer HSPs containing them. The word hits are extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word-length (W) of 11, the BLOSUM62 scoring matrix (see Henikoff (1992), Proc. Natl. Acad. Sci. USA 89:10915-10919) alignments (B) of 50, expectation (E) of 10, M=5, N=−4, and a comparison of both strands. The term BLAST refers to the BLAST algorithm which performs a statistical analysis of the similarity between two sequences; see, e.g., Karlin (1993), Proc. Natl. Acad. Sci. USA 90:5873-5787. One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

In an embodiment, GAP (Global Alignment Program) can be used. GAP uses the algorithm of Needleman and Wunsch (J. Mol. Biol. 48:443-453, 1970) to find the alignment of two complete sequences that maximizes the number of matches and minimizes the number of gaps. Default gap creation penalty values and gap extension penalty values in the commonly used Version 10 of the Wisconsin Package™ (Accelrys, Inc., San Diego, Calif.) for protein sequences are 8 and 2, respectively. For nucleotide sequences the default gap creation penalty is 50 while the default gap extension penalty is 3. Percent Similarity is the percent of the symbols that are similar. Symbols that are across from gaps are ignored. A similarity is scored when the scoring matrix value for a pair of symbols is greater than or equal to 0.50, the similarity threshold. A general purpose scoring system is the BLOSUM62 matrix (Henikoff and Henikoff (1993), Proteins 17: 49-61), which is currently the default choice for BLAST programs. BLOSUM62 uses a combination of three matrices to cover all contingencies. Altschul, J. Mol. Biol. 36: 290-300 (1993), and is the scoring matrix used in Version 10 of the Wisconsin Package™ (Accelrys, Inc., San Diego, Calif.) (see Henikoff & Henikoff (1989) Proc. Natl. Acad. Sci. USA 89:10915).

(c) As used herein, "sequence identity" or "identity" in the context of two nucleic acid sequences makes reference to the residues in the two sequences that are the same when aligned for maximum correspondence over a specified comparison window.

(d) As used herein, "percentage of sequence identity" means the value determined by comparing two optimally aligned sequences over a comparison window, wherein the portion of the polynucleotide sequence in the comparison window may include additions or deletions (e.g., gaps) as compared to the reference sequence (which does not include additions or deletions) for optimal alignment of the two sequences. The percentage is calculated by determining the number of positions at which the identical nucleic acid base occurs in both sequences to yield the number of matched positions, dividing the number of matched positions by the total number of positions in the window of comparison, and multiplying the result by 100 to yield the percentage of sequence identity.

Identity to the disclosed sequence would mean a polynucleotide sequence having at least 65% sequence identity, more preferably at least 70% sequence identity to SEQ ID NO: 2, more preferably at least 75% sequence identity, more preferably at least 80% identity, more preferably at least 85% 86%, 87%, 88%, 89%, 90%, 91%, 92%, 93%, 94%, 95%, 96%, 97%, 98%, 99% sequence identity to SEQ ID NO: 2.

In accordance with one embodiment, the disclosed nucleic acid molecule may be constructed by the following steps. The sequence is compared with known nucleic acid sequences, such as sequences in genomic databases. In one embodiment, this comparison is made in the GenBank database using a program such as FASTA (Genetics Computer Group, Madison, Wis.). Additional suitable databases and comparison programs are known to a person of skill in the art. Segments of sequence similar to the query sequence, i.e., the known or newly discovered promoter, are identified and selected. Segments are considered similar if they have between 60% and 100% sequence identity over the segment being examined. These segments can be 20-100 bases in length, although smaller or longer segments can also be selected. The selected sequences are aligned in linear order according to the sequence being modified. The resultant sequence is a hybrid including sequences similar to but different from the original sequence. The synthetic hybrid sequence is then constructed and empirically tested in a test expression system to determine its quantitative and qualitative characteristics. If the synthetic hybrid sequence has maintained or improved activity, it may be used directly. If the synthetic hybrid sequence has a lower activity, the sequence of the synthetic hybrid sequence is further modified by replacing some of the bases to generate a new hybrid sequence. The new hybrid sequence is again constructed and tested to determine if it has the desired maintained or improved activity. This procedure can be performed as often as necessary to derive the final hybrid sequence having the desired activity.

The disclosed sequence further encompasses "functional variants". Functional variants include, for example, disclosed sequences having one or more nucleotide substitutions, deletions or insertions and wherein the variant retains drought tolerance activity. Functional variants can be created by any of a number of methods available to one skilled in the art, such as by site-directed mutagenesis, induced mutation, identified as allelic variants, cleaving through use of restriction enzymes, or the like. Activity can likewise be measured by any variety of techniques, including measurement of reporter activity as is described in U.S. Pat. No. 6,844,484, Northern blot analysis, or similar techniques.

Disclosed is a "functional fragment," that is, a nucleic acid sequence or polypeptide sequence fragment formed by one or more deletions from a larger NDR1 sequence. Such fragments should retain drought tolerance activity, particularly the ability to increase drought tolerance in a plant compared to a plant which does not have the sequence or expresses the NDR1 polypeptide at lower levels. Activity can be measured by Northern blot analysis, reporter activity measurements when using transcriptional fusions, and the like. See, for example, Sambrook et al. (1989). Functional fragments can be obtained by use of restriction enzymes to cleave the naturally occurring nucleotide sequences disclosed herein; by synthesizing a nucleotide sequence from the naturally occurring DNA sequence; or can be obtained through the use of PCR technology. See, Mullis et al. (1987) Methods Enzymol. 155:335-350) and Erlich, ed. (1989) PCR Technology (Stockton Press, New York).

For example, a routine way to remove part of a DNA sequence is to use an exonuclease in combination with DNA amplification to produce unidirectional nested deletions of double stranded DNA clones. A commercial kit for this purpose is sold under the trade name Exo-Size™ (New England Biolabs, Beverly, Mass.). Briefly, this procedure entails incubating exonuclease III with DNA to progressively remove nucleotides in the 3' to 5' direction at 5' overhangs, blunt ends or nicks in the DNA template. However, exonuclease III is unable to remove nucleotides at 3', 4-base overhangs. Timed digests of a clone with this enzyme produces unidirectional nested deletions.

Any plant promoter can be used as a 5' regulatory element for modulating expression of a particular gene or genes operably associated thereto. When operably linked to a transcribable polynucleotide molecule, a promoter typically causes the transcribable polynucleotide molecule to be transcribed in a manner that is similar to that of which the promoter is normally associated. Plant promoters can include promoters produced through the manipulation of known promoters to produce artificial, chimeric, or hybrid promoters. Such promoters can also combine cis elements from one or more promoters, for example, by adding a heterologous regulatory element to an active promoter with its own partial or complete regulatory elements. The range of available plant compatible promoters which may be used in producing a construct includes constitutive, tissue specific and inducible promoters.

By "promoter" is meant a regulatory element of DNA capable of regulating the transcription of a sequence linked thereto. It usually includes a TATA box capable of directing RNA polymerase II to initiate RNA synthesis at the appropriate transcription initiation site for a particular coding sequence. The promoter is the minimal sequence sufficient to direct transcription in a desired manner. The term "regulatory element" in this context is also used to refer to a sequence capable of "regulatory element activity," e.g., regulating transcription in a desired manner.

Disclosed is the NDR1 promoter sequence set forth as SEQ ID NO:3 and shown in FIG. 9. The disclosed regulatory element including those sequences which hybridize to and have identity to SEQ ID NO. 3, and fragments and variants of same which have regulatory activity are included. The TATA box is shown in bold, the CAAT box is shown in italics and the transcription start site is indicated by underlining.

A "functional fragment," of the promoter, that is, a regulatory sequence fragment formed by one or more deletions from a larger regulatory element is also disclosed. For example, the 5' portion of a promoter up to the TATA box near the transcription start site can be deleted without abolishing promoter activity. Such fragments should retain promoter activity, particularly the ability to drive expression of operably linked nucleotide sequences. Activity can be measured by Northern blot analysis, reporter activity measurements when using transcriptional fusions, and the like. See, for example, Sambrook et al. (1989), infra. Functional fragments can be obtained by use of restriction enzymes to cleave the naturally occurring regulatory element nucleotide sequences disclosed herein; by synthesizing a nucleotide sequence from the naturally occurring DNA sequence; or can be obtained through the use of PCR technology See particularly, Mullis et al. (1987) Methods Enzymol. 155: 335-350) and Erlich, ed. (1989) PCR Technology (Stockton Press, New York). The NDR1 promoter may be used to drive the expression of the NDR1 nucleotide sequence, or with another different sequence.

Alternatively, the disclosed nucleic acid sequence may be used with a promoter other than its native promoter, and used with any convenient plant promoter, which may be constitutive, tissue-preferred, inducible or the like. Constitutive promoters include, for example, the core CaMV 35S promoter (Odell et al. (1985) Nature 313:810-812); rice actin (McElroy et al. (1990) Plant Cell 2:163-171); ubiquitin (European patent application no. 0 342 926; Christensen et al. (1989) Plant Mol. Biol. 12:619-632 and Christensen et al. (1992) Plant Mol. Biol. 18:675-689); pEMU (Last et al. (1991) Theor. Appl. Genet. 81:581-588); MAS (Velten et al. (1984) EMBO J. 3:2723-2730), the core promoter of the Rsyn7 promoter and other constitutive promoters disclosed in WO 99/43838 and U.S. Pat. No. 6,072,050; rice actin (McElroy et al. (1990) Plant Cell 2:163-171); pEMU (Last et al. (1991) Theor. Appl. Genet. 81:581-588); MAS (Velten et al. (1984) EMBO J. 3:2723-2730); ALS promoter (U.S. Pat. No. 5,659,026); rice actin promoter (U.S. Pat. No. 5,641,876; WO 00/70067), maize histone promoter (Chaboute et al. Plant Molecular Biology, 8:179-191 (1987), Brignon et al., Plant Mol Bio 22(6):1007-1015 (1993); Rasco-Gaunt et al., Plant Cell Rep. 21(6):569-576 (2003)) and the like. The nopaline synthase (nos) promoter is shown at Depicker et al. (1982) Journal of Mol. and Appl. Genetics 561-573. Other constitutive promoters include, for example, U.S. Pat. Nos. 5,608,149; 5,608,144; 5,604,121; 5,569,597; 5,466,785; 5,399,680; 5,268,463; and 5,608,142.

Tissue-preferred promoters can be utilized to target enhanced transcription or expression or both within a particular plant tissue. When referring to preferential expression, what is meant is expression at a higher level in the particular plant tissue than in other plant tissue. Examples of these type of promoters include seed preferred expression such as that provided by the phaseolin promoter (Bustos et al. (1989) The Plant Cell Vol. 1, 839-853), and the maize globulin-1 gene, Belanger, et al. (1991) Genetics 129:863-972. For dicots, seed-preferred promoters include, but are not limited to, bean β-phaseolin, napin, β-conglycinin, soybean lectin, cruciferin, and the like. For monocots, seed-preferred promoters include, but are not limited to, maize 15 kDa zein, 22 kDa zein, 27 kDa zein, γ zein, waxy, shrunken 1, shrunken 2, globulin 1, an Ltp1 (See, for example, U.S. Pat. No. 7,550,579), an Ltp2 (Opsahl-Sorteberg, H-G. et al., (2004) Gene 341:49-58), and oleosin genes. See also WO 00/12733, where seed-preferred promoters from end1 and end2 genes are disclosed. Seed-preferred promoters also include those promoters that direct gene expression predominantly to specific tissues within the seed such as, for example, the endosperm-preferred promoter of γ-zein, the cryptic promoter from tobacco (Fobert et al. (1994) "T-DNA tagging of a seed coat-specific cryptic promoter in tobacco" Plant J. 4: 567-577); the Pgene promoter from corn (Chopra et al. (1996) "Alleles of the maize P gene with distinct tissue specificities encode Myb-homologous proteins with C-terminal replacements" Plant Cell 7:1149-1158, Erratum in Plant Cell 1997, 1:109); the globulin-1 promoter from corn (Belanger and Kriz (1991) "Molecular basis for Allelic Polymorphism of the maize Globulin-1 gene" Genetics 129: 863-972 and GenBank accession No. L22344); promoters that direct expression to the seed coat or hull of corn kernels, for example the pericarp-specific glutamine synthetase promoter (Muhitch et al., (2002) "Isolation of a Promoter Sequence From the Glutamine Synthetase 1-2 Gene Capable of Conferring Tissue-Specific Gene Expression in Transgenic Maize" Plant Science 163:865-872 and GenBank accession number AF359511) and to the embryo (germ) such as that disclosed in U.S. Pat. No. 7,169,967.

An inducible regulatory element is one that is capable of directly or indirectly activating transcription of one or more DNA sequences or genes in response to an inducer. In the absence of an inducer the DNA sequences or genes will not be transcribed. Typically the protein factor that binds specifically to an inducible regulatory element to activate transcription is present in an inactive form which is then directly or indirectly converted to the active form by the inducer. The inducer can be a chemical agent such as a protein, metabolite, growth regulator, herbicide or phenolic compound or a physiological stress imposed directly by drought, heat, cold, salt, or toxic elements or indirectly through the action of a pathogen or disease agent such as a virus. A plant cell containing an inducible regulatory element may be exposed to an inducer by externally applying the inducer to the cell or plant such as by spraying, watering, heating or similar methods. Any inducible promoter can be used. See Ward et al. Plant Mol. Biol. 22: 361-366 (1993). Exemplary inducible promoters include ecdysone receptor promoters, U.S. Pat. No. 6,504,082; promoters from the ACE1 system which responds to copper (Mett et al. PNAS 90: 4567-4571 (1993)); In2-1 and In2-2 gene from maize which respond to benzenesulfonamide herbicide safeners (U.S. Pat. No. 5,364,780; Hershey et al., Mol. Gen. Genetics 227: 229-237 (1991) and Gatz et al., Mol. Gen. Genetics 243: 32-38 (1994)) Tet repressor from Tn10 (Gatz et al., Mol. Gen. Genet. 227: 229-237 (1991); or from a steroid hormone gene, the transcriptional activity of which is induced by a glucocorticosteroid hormone. Schena et al., Proc. Natl. Acad. Sci. U.S.A. 88: 10421 (1991); the maize GST promoter, which is activated by hydrophobic electrophilic compounds that are used as pre-emergent herbicides; and the tobacco PR-la promoter, which is activated by salicylic acid. Other chemical-regulated promoters of interest include steroid-responsive promoters (see, for example, the glucocorticoidinducible promoter in Schena et al. (1991) Proc. Natl. Acad. Sci. USA 88:10421-10425 and McNellis et al. (1998) Plant J. 14(2):247-257) and tetracycline-inducible and tetracyclinerepressible promoters (see, for example, Gatz et al. (1991) Mol. Gen. Genet. 227:229-237, and U.S. Pat. Nos. 5,814,618 and 5,789,156).

As used herein, a nucleotide segment is referred to as "operably linked" when it is placed into a functional relationship with another DNA segment. For example, DNA for a signal sequence is operably linked to DNA encoding a polypeptide if it is expressed as a preprotein that participates in the secretion of the polypeptide; a promoter or enhancer is operably linked to a coding sequence if it stimulates the transcription of the sequence. Generally, DNA sequences that are operably linked are contiguous, and in the case of a signal sequence both contiguous and in reading phase. However, enhancers need not be contiguous with the coding sequences whose transcription they control. Linking is accomplished by ligation at convenient restriction sites or at adapters or linkers inserted in lieu thereof. The expression cassette can include one or more enhancers in addition to the promoter. By "enhancer" is intended a cis-acting sequence that increases the utilization of a promoter. Such enhancers can be native to a gene or from a heterologous gene. Further, it is recognized that some promoters can contain one or more native, enhancers or enhancer-like elements. An example of one such enhancer is the 35S enhancer, which can be a single enhancer, or duplicated. See for example, McPherson et al, U.S. Pat. No. 5,322,938.

Other components of a vector used to introduce the nucleic acid molecule may also be included, as desired. Examples include selectable markers, targeting or regulatory sequences, stabilizing or leader sequences, introns or the like. Including introns are one of the many examples of means to control expression, and to increase expression of mRNA and of a polypeptide encoded by a nucleic acid molecule. (Buchman and Berg (1988) Mol. Cell Biol. 8: 4395-4405; Callis et al. (1987) Genes Dev 1:1183-1200). General descriptions and examples of plant expression vectors and reporter genes can be found in Gruber, et al., "Vectors for Plant Transformation" in Method in Plant Molecular Biology and Biotechnology, Glick et al eds; CRC Press pp. 89-119 (1993). The selection of an appropriate expression vector will depend upon the host and the method of introducing the expression vector into the host. The expression cassette will also include at the 3' terminus of the heterologous nucleotide sequence of interest, a transcriptional and translational termination region functional in plants.

In one embodiment, the expression vector also contains a gene encoding a selectable or scoreable marker that is operably or functionally linked to a promoter that controls transcription initiation. Examples of selectable markers include those that confer resistance to antimetabolites such as herbicides or antibiotics, for example, dihydrofolate reductase, which confers resistance to methotrexate (Reiss, (1994) Plant Physiol. (Life Sci. Adv.) 13:143-149; see also Herrera Estrella et al., (1983) Nature 303:209-213; Meijer et al., (1991) Plant Mol. Biol. 16:807-820); neomycin phosphotransferase, which confers resistance to the aminoglycosides neomycin, kanamycin and paromycin (Herrera-Estrella, (1983) EMBO J. 2:987-995, and Fraley et al. (1983) Proc. Natl. Acad. Sci USA 80:4803) and hygro, which confers resistance to hygromycin (Marsh, (1984) Gene 32:481-485; see also Waldron et al., (1985) Plant Mol. Biol. 5:103-108; Zhijian et al., (1995) Plant Science 108:219-227); trpB, which allows cells to utilize indole in place of tryptophan; hisD, which allows cells to utilize histinol in place of histidine (Hartman, (1988) Proc. Natl. Acad. Sci., USA 85:8047); mannose-6-phosphate isomerase which allows cells to utilize mannose (WO 94/20627); ornithine decarboxylase, which confers resistance to the ornithine decarboxylase inhibitor, 2-(difluoromethyl)-DL-ornithine (DFMO; McConlogue, (1987), in: Current Communications in Molecular Biology, Cold Spring Harbor Laboratory ed.); and deaminase from *Aspergillus terreus*, which confers resistance to Blasticidin S (Tamura, (1995) Biosci. Biotechnol. Biochem. 59:2336-2338). Additional selectable markers include, for example, a mutant EPSPV-synthase, which confers glyphosate resistance (Hinchee et al., (1998) Bio-Technology 91:915-922), a mutant acetolactate synthase, which confers imidazolinone or sulfonylurea resistance (Lee et al., (1988) EMBO J. 7:1241-1248), a mutant psbA, which confers resistance to atrazine (Smeda et al., (1993) Plant Physiol. 103:911-917), or a mutant protoporphyrinogen oxidase (see U.S. Pat. No. 5,767,373), or other markers conferring resistance to an herbicide such as glufosinate. Examples of suitable selectable marker genes include, but are not limited to, genes encoding resistance to chloramphenicol (Herrera Estrella et al., (1983) EMBO J. 2:987-992); streptomycin (Jones et al., (1987) Mol. Gen. Genet. 210:86-91); spectinomycin (Bretagne-Sagnard et al., (1996) Transgenic Res. 5:131-137,); bleomycin (Hille et al., (1990) Plant Mol. Biol. 7:171-176,); sulfonamide (Guerineau et al., (1990) Plant Mol. Biol. 15:127-136); bromoxynil (Stalker et al., (1988) Science(1986) 242:419-423); glyphosate (Shaw et al., Science 233:478-481); phosphinothricin (DeBlock et al., (1987) EMBO J. 6:2513-2518), and the like. One option for use of a selective gene is a glufosinate-resistance encoding DNA and in one embodiment can be the phosphinothricin acetyl transferase (PAT), maize optimized PAT gene or bar gene under the control of the CaMV 35S or ubiquitin promoters. The genes confer resistance to bialaphos. See, Gordon-Kamm et al., (1990) Plant Cell 2:603; Uchimiya et al., (1993) BioTechnology 11:835; White et al., Nucl. Acids Res. 18:1062, (1990); Spencer et al., 1990) Theor. Appl. Genet. 79:625-631, and Anzai et al., (1989) Mol. Gen. Gen. 219:492. A version of the PAT gene is the maize optimized PAT gene, described in U.S. Pat. No. 6,096,947.

In addition, markers that facilitate identification of a plant cell containing the polynucleotide encoding the marker may be employed. Scorable or screenable markers are useful, where presence of the sequence produces a measurable product and can produce the product without destruction of the plant cell. Examples include a β-glucuronidase, or uidA gene (GUS), which encodes an enzyme for which various chromogenic substrates are known (for example, U.S. Pat. Nos. 5,268,463 and 5,599,670); chloramphenicol acetyl transferase (Jefferson et al. (1987) The EMBO Journal vol. 6 No. 13 pp. 3901-3907); alkaline phosphatase. Other screenable markers include the anthocyanin/flavonoid genes in general (See discussion at Taylor and Briggs, (1990) The Plant Cell 2:115-127) including, for example, a R-locus gene, which encodes a product that regulates the production of anthocyanin pigments (red color) in plant tissues (Dellaporta et al., in Chromosome Structure and Function, Kluwer Academic Publishers, Appels and Gustafson eds., pp. 263-282 (1988)); the genes which control biosynthesis of flavonoid pigments, such as the maize C1 gene (Kao et al., (1996) Plant Cell 8: 1171-1179; Scheffler et al. (1994) Mol. Gen. Genet. 242:40-48) and maize C2 (Wienand et al., (1986) Mol. Gen. Genet. 203:202-207); the B gene (Chandler et al., (1989) Plant Cell 1:1175-1183), the p1 gene (Grotewold et al, (1991 Proc. Natl. Acad. Sci USA) 88:4587-4591; Grotewold et al., (1994) Cell 76:543-553; Sidorenko et al., (1999) Plant Mol. Biol. 39:11-19); the bronze locus genes (Ralston et al., (1988) Genetics 119:185-197; Nash et al., (1990) Plant Cell 2(11): 1039-1049), among others. Yet further examples of suitable markers include the cyan fluorescent protein (CYP) gene (Bolte et al. (2004) J. Cell Science 117: 943-54 and Kato et al. (2002) Plant Physiol 129: 913-42), the yellow fluorescent protein gene (PhiYFP_ from Evrogen; see Bolte et al. (2004) J. Cell Science 117: 943-54); a lux gene, which encodes a luciferase, the presence of which may be detected using, for example, X-ray film, scintillation counting, fluorescent spectrophotometry, low-light video cameras, photon counting cameras or multiwell luminometry (Teeri et al. (1989) EMBO J. 8:343); a green fluorescent protein (GFP) gene (Sheen et al., (1995) Plant J. 8(5):777-84); and DsRed where plant cells transformed with the marker gene are red in color, and thus visually selectable (Dietrich et al. (2002) Biotechniques 2(2):286-293). Additional examples include a placta-mase gene (Sutcliffe, (1978) Proc. Nat'l. Acad. Sci. U.S.A. 75:3737), which encodes an enzyme for which various chromogenic substrates are known (e.g., PADAC, a chromogenic cephalosporin); a xylE gene (Zukowsky et al., (1983) Proc. Nat'l. Acad. Sci. U.S.A. 80:1101), which encodes a catechol dioxygenase that can convert chromogenic catechols; an α-amylase gene (Ikuta et al., (1990) Biotech. 8:241); and a tyrosinase gene (Katz et al., (1983) J. Gen. Microbiol. 129:2703), which encodes an enzyme capable of oxidizing tyrosine to DOPA and dopaquinone, which in turn condenses to form the easily detectable compound melanin. Clearly, many such markers are available to one skilled in the art.

The expression vector can optionally also contain a "signal sequence" located between the promoter and the gene of interest or after the gene of interest. A "signal sequence" is a nucleotide sequence, translated to give an amino acid sequence, which is used by a cell to direct the protein or polypeptide of interest to be placed in a particular place within or outside the eukaryotic cell. Many signal sequences are known in the art. See, for example Becker et al., (1992) Plant Mol. Biol. 20:49, Knox, C., et al., "Structure and Organization of Two Divergent Alpha-Amylase Genes from Barley", Plant Mol. Biol. 9:3-17 (1987), Lerner et al., (1989) Plant Physiol. 91:124-129, Fontes et al., (1991) Plant Cell 3:483-496, Matsuoka et al., (1991) Proc. Natl. Acad. Sci. 88:834, Gould et al., (1989) J. Cell. Biol. 108:1657, Creissen et al., (1991) Plant J. 2:129, Kalderon, et al., (1984) "A short amino acid sequence able to specify nuclear location," Cell 39:499-509, Steifel, et al., (1990) "Expression of a maize cell wall hydroxyproline-rich glycoprotein gene in early leaf and root vascular differentiation" Plant Cell 2:785-793. When targeting the enzyme to the cell wall use of a signal sequence is necessary. One example is the barley alpha-amylase signal sequence. Rogers, J. C. (1985) "Two barley alpha-amylase gene families are regulated differently in aleurone cells" J. Biol. Chem. 260: 3731-3738.

Leader sequences can be included to enhance translation. Various available leader sequences may be substituted or added. Translation leaders are known in the art and include, for example: picornavirus leaders, for example, EMCV leader (encephalomyocarditis 5' noncoding region) (Elroy-Stein et al. (1989) Proc. Natl. Acad. Sci. USA 86:6126-6130); potyvirus leaders, for example, TEV leader (Tobacco Etch Virus) (Gallie et al. (1995) Gene 165 (2):233-8); human immunoglobulin heavy-chain binding protein (BiP) (Macejak et al. (1991) Nature 353:90-94); untranslated leader from the coat protein mRNA of alfalfa mosaic virus (AMV RNA 4) (Jobling et al. (1987) Nature 325:622-625); tobacco mosaic virus leader (TMV) (Gallie. (1987) Nucleic Acids Res. 15(8):3257-73); and maize chlorotic mottle virus leader (MCMV) (Lommel et al. (1991) Virology 81:382-385). See also, Della-Cioppa et al. (1987) Plant Physiology 84:965-968.

In those instances where it is desirable to have the expressed product of the heterologous nucleotide sequence directed to a particular organelle, particularly the plastid, amyloplast, or to the endoplasmic reticulum, or secreted at the cell's surface or extracellularly, the expression cassette can further include a coding sequence for a transit peptide. Such transit peptides are well known in the art and include, but are not limited to, the transit peptide for the acyl carrier protein, the small subunit of RUBISCO, plant EPSP synthase, *Zea mays* Brittle-1 chloroplast transit peptide (Nelson et al. Plant Physiol 117(4):1235-1252 (1998); Sullivan et al. Plant Cell 3(12):1337-48; Sullivan et al., Planta (1995) 196(3):477-84; Sullivan et al., J. Biol. Chem. (1992) 267 (26):18999-9004) and the like. One skilled in the art will readily appreciate the many options available in expressing a product to a particular organelle. For example, the barley alpha amylase sequence is often used to direct expression to the cell wall (Rogers, J. Biol. Chem. 260:3731-3738 (1985)). Use of transit peptides is well known (e.g., see U.S. Pat. Nos. 5,717,084; 5,728,925). A protein may be targeted to the endoplasmic reticulum of the plant cell. This may be accomplished by use of a localization sequence, such as KDEL. This sequence (Lys-Asp-Glu-Leu) contains the binding site for a receptor in the endoplasmic reticulum. (Munro et al., (1987) "A C-terminal signal prevents secretion of luminal ER proteins." Cell. 48:899-907. Retaining the enzyme in the vacuole is another example. Signal sequences to accomplish this are well known. For example, Raikhel U.S. Pat. No. 5,360,726 shows a vacuole signal sequence as does Warren et al. at U.S. Pat. No. 5,889,174. Vacuolar targeting signals may be present either at the amino-terminal portion, (Holwerda et al., (1992) The Plant Cell, 4:307-318, Nakamura et al., (1993) Plant Physiol., 101:1-5), carboxy-terminal portion, or in the internal sequence of the targeted protein. (Tague et al., (1992) The Plant Cell, 4:307-318, Saalbach et al. (1991) The Plant Cell, 3:695-708). Additionally, amino-terminal sequences in conjunction with carboxy-terminal sequences are responsible for vacuolar targeting of gene products (Shinshi et al. (1990) Plant Molec. Biol. 14:357-368).

The termination region can be native with the nucleotide sequence, can be native with the DNA sequence of interest, or can be derived from another source. Convenient termination regions are available from the Ti-plasmid of A, *tumefaciens*, such as the octopine synthase (MacDonald et al., (1991) Nuc. Acids Res. 19(20)5575-5581) and nopaline synthase termination regions (Depicker et al., (1982) Mol. and Appl. Genet. 1:561-573 and Shaw et al. (1984) Nucleic Acids Research Vol. 12, No. 20 pp 7831-7846 (nos)). Examples of various other terminators include the pin II terminator from the protease inhibitor II gene from potato (An, et al. (1989) Plant Cell 1, 115-122. See also, Guerineau et al. (1991) Mol. Gen. Genet. 262:141-144; Proudfoot (1991) Cell 64:671-674; Sanfacon et al. (1991) Genes Dev. 5:141-149; Mogen et al. (1990) Plant Cell 2:1261-1272; Munroe et al. (1990) Gene 91:151-158; Ballas et al. (1989) Nucleic Acids Res. 17:7891-7903; and Joshi et al. (1987) Nucleic Acid Res. 15:9627-9639.

Where appropriate, the nucleotide sequence(s) may be optimized for increased expression in the transformed plant. That is, the genes can be synthesized using plant-preferred codons for improved expression. See, for example, Campbell and Gowri (1990) Plant Physiol. 92: 1-11 for a discussion of host-preferred codon usage. Methods are available in the art for synthesizing plant-preferred genes. See, for example, U.S. Pat. Nos. 5,380,831, 5,436,391, and Murray et al. (1989). Additional sequence modifications are known to enhance gene expression in a plant. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

In preparing the nucleotide construct, the various nucleotide sequence fragments can be manipulated, so as to provide for the nucleotide sequences in the proper orientation and, as appropriate, in the proper reading frame. Toward this end, adapters or linkers can be employed to join the nucleotide sequence fragments or other manipulations may be involved to provide for convenient restriction sites, removal of superfluous nucleotide sequences, removal of restriction sites, or the like. For this purpose, in vitro mutagenesis, primer repair, restriction, annealing, resubstitutions, e.g., transitions and transversions, may be involved.

In general, the methods available for construction of recombinant genes, optionally include various modifications for improved expression, can differ in detail. However, conventionally employed methods include PCR amplification, or the designing and synthesis of overlapping, complementary synthetic oligonucleotides, which are annealed and ligated together to yield a gene with convenient restriction sites for cloning, or subcloning from another already cloned source, or cloning from a library. The methods involved are standard methods for a molecular biologist (Sambrook et al., 1989). An expression vector is a DNA molecule comprising a gene or antisense DNA that is expressed in a host cell. Typically, gene expression is placed under the control of certain regulatory elements, including constitutive or inducible promoters, tissue-specific regulatory elements, and enhancers.

A nucleic acid molecule expressing NRD1 may be introduced into a plant cell, or a nucleic acid molecule impacting expression of NRD1 may be introduced into a plant cell, e.g., one which increases or decreases expression of the polypeptide.

The term "plant" is used broadly herein to include any plant at any stage of development, or to part of a plant, including a plant cutting, a plant cell, a plant cell culture, a plant organ, a plant seed, and a plantlet. A plant cell is the structural and physiological unit of the plant, comprising a protoplast and a cell wall. A plant cell can be in the form of an isolated single cell or aggregate of cells such as a friable callus, or a cultured cell, or can be part of a higher organized unit, for example, a plant tissue, plant organ, or plant. Thus, a plant cell can be a protoplast, a gamete producing cell, or a cell or collection of cells that can regenerate into a whole plant. As such, a seed, which includes multiple plant cells and is capable of regenerating into a whole plant, is considered a plant cell for purposes of this disclosure. A plant tissue or plant organ can be a seed, protoplast, callus, or any other groups of plant cells that is organized into a structural or functional unit. Particularly useful parts of a plant include harvestable parts and parts useful for propagation of progeny plants. A harvestable part of a plant can be any useful part of a plant, for example, flowers, pollen, seedlings, tubers, leaves, stems, fruit, seeds, roots, and the like. A part of a plant useful for propagation includes, for example, seeds, fruits, cuttings, seedlings, tubers, rootstocks, and the like. Plants may be regenerated from tissue cultures. The tissue culture will preferably be capable of regenerating plants having the physiological and morphological characteristics of the disclosed plant, and of regenerating plants having substantially the same genotype as the disclosed plant. For example, the regenerable cells in such tissue cultures will be embryos, protoplasts, meristematic cells, callus, pollen, leaves, anthers, roots, root tips, silk, flowers, kernels, ears, cobs, husks or stalks. Plants may be regenerated from tissue cultures.

The disclosed sequences may be used for transformation of any plant species, whether monocotyledonous or dicotyledonous, including but not limited to corn (*Zea mays*), canola (*Brassica napus, Brassica rapa* ssp.), alfalfa (*Medicago sativa*), rice (*Oryza sativa*), rye (*Secale cereale*), sorghum (*Sorghum bicolor, Sorghum vulgare*), sunflower (*Helianthus annuus*), wheat (*Triticum aestivum*), soybean (*Glycine max*), tobacco (*Nicotiana tabacum*), potato (*Solanum tuberosum*), peanuts (*Arachis hypogaea*), cotton (*Gossypium hirsutum*), sweet potato (*Ipomoea batatus*), cassava (*Manihot esculenta*), coffee (*Cofea* spp.), coconut (*Cocos nucifera*), pineapple (*Ananas comosus*), citrus trees (Citrus spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), oats (*Avena*), barley (*Hordeum*), vegetables, ornamentals, and conifers. Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.) and members of the genus Cucumis such as cucumber (*Cucumis sativus*), cantaloupe (*Cucumis cantalupensis*), and musk melon (*Cucumis melo*). Ornamentals include azalea (*Rhododendron* spp.), hydrangea (*Macrophylla hydrangea*), hibiscus (*Hibiscus rosa-sanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum. Conifers which may be used include, for example, pines such as loblolly pine (*Pinus taeda*), slash pine (*Pinus elliotii*), ponderosa pine (*Pinus ponderosa*), lodgepole pine (*Pinus contotta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*).

Methods for introducing expression vectors into plant tissue available to one skilled in the art are varied and will depend on the plant selected. Procedures for transforming a wide variety of plant species are well known and described throughout the literature. (See, for example, Miki and McHugh (2004) Biotechnol. 107, 193-232; Klein et al. (1992) Biotechnology (N Y) 10, 286-291; and Weising et al. (1988) Annu. Rev. Genet. 22, 421-477). For example, the DNA construct may be introduced into the genomic DNA of the plant cell using techniques such as microprojectile-mediated delivery (Klein et al. 1992, supra), electroporation (Fromm et al., 1985 Proc. Natl. Acad. Sci. USA 82, 5824-5828), polyethylene glycol (PEG) precipitation (Mathur and Koncz, 1998 Methods Mol. Biol. 82, 267-276), direct gene transfer (WO 85/01856 and EP-A-275 069), in vitro protoplast transformation (U.S. Pat. No. 4,684,611), and microinjection of plant cell protoplasts or embryogenic callus (Crossway, A. (1985) Mol. Gen. Genet. 202, 179-185). *Agrobacterium* transformation methods of Ishida et al. (1996) and also described in U.S. Pat. No. 5,591,616 are yet another option. Co-cultivation of plant tissue with *Agrobacterium tumefaciens* is a variation, where the DNA constructs are placed into a binary vector system (Ishida et al., 1996 Nat. Biotechnol. 14, 745-750). The virulence functions of the *Agrobacterium tumefaciens* host will direct the insertion of the construct into the plant cell DNA when the cell is infected by the bacteria. See, for example, Fraley et al. (1983) Proc. Natl. Acad. Sci. USA, 80, 4803-4807. *Agrobacterium* is primarily used in dicots, but monocots including maize can be transformed by *Agrobacterium*. See, for example, U.S. Pat. No. 5,550,318. In one of many variations on the method, *Agrobacterium* infection of corn can be used with heat shocking of immature embryos (Wilson et al. U.S. Pat. No. 6,420,630) or with antibiotic selection of Type II callus (Wilson et al., U.S. Pat. No. 6,919,494).

Rice transformation is described by Hiei et al. (1994) Plant J. 6, 271-282 and Lee et al. (1991) Proc. Nat. Acad. Sci. USA 88, 6389-6393. Standard methods for transformation of canola are described by Moloney et al. (1989) Plant Cell Reports 8, 238-242. Corn transformation is described by Fromm et al. (1990) Biotechnology (N Y) 8, 833-839 and Gordon-Kamm et al. (1990) supra. Wheat can be transformed by techniques similar to those used for transforming corn or rice. Sorghum transformation is described by Casas et al. (Casas et al. (1993) Transgenic sorghum plants via microprojectile bombardment. Proc. Natl. Acad. Sci. USA 90, 11212-11216) and barley transformation is described by Wan and Lemaux (Wan and Lemaux (1994) Generation of large numbers of independently transformed fertile barley plants. Plant Physiol. 104, 37-48). Soybean transformation is described in a number of publications, including U.S. Pat. No. 5,015,580.

In a further embodiment, plant breeding can be used to introduce the nucleotide sequences into other plants once transformation has occurred. This can be accomplished by any means known in the art for breeding plants such as, for example, cross pollination of the transgenic plants that are described above with other plants, and selection for plants from subsequent generations which contain the nucleic acid or express the amino acid sequence or trait. The plant breeding methods used herein are well known to one skilled in the art. For a discussion of plant breeding techniques, see Poehlman and Sleper (1995) Breeding Field Crops. AVI Publication Co., Westport Conn., 4th Edit. Many crop plants useful in this method are bred through techniques that take advantage of the plant's method of pollination. A plant is self-pollinating if pollen from one flower is transferred to the same or another flower of the same plant. A plant is cross-pollinating if the pollen comes from a flower on a different plant. For example, in *Brassica*, the plant is normally self-sterile and can only be cross-pollinated unless, through discovery of a mutant or through genetic intervention, self-compatibility is obtained. In self-pollinating species, such as rice, oats, wheat, barley, peas, beans, soybeans, tobacco and cotton, the male and female plants are anatomically juxtaposed. During natural pollination, the male reproductive organs of a given flower pollinate the female reproductive organs of the same flower. Maize plants (*Zea mays* Lg.) can be bred by both self-pollination and cross-pollination techniques. Maize has male flowers, located on the tassel, and female flowers, located on the ear, on the same plant. It can self or cross-pollinate.

Pollination can be by any means, including but not limited to hand, wind or insect pollination, or mechanical contact between the male fertile and male sterile plant. For production of hybrid seeds on a commercial scale in most plant species pollination by wind or by insects is preferred. Stricter control of the pollination process can be achieved by using a variety of methods to make one plant pool male sterile, and the other the male fertile pollen donor. This can be accomplished by hand detassling, cytoplasmic male sterility, or control of male sterility through a variety of methods well known to the skilled breeder.

Backcrossing methods may be used to introduce the gene into the plants. This technique has been used for decades to introduce traits into a plant. An example of a description of this and other plant breeding methodologies that are well known can be found in references such as Poehlman et al. (1995), supra. In a typical backcross protocol, the original variety of interest (recurrent parent) is crossed to a second variety (nonrecurrent parent) that carries the single gene of interest to be transferred. The resulting progeny from this cross are then crossed again to the recurrent parent and the process is repeated until a plant is obtained wherein essentially all of the desired morphological and physiological characteristics of the recurrent parent are recovered in the converted plant, in addition to the single transferred gene from the nonrecurrent parent. Backcrossing methods may be used to introduce a gene into the plants. This technique has been used for decades to introduce traits into a plant. An example of a description of this and other plant breeding methodologies that are well known can be found in references such as Poehlman, supra, and Plant Breeding Methodology, edit. Neal Jensen, John Wiley & Sons, Inc. (1988).

When referring to "introduction" of the nucleotide sequence into a plant, it is meant that this can occur by direct transformation methods, such as *Agrobacterium* transformation of plant tissue, microprojectile bombardment, electroporation, or any one of many methods known to one skilled in the art; or, it can occur by crossing a plant having the heterologous nucleotide sequence with another plant so that progeny have the nucleotide sequence incorporated into their genomes.

Such breeding techniques are well known to one skilled in the art, as described in brief above.

Exemplary non-limiting embodiments are provided below.

1. An isolated polypeptide comprising an amino acid sequence having at least 80% sequence identity to SEQ ID NO: 1, wherein the polypeptide provides drought tolerance when expressed in a plant.
2. An isolated polypeptide comprising an amino acid sequence having at least 80% sequence identity to SEQ ID NO: 1, wherein the polypeptide provides improved drought tolerance when expressed in a plant compared to a plant that does not express SEQ ID NO: 1
3. An isolated polypeptide comprising an amino acid sequence having at least 80% sequence identity to a NON-RACE SPECIFIC DISEASE RESISTANCE (NDR1) polypeptide, wherein the polypeptide provides drought tolerance when expressed in a plant.
4. An isolated polypeptide comprising an amino acid sequence having at least 80% sequence identity to a NON-RACE SPECIFIC DISEASE RESISTANCE (NDR1) polypeptide, wherein the polypeptide maintains the plasma membrane-cell wall junction.
5. An isolated polypeptide comprising an amino acid sequence having at least 80% sequence identity to a NON-RACE SPECIFIC DISEASE RESISTANCE (NDR1) polypeptide, wherein the polypeptide restores the plasma membrane-cell wall junction.
6. A recombinant DNA construct comprising a nucleic acid encoding the polypeptide of any of the embodiments 1-5 operably linked to at least one regulatory element.
7. The construct of embodiment 6, wherein the regulatory element is a NDR1 promoter.
8. The construct of embodiment 6, wherein the regulatory element comprises SEQ ID NO: 3.
9. A plant comprising in its genome a recombinant DNA construct comprising a polynucleotide operably linked to at least one regulatory element, wherein the polynucleotide comprises a nucleotide sequence selected from the group consisting of:
   a. a nucleotide sequence comprising SEQ ID NO: 2;
   b. a nucleotide sequence encoding a polypeptide with drought tolerance activity, wherein the polypeptide has an amino acid sequence of at least 80% sequence identity to SEQ ID NO: 1;
   c. a nucleotide sequence encoding a polypeptide with drought tolerance activity, wherein the nucleotide sequence is hybridizable under stringent conditions with a DNA molecule comprising the full complement of SEQ ID NO: 2; and wherein the plant exhibits improved drought tolerance when compared to a plant not comprising the recombinant DNA construct.
10. The plant of embodiment 9, wherein the plant is a monocot or dicot.
11. The plant of embodiment 9, wherein the plant is selected from the group consisting of corn, soybean, sunflower, sorghum, canola, wheat, alfalfa, cotton, rice, barley, tobacco, potato and sugar beet.
12. The plant of embodiment 9, wherein the at least one regulatory element is the NDR1 promoter.
13. The plant of embodiment 9, wherein the at least one regulatory element comprises SEQ ID NO: 3
14. A method of producing a plant having drought tolerance, the method comprising
   a) introducing into at least one plant or plant part a vector comprising a nucleic acid molecule which expresses or increases a polypeptide that confers drought tolerance, the polypeptide selected from the group consisting of,
  a) a nucleotide sequence of SEQ ID NO: 2 or variants thereof;
  b) a nucleotide sequence that encodes a polypeptide comprising the amino acid sequence of SEQ ID NO: 1;
  c) a polypeptide encoding a NON-RACE-SPECIFIC DISEASE RESISTANCE1 (NDR1);
  d) a polypeptide sequence having at least 80% identity to the amino acid sequence of SEQ ID NO: 1, and
  e) a functional fragment of SEQ ID NO: 1;
  b) selecting at least one plant or plant part having improved drought tolerance from a plurality of plants or plant parts into which the vector has been introduced compared to a plant in which no vector has been introduced.

15. The method of embodiment 14 wherein the plant or plant part is a monocot or dicot.
16. The method of embodiment 14, wherein the plant is selected from the group consisting of corn, soybean, sunflower, sorghum, canola, wheat, alfalfa, cotton, rice, barley, tobacco, potato and sugar beet.
17. A plant produced by the method of embodiment 14.
18. A plant part produced by the method of embodiment 14.
19. The plant of embodiment 14, wherein the plant is a seed.
20. A seed produced by the method of embodiment 14.
21. The method of embodiment 14, wherein the vector comprises a constitutive promoter.
22. The method of embodiment 14, wherein the vector comprises a NDR1 promoter.
23. The method of embodiment 14, wherein the plant further reduces electrolyte leakage.

The following non-limiting examples further illustrate some aspects of the disclosed embodiments.

EXAMPLE 1

Materials and Methods
Homology Modeling and Structure Threading

The primary amino acid sequence of NDR1 (AT3G20600) was submitted to the PHYRE protein fold recognition server (www.sbg.bio.ic.ac.uk/phyre/). The predicted structure was analyzed using the MODELER comparative homology-modeling software (Marti-Renom et al., 2000). The output of this analysis, predicted model of all nonhydrogen atoms based on spatial restraints, was then viewed using Chimera (Pettersen et al., 2004). Image overlays were performed using the solved NMR structure of LEA14 (AT1G01470; lyyca; Singh et al., 2005). Further analysis was performed by submitting the primary amino acid sequence of NDR1 to I-TASSER (zhanglab.ccmb.med.umich.edu/I-TASSER), an internet-based structure prediction service.

Plant Growth Conditions

*Arabidopsis thaliana* (*Arabidopsis*) plants were grown at 20° C. under a 12-h/12-h light/dark cycle at 60% relative humidity in a Bio Chambers model FLX-37 growth chamber. *Nicotiana benthamiana* plants were grown under the same conditions.

DNA Cloning and Mutagenesis

Cloning of DNA constructs was performed using standard protocols. Site-directed mutagenesis of NDR1 was performed according to previously published protocols (Day et al., 2005) modified from the QuikChange PCR Mutagenesis Kit (Stratagene). Two site-directed mutations within the NGD site of NDR1, located at amino acids 178 to 180, were constructed. A template plasmid (i.e. pTOPO-NDR1) containing the open reading frame of NDR1 flanked by SalI (5') and SacI (3') restriction enzyme sites was used in combination with the DNA oligonucleotide primer sets labeled RGD and AAA in Supplemental Table 51. Following 18 cycles (95° C. for 1 min, 55° C. for 3 min, 68° C. for 5 min) on a Bio-Rad MyCycler thermal cycler (Bio-Rad Laboratories) using Pfu Turbo DNA polymerase (Clontech), the product was then treated with DpnI for 1 h at 37° C. Five microliters of the digested DNA reaction was transformed into *Escherichia coli* DH5__ cells and grown on Luria-Bertani medium containing 100 μg mL-1 kanamycin overnight at 37° C. Mutant NDR1 constructs were cloned into either the native promoter vector pDDNDR (Coppinger et al., 2004) or the 35S binary vector pMD-1 with an N-terminal T7 epitope tag (Day et al., 2005). To make pDDNDR native promoter constructs, primers were designed to add a 5'T7 epitope tag and SalI site and a 3' SpeI site (Supplemental Table S2). Amplicons from the site-directed mutant constructs were ligated into pGEM T-EASY vector (Promega) and subsequently digested with SalI and SpeI and ligated into pDDNDR (Coppinger et al., 2004). DNA plasmids were transformed and maintained in *E. coli* DH5α cells. The fidelity of all DNA constructs was confirmed by DNA sequencing (ABI 3730 Genetic Analyzer; Applied Biosystems). *Agrobacterium tumefaciens* strain GV3101 (pMP90) (Lazo et al., 1991) and strain C58C1 (Tai et al., 1999; for *N. benthamiana* expression) were transformed with wild-type and NDR1 mutant constructs by electroporation.

All native, wild-type NDR1 T7 and HA fusion constructs were shown to be functional and to fully complement the ndr1-1 mutation (Coppinger et al., 2004; Day et al., 2006).

Cloning of NDR1 Mutant Constructs

Two site-directed mutations within the NGD site of NDR1, located at amino acids 178 to 180, were constructed using a quick-change PCR approach. A template plasmid (e.g. pTOPO-NDR1) containing the open reading frame of NDR1 flanked by SalI (5') and SacI (3') restriction enzyme sites was used in combination with the DNA oligonucleotide primer sets labeled RGD and AAA in Supplemental Table 51. Following 18 cycles (95° C. for 1 min, 55° C. for 3 min, 68° C. for 5 min) on a Bio-Rad MyCycler thermal cycler using Pfu Turbo DNA polymerase (Clontech), the product was then treated with DpnI for 1 h at 37° C. Five microliters of the digested DNA reaction was transformed into *E. coli* DH5α cells and grown on Luria-Bertani medium containing 100 μg mL$^{-1}$ kanamycin overnight at 37° C. The resultant site-directed mutant constructs were digested with SalI and SacI restriction enzymes and ligated into the respective sites in the 35S binary vector pMD-1-T7, which incorporates a 5' T7 epitope tag (Day et al., 2005). To make pDDNDR native promoter constructs, primers were designed to add a 5' T7 epitope tag and SalI site and a 3' SpeI site (Supplemental Table S1). Amplicons from the site-directed mutant constructs were ligated into pGEM T-EASY vector (Invitrogen) and subsequently digested with SalI and SpeI and ligated into pDDNDR (Coppinger et al., 2004). DNA plasmids were transformed and maintained in *E. coli* DH5α cells. *A. tumefaciens* strain GV3101 (pMP90) (Lazo et al., 1991) and strain C58C1 (Tai et al., 1999; for *N. benthamiana* expression) were transformed with wild-type and NDR1 mutant constructs by electroporation. All native, wild-type NDR1 T7 and HA fusion constructs were previously demonstrated to be functional and to fully complement the ndr1-1 mutation (Coppinger et al., 2004; Day et al., 2006).

*Arabidopsis* Transformation

Flowering *Arabidopsis* plants were transformed and selected for homozygosity, as described by Clough and Bent (1998), on Murashige and Skoog medium containing 1% Bacto agar and 25 µg mL-1 kanamycin.

Pathogen Inoculation and Growth Assays

*Pseudomonas syringae* pv tomato DC3000 strains containing pVSP61 (empty vector) or pVSP61-containing AvrRpt2, AvrB, or AvrPphB were described previously (Kunkel et al., 1993; Simonich and Innes, 1995). To assay for bacterial growth, 4-week-old plants were dip inoculated in bacterial suspensions of $3\times10^7$ colony-forming units (cfu) $mL^{-1}$. Leaves were preselected and marked to ensure that analyses were performed on developmentally similar leaves. At 0 and 4 d post-inoculation, three leaf discs of 0.7 cm diameter were collected from a single plant into a microcentrifuge tube containing 1 mM $MgCl_2$+0.1% Triton X-100. Bacterial growth assays were performed as described by Tornero and Dangl (2001) with the modification of plating 5 µL instead of 2 µL, as described by Tian et al. (2009). Results were analyzed for significance using SAS (version 9.2; SAS Software) using an ANOVA model modified from Tsuda et al. (2008; (see below)). Log 10-transformed bacterial titer counts were compared using Tukey's test.

$$\text{Log }10(n)ijk=Ti+Gj+TiGj+ek$$

Where T, treatment; G, genotype; TG, treatment:genotype; e, residual; i, treatment index (1 to 4); j, genotype index (1 to 4), k, replicate index (4 to 6).

Electrolyte Leakage

Electrolyte leakage was measured in 4-to 5-week-old plants using a protocol modified from Gilmour et al. (1988). Leaves were preselected and marked based on similarity in size before plants were dip inoculated at $3\times10^7$ cfu $mL^{-1}$. After inoculation, plants were covered with a clear plastic dome for 30 min before the 0-h time point, when leaves were removed. The remaining pots were left covered for another 2.5 h. A single leaf was removed from a plant and a disc (0.7 cm diameter) was harvested using a number 3 cork borer. Excised leaf discs were floated in a bath of sterile deionized water and quickly swirled before being placed in a tube containing 3 mL of sterile deionized water. Four plants were used for each replicate. Tubes containing leaf discs were shaken on an orbital rocker at 35 rpm for 3 h. After 3 h, leaf discs were removed and the solution was assayed for conductance using a conductance meter (Traceable 23226-505; VWR Scientific). Leaf discs were frozen at −80° C. for 1 h. After the freeze cycle, the leaf punch was returned to the original sample tube and rocked for an additional 3 h at room temperature. After 3 h, the leaf punch was removed and the conductance was measured, recorded as total leakage. Electrolyte leakage was recorded and calculated as percentage leakage of total (i.e. first reading/second reading) adjusted to percentage maximal.

RNA Isolation and Quantitative Real-Time PCR

Total RNA was extracted from leaves using the RNeasy Plant Mini Kit (Qiagen). First-strand cDNA was synthesized from 1 µg of total RNA using SuperScript II reverse transcriptase (Invitrogen). Quantitative real-time PCR (qRT-PCR) was performed on a Mastercycler ep Realplex real-time PCR system (Eppendorf) using HotStart-IT SYBR Green qPCR Master Mix (2×; USB). Cycle time for all replicates was 95° C. for 2 min followed by 40 cycles of 95° C. for 15 s, 60° C. for 15 s, and 72° C. for 45 s. Data were analyzed by two-way ANOVA using Prism 4 (GraphPad Software) with outliers removed by Grubb's test ($\alpha=0.05$) utilizing the QuickCalcs online outlier calculator (GraphPad Software; www.graphpad.com/quickcalcs/Grubbs1.cfm). Aquaporin homolog primers were used as described (Alexandersson et al., 2010). All primer sets utilized are listed in Supplemental Table S2.

HR Assay

The HR was assayed as described by Century et al. (1995), slightly modified, by hand infiltration of *Arabidopsis* leaves with Pst DC3000 using a needleless syringe at a concentration of $1\times10^7$ cfu $cm^{-2}$, following a 6-or 12-h pretreatment by hand infiltration of 5 mM VAAAG, VNGDG, or VRGDG peptide solution in 1 mM $MgCl_2$ buffer or a mock control of only buffer. The leaves were evaluated for tissue collapse 20 h after infiltration of the bacteria.

Plasmolysis

Plasmolysis experiments were performed based on the methods of Gouget et al. (2006) using 8-d-old etiolated hypocotyls with the cotyledons and roots removed. Hypocotyl sections were immersed in 50 mM Tris (pH 8.0) for 1 h at room temperature, rinsed in sterile distilled water, and then stained with 0.05% neutral red for 5 to 30 min. Sections were rinsed in sterile distilled water and mounted on a coverslip in 15 µL of sterile water. A second coverslip was placed on top of the section, offset to the first coverslip. To plasmolyze the cells, 15 µL of 1.0 M CaCl2 was placed on the sample where the second coverslip overlapped the first, allowing the solution to cover the sample via capillary action. Stained, plasmolyzed hypocotyls were observed with an Olympus IX-71 inverted microscope, and images were acquired with an Olympus DP70 camera. Images were processed and adjusted for contrast using Canvas X (ACD Systems). Approximately 100 hypocotyls of each genotype were observed in total from more than five biological replicates. For peptide addition experiments, the same method as described above was followed, with the exception that the hypocotyls were mounted in 15 µL of 5 mM peptide in distilled water. Peptides (VRGDG, VAAAG, and VNGDG) were synthesized by EZ-Biolabs at a purity of greater than 99%.

Tagged Protein Constructs and Coimmunoprecipitation

Coimmunoprecipitation experiments were performed as described by Day et al. (2006), with slight modifications. In brief, *A. tumefaciens* strains expressing the epitope-tagged (e.g. T7 or HA) NDR1, RIN4, and NDR1 mutant constructs fused to a 35S promoter were infiltrated into 5-week-old leaves on *N. benthamiana* at a final, individual concentration of 4×108 cells mL-1. Leaves were incubated at room temperature for 40 h, after which time 16 1-cm2 leaf discs were harvested into liquid nitrogen and held at −80° C. until processing. Samples were processed according to Day et al. (2005).

T7 epitope monoclonal and T7 horseradish peroxidase (HRP)-conjugated antibodies were purchased from Novagen. HA epitope monoclonal antibody was purchased from Covance. HA HRP-conjugated antibody and protease inhibitors were purchased from Roche.

MAPK Western Blotting

To detect MAPK3/6 activity, 40 µg of total protein was loaded onto a 12% SDS-PAGE gel and transferred onto a nitrocellulose membrane, followed by incubation for 1 h with an antibody specific for anti-pTEpY (catalog no. 91015; Cell Signaling Technology). An anti-rabbit HRP secondary antibody was used for detection on film.

Sequence data for sequences used may be found in the GenBank/EMBL data libraries under accession numbers At3g20600 (NDR1), At1g01470 (LEA14), At1g32560 (LEA group 1 domaincontaining protein), At2g39010 (PIP2; 6), At3g54820 (PIP2;5), At4g23400 (PIP1;5), At4g00430 (PIP1;4), At1g01620 (PIP1;3), At2g14610 (PRI), At5g44420 (PDF1.2), At3g03600 (RPS2), and At2g19190 (FRK1).

Modified Electrolyte Leakage: Supplemental Conductance Method

Electrolyte leakage was measured in 4-week-old plants using a protocol modified from Mackey et al. (2002). Plants were dip inoculated at 3×107 cfu mL-1. After inoculation, plants were covered with a clear plastic dome for 1 hour before the 0 hour time point leaves were removed. A leaf disc (0.7 cm diameter) was harvested using a number 3 size cork borer from 2 leaves each from 4 plants. The punches were added to a glass container containing 50 mL of sterile $dH_2O$ and allowed to rotate on orbital shaker for 30 minutes at 20 rpm. After this wash step the $dH_2O$ was removed and replaced by 10 mL sterile $dH_2O$ that had been previously measured for conductance to allow for background to be removed. The samples were allowed to remain on shaker with measurements conducted at 3 hour intervals for 24 hours. Electrolyte leakage was recorded as conductance ($\mu S$). To allow for the calculation of percent maximal leakage, after the final measurement was taken the leaf punches were frozen at −80° C. for 24 hours before being returned to their respective samples, followed by 3 hours on the shaker and a final measurement recorded as total leakage. Total percent leakage can be calculated as first reading/ second reading adjusted to percent maximal leakage.

NDR1 Shares Predicted Structural Homology with LEA14, an Integrin-Like Protein

Two independent methods were used to generate a predicted structure for NDR1 (FIG. 1A). First, the protein fold recognition server PHYRE (Protein Homology/analogY Recognition Engine; Kelley and Sternberg, 2009) was used to generate a predicted structural model.

In the second approach, the automated homology-modeling server I-TASSER was used to generate five predicted structures for NDR1. FIG. 1C shows the NDR1 predicted structure threaded onto the solved structure of LEA14, highlighting the predicted structural homology. N denotes N terminal. PHYRE analysis returned an estimated structural homology precision of 95%, with an E-value of 0.008. The protein homologies when compared to the maize shows 39% homology, in rice, 37% homology and in soybean 51% homology, which, given the evolutionary divergence, are considered high homologies.

Both PHYRE and I-TASSER generated similar homology model predictions for NDR1. Homology modeling and structure threading were used to predict a tertiary fold of NDR1. Once a secondary structure for NDR1 was predicted using PHYRE, homology modeling was performed using MODELER (Martí-Renom et al., 2000) and Chimera (Pettersen et al., 2004). The output of this analysis was then threaded onto the solved structure of the *Arabidopsis* LATE EMBRYOGENESIS ABUNDANT14 (LEA14) protein (FIG. 1B, pdb_1yyc; Singh et al., 2005), a member of the late embryogenesis family of proteins.

Further analysis of the predicted structure was performed in a domain-by-domain manner, from which we identified several striking similarities with mammalian proteins involved in signal perception and innate immune responses. For example, the large β-sheet torus (FIG. 1A, blue arrows) resembles the core structure of type III fibronectins (Potts and Campbell, 1994). Further modeling suggests that the primary core structure of NDR1 shares strong structural similarity with the membrane-bound subunit (e.g. fibronectin FNIII domain) of integrin, with the putative transmembrane domains of both NDR1 and integrin connected to large single-sheets (Hynes, 2009). Overlays of predicted and solved structures were generated using CHIMERA. For generation of the NDR1 β-sheet model, amino acids 34-195 were used. For LEA14, amino acids 40-162 were used based on the solved structure pdb_1yyca (Singh et al., 2005). Adjacent to the three-amino acid α-helix (FIG. 1B, small yellow helix; compare the homologous position in FIG. 1C), we identified the presence of a solvent-exposed RGD-like motif (e.g. NGD) at amino acid positions 178 to 180. In host-fungus interactions, the role of RGD motifs in defense signaling has been characterized as a potential ligand-binding site involved in cell wall-plasma membrane adhesion.

Figure 2:
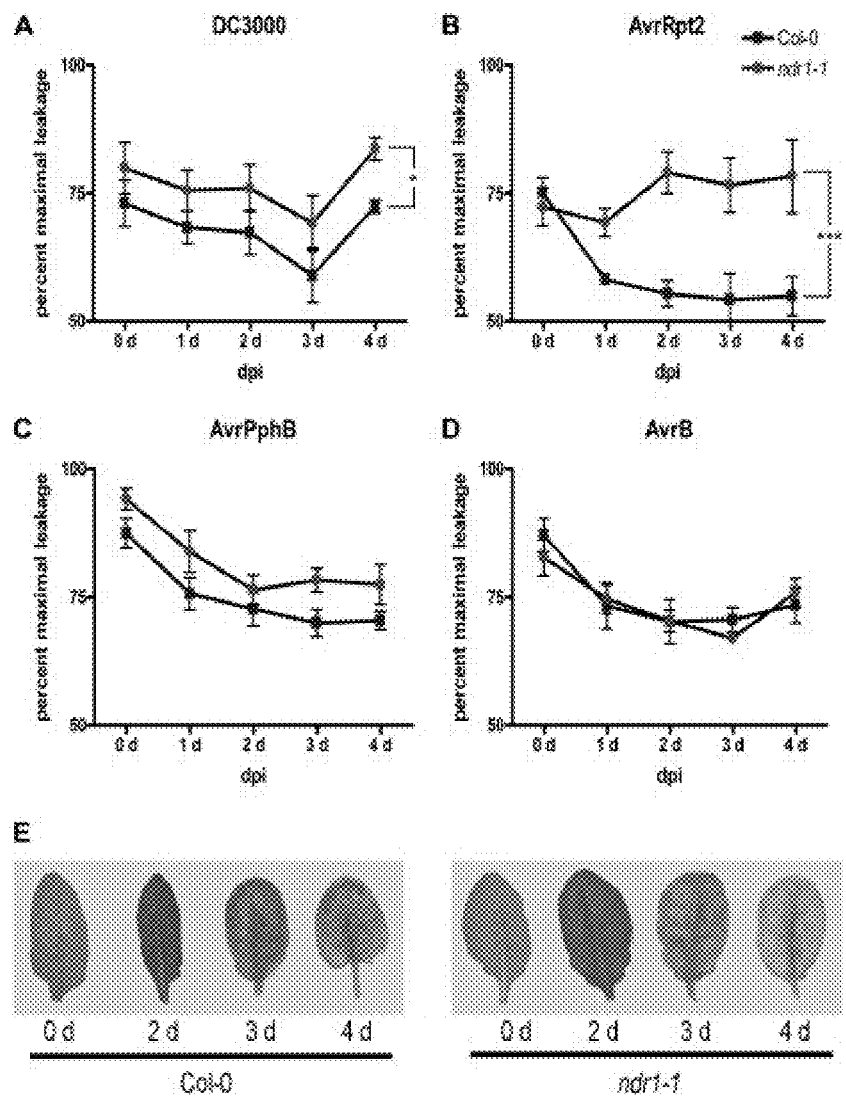
FIGS. 2A-2E are show graphs and photographs showing enhanced nutrient leakage in the ndr1-1 mutant following inoculation with Pst DC3000. Levels of electrolyte leakage from Col-0 and ndr1-1 plants in response to DC3000 inoculation are displayed as percent maximal leakage. Treatments include Pst DC3000 expressing (A) vector control, (B) AvrRpt2, (C) AvrB, (D) AvrPphB, and (E) photographs showing leakage observed in leaves in ndr1-1 as compared to Col-0 when inoculated with Pst DC3000 correlates with the onset of disease symptoms.

NDR1 Plays a Role in Limiting Electrolyte Leakage in Response to Pst DC3000 Infection ndr1-1 and ecotype Columbia (Col-0) plants were inoculated with the phytopathogenic bacterium Pst DC3000. In this case, ndr1-1 plants show altered electrolyte leakage compared with ecotype Columbia (Col-0) plants. While previous methods used to measure electrolyte leakage by simple conductance measurements over a relatively short time scale (e.g. 24 h), we chose to examine the changes in leakage in response to disease progression, and not simply in correlation to the hypersensitive response (HR), by utilizing a method previously applied to abiotic stress reported in Gilmour et al., 1988. When ndr1-1 plants were dip inoculated with Pst DC3000, the leakage measurements observed paralleled those of Col-0 (FIG. 2A). When plants were inoculated with Pst DC3000 expressing the Cys protease effector protein AvrRpt2 (Axtell et al., 2003), the difference in measured electrolytes between ndr1-1 and Col-0 were in greater contrast, with the most striking difference observed at 2 d postinoculation (FIG. 2B). This result provides evidence for an alteration in membrane integrity in the ndr1-1 mutant, as a simple increase in programmed cell death cannot explain the dramatic difference in leakage observed; ndr1-1 does not undergo HR in response to AvrRpt2 (Century et al., 1995). The large observed difference in leakage also correlates with the onset of disease symptoms in ndr1-1 (FIG. 2E). To this end, while ndr1-1 does not exhibit a significant increase in leakage, our findings would suggest that the ndr1-1 mutant is unable to restrict leakage induced following Pst DC3000-AvrRpt2 inoculation. This apparent loss in restricting leakage may be a primary mechanism through which AvrRpt2 is able to enhance susceptibility in ndr1-1. Pst DC3000 expressing the effector proteins AvrPphB (Shao et al., 2003) and AvrB (Mackey et al., 2002) did not elicit a statistically significant difference in the electrolyte release response in ndr1-1 plants compared with Col-0 (FIGS. 2, C and D).

See summaries of results in FIG. 2A to D, showing enhanced electrolyte leakage in the ndr1-1 mutant following inoculation with Pst DC3000. Levels of electrolyte leakage from Col-0 and ndr1-1 plants in response to Pst DC3000 inoculation are displayed as percentage maximal leakage. Treatments include Pst DC3000 expressing vector control (A), AvrRpt2 (B), AvrB (C), and AvrPphB (D). The dramatic increase in leakage observed in ndr1-1 as compared with Col-0 when inoculated with Pst DC3000 correlates with the onset of disease symptoms. Error bars display standard deviation from four technical replicates from two to three biological replicates. Significance was determined using two-way ANOVA, where asterisks represent statistically significant differences between Col-0 and ndr1-1: * P<0.05, *** P<0.001. E, Col-0 and ndr1-1 leaves at 0, 2, 3, and 4 d post-inoculation with Pst DC3000 expressing AvrRpt2.

Figure 3:
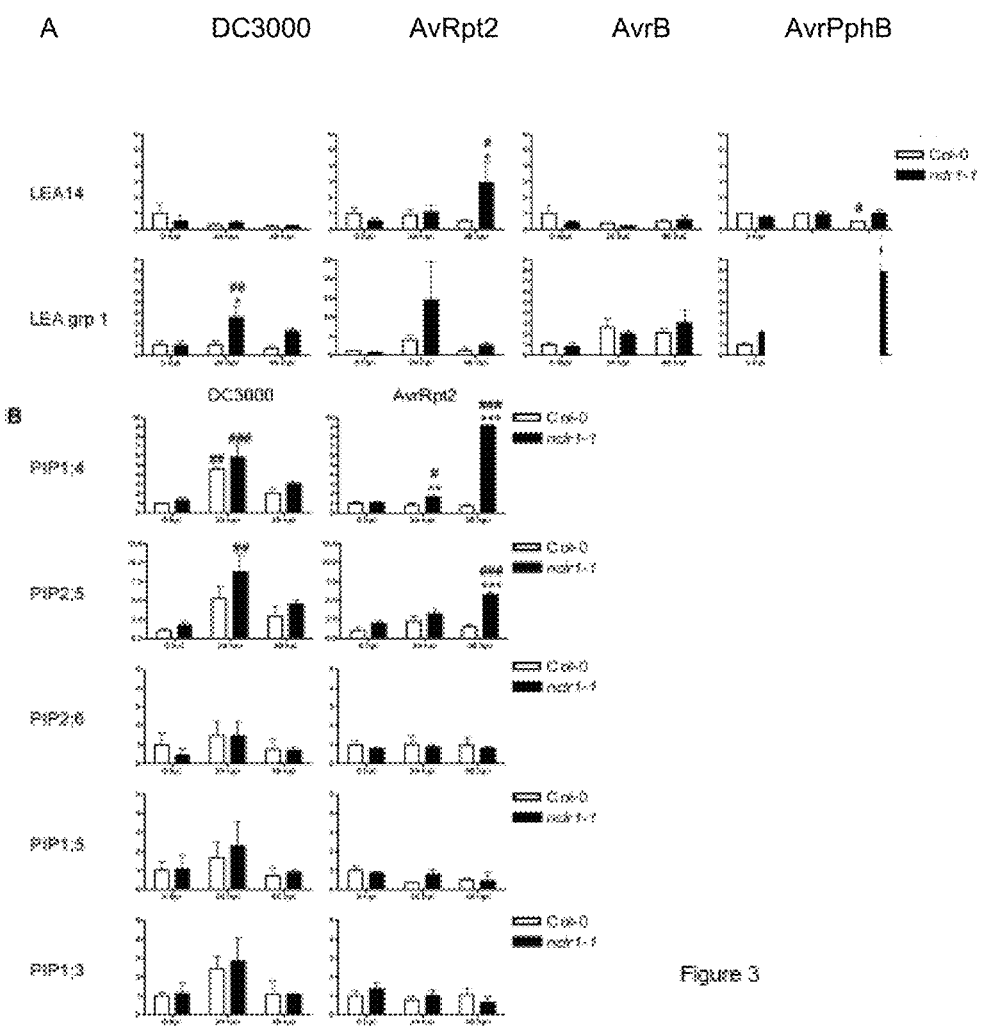
FIGS. 3A and 3B are graphs showing relative mRNA expression of biotic and abiotic responsive genes in ndr1-1 following Pst DC3000 inoculation. (A) Altered levels of expression in WT Col-0 and ndr1-1 mutant plants of LEA family genes in response to Pst DC3000 or Pst DC3000 expressing AvrRpt2, AvrB or AvrPphB. (B) Expression levels of aquaporin homologs known to be drought responsive in *Arabidopsis* when inoculated with Pst DC3000 or Pst expressing AvrRpt2.

The Ndr1-1 Mutant Displays Altered mRNA Expression of Several Biotic and Abiotic Stress-Responsive Genes Two members of the LEA family were investigated for altered mRNA expression in ndr1-1 mutant plants. LEA group 1 domain-containing protein (At1g32560) showed a nearly 3-fold increase in expression in ndr1-1 mutant plants as compared with Col-0 when inoculated with Pst DC3000 (FIG. 3A). LEA group 1 domain-containing protein also showed altered levels of expression in ndr1-1 plants when inoculated with Pst DC3000 expressing AvrRpt2, but when inoculated with Pst DC3000 expressing AvrPphB, a rapid induction was observed in ndr1-1, leading to a nearly 4-fold increase in mRNA expression at 48 h post-inoculation (hpi; FIG. 3A). The expression patterns of LEA14 were nearly identical between Col-0 and ndr1-1 under all conditions, with the exception of Pst DC3000 expressing AvrRpt2, which showed a nearly 3-fold increase in mRNA at 48 hpi in ndr1-1 plants (FIG. 3A). This differential expression in LEA family genes observed between Col-0 and ndr1-1 suggests an increase in cellular stresses occurring within an ndr1-1 cell following pathogen inoculation.

FIGS. 3A and 3B summarize the summarizing results of relative mRNA expression of biotic and abiotic responsive genes in ndr1-1 following Pst DC3000 inoculation. FIG. 3A shows altered levels of expression in wild-type Col-0 and ndr1-1 mutant plants of LEA family genes in response to Pst DC3000 or Pst DC3000 expressing AvrRpt2, AvrB, or AvrPphB. FIG. 3B shows expression levels of aquaporin homologs known to be drought responsive in Arabidopsis when inoculated with Pst DC3000 or Pst DC3000 expressing AvrRpt2. Error bars display standard deviation from one to two technical replicates from two biological replicates. Samples were taken at 0, 24, and 48 hpi. Expression is displayed as 0-h average fold for Col-0. Significance was determined using two-way ANOVA, where asterisks represent statistically significant differences between Col-0 and ndr1-1 and pound signs represent statistically significant changes over time: *, # P<0.05; , ## P<0.01; *, ### P <0.001.

Genes associated with water regulation and ion release (e.g. aquaporin homologs; AtPIP1;3, AtPIP1;4, AtPIP1;5, AtPIP2;5, and AtPIP2;6) were also examined. No significant differences in expression were observed between Col-0 and ndr1-1 at 0 hpi (FIG. 3B). However, two of the aquaporin homologs (AtPIP1;4 and AtPIP2;5) showed a rapid induction in ndr1-1 compared with Col-0 when infected with Pst DC3000 alone or expressing AvrRpt2 (FIG. 3B). This finding provides further evidence that NDR1 may play a role in mediating fluid loss, as AtPIP1;4 and AtPIP2;5 have been previously demonstrated to be up-regulated in response to drought. No significant differences in the aquaporin homologs tested between Col-0 and ndr1-1 following inoculation with Pst DC3000 expressing either AvrB or AvrPphB were observed. These data further suggest increased water stress within the cells of ndr1-1 plants following inoculation with Pst DC3000. Interestingly, we observed an increase in PDF1.2 mRNA expression at 24 hpi with Pst DC3000 expressing AvrB in the ndr1-1 mutant.

NDR1 Self-Associates in Planta Via the Formation of Oligomers

Figure 4:
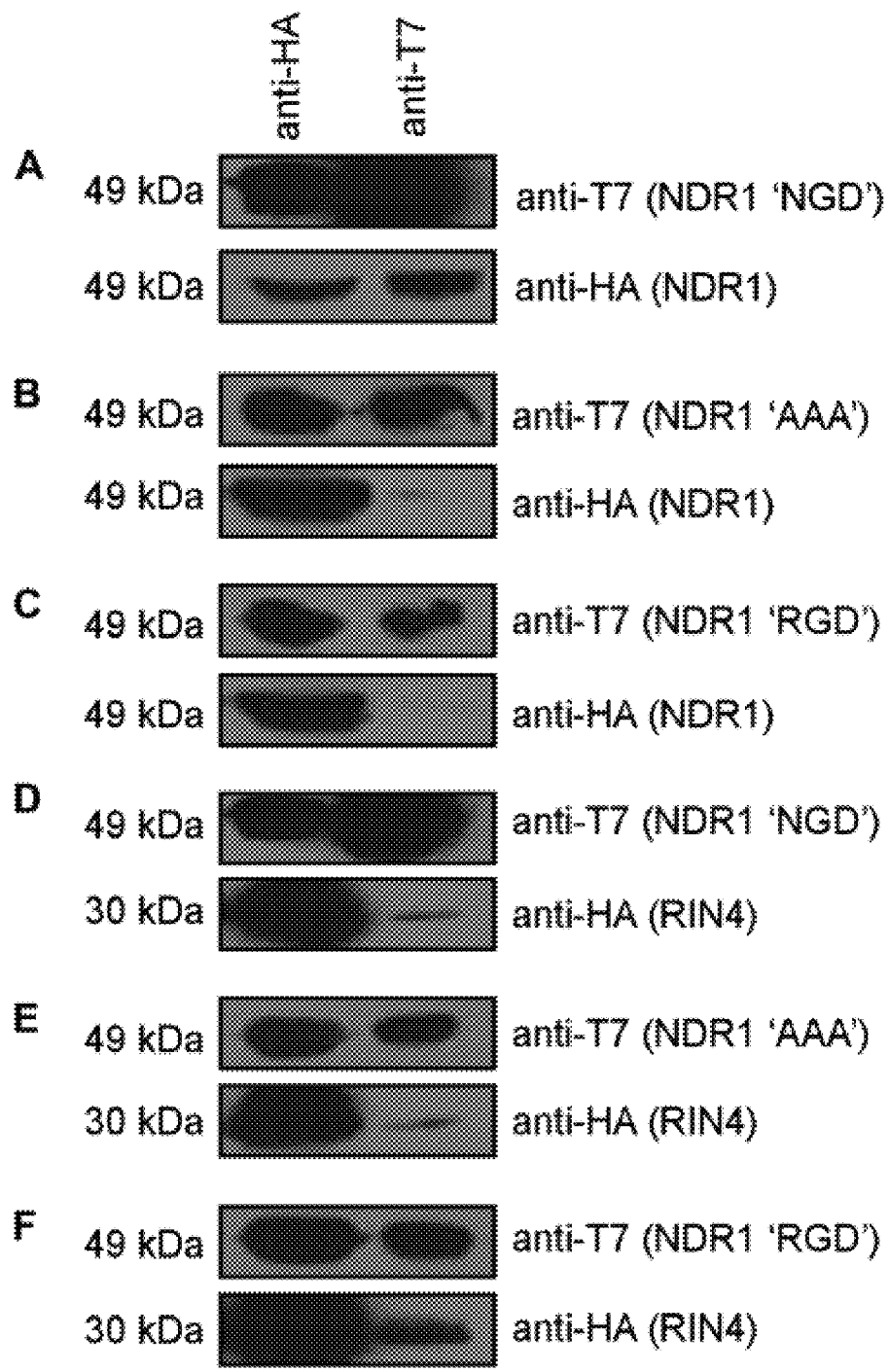
FIGS. 4A-4F show Western blots: (A) T7:NDR1 'NGD'-HA:NDR1, (B) T7:NDR1 'AAA'-HA:NDR1, (C) T7:NDR1 'RGD'-HA:NDR1, (D) T7:NDR1 'NGD'-HA:RIN4, (E) T7:NDR1 'AAA'-HA:RIN4, and (F) T7:NDR1 'RGD'-HA:RIN4.
Figure 5:
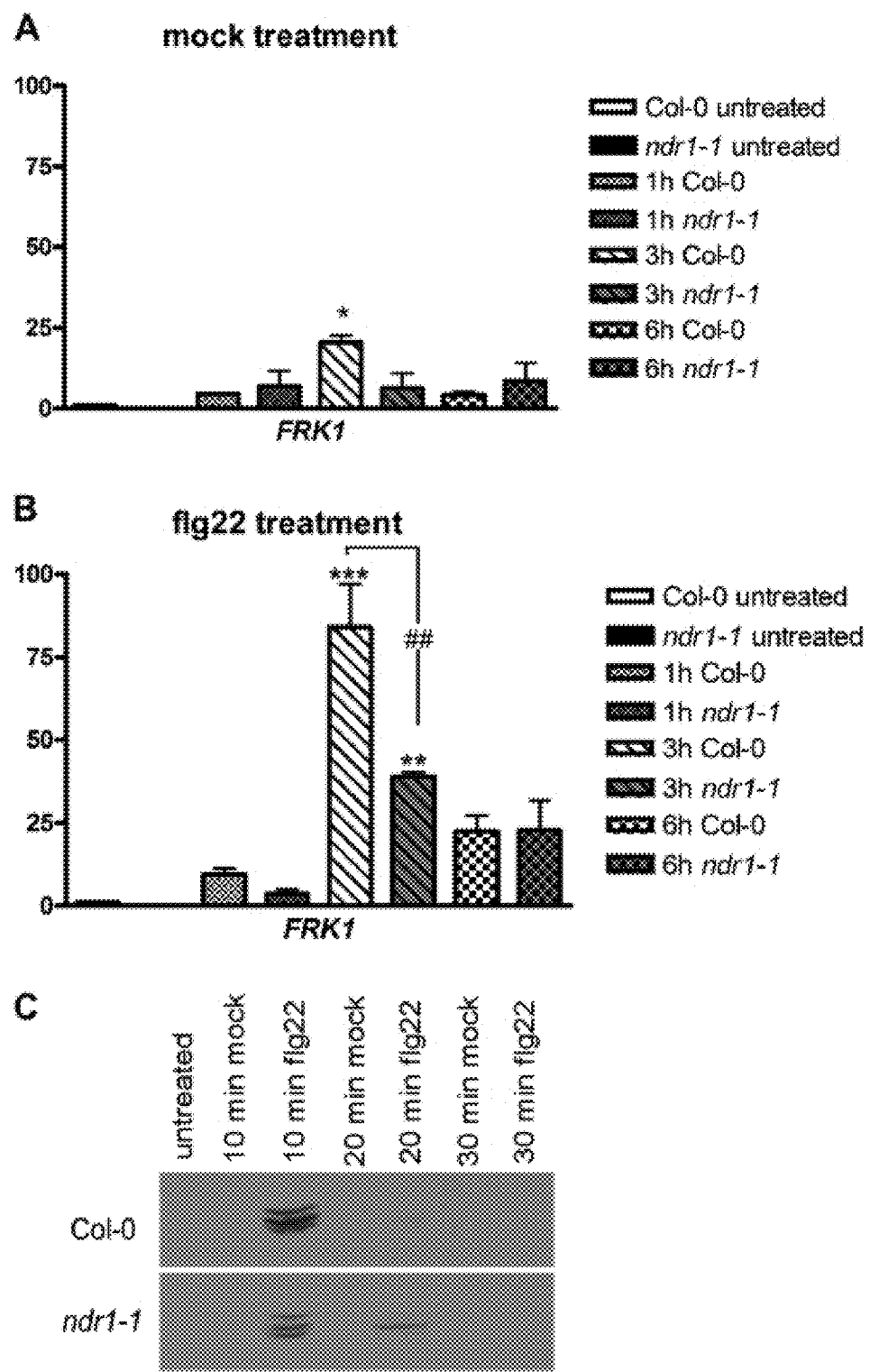
FIGS. 5A-5C are graphs showing expression levels of FRK1 mRNA analyzed by qRT-PCR in Col-0 and ndr1-1 mutant plants in response to (A) mock or (B) flg22 treatment and (C) a Western blot of MAPK3/6 in Col-0 and ndr1-1 mutant plants in response to flg22 or mock treatment.
Figure 6:
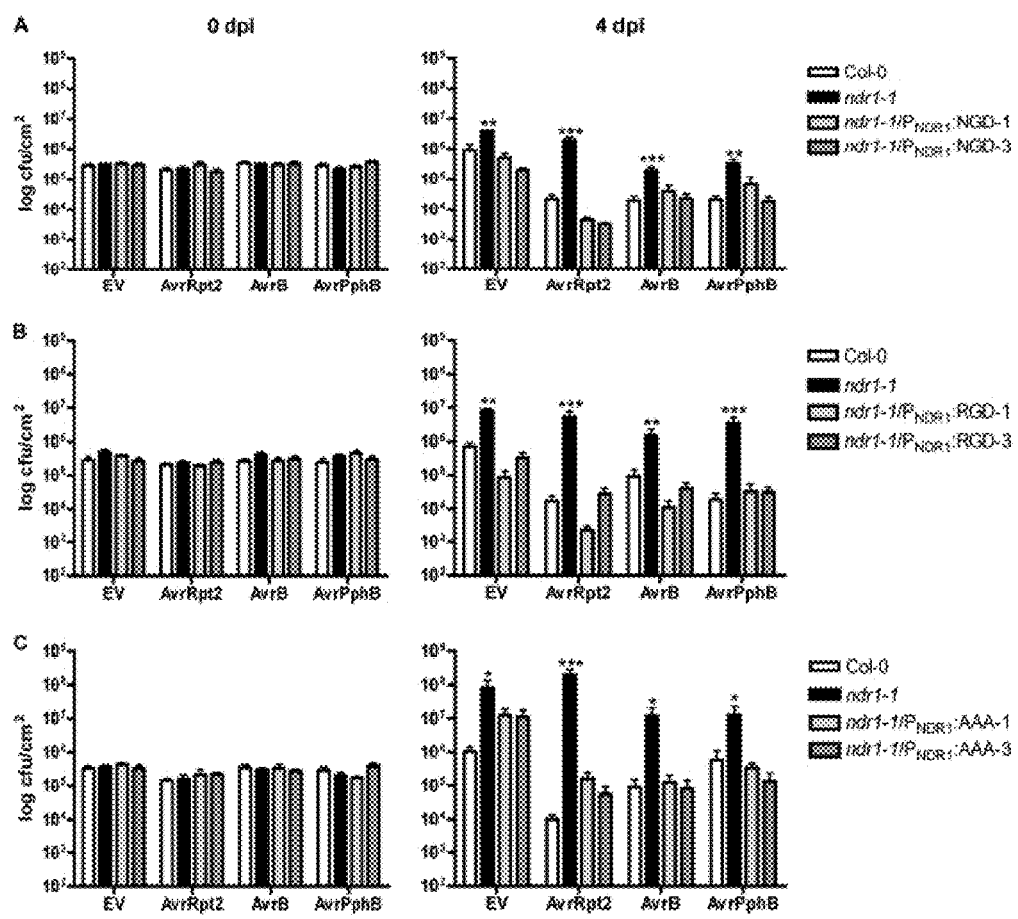
FIGS. 6A-6C are graphs showing growth of Pst DC3000 in *Arabidopsis* wild type and with alterations by mutations to the NGD site of NDR1.

To determine if NDR1 exists as multimers in planta, differentially epitope-tagged (e.g. T7 and hemagglutinin [HA] epitope) NDR1 constructs were expressed in Nicotiana benthamiana using Agrobacterium tumefaciens-mediated transient expression. As shown in FIG. 4A, using epitope-tagged NDR1 constructs, we detected a self-association in reciprocal coimmunoprecipitation pull downs, providing another example of integrin-like structure. The band intensity observed for the reciprocal self-associations correlated with differences in total tagged NDR1 protein detection rates.

FIGS. 4A-4F shows results that NDR1 associates with itself and RIN4 in planta, and this association is unaffected by mutations in the NGD site. Agrobacterium expressing HA:NDR1 or HA:RIN4, along with Agrobacterium expressing T7:NDR1 with substitutions in the NGD motif (wild type, NGD, RGD, or AAA), was infiltrated into N. benthamiana. Tagged proteins were immunoprecipitated from samples taken 48 h after infiltration using anti-HA (NDR1 or RIN4; right lane) or anti-T7 (NDR1; left lane) antibody. Proteins were detected by blotting with anti-T7 (top blot) or anti-HA (bottom blot) HRP-conjugated antibody. A, T7:NDR1 NGD-HA:NDR1. B, T7:NDR1 AAA-HA:NDR1. C, T7:NDR1 RGD-HA:NDR1. D, T7:NDR1 NGD-HA:RIN4. E, T7:NDR1 AAA-HA:RIN4. F, T7:NDR1 RGD-HA:RIN4.

ndr1-1 Mutant Plants Have Altered Cell Wall Adhesions

Figure 7:
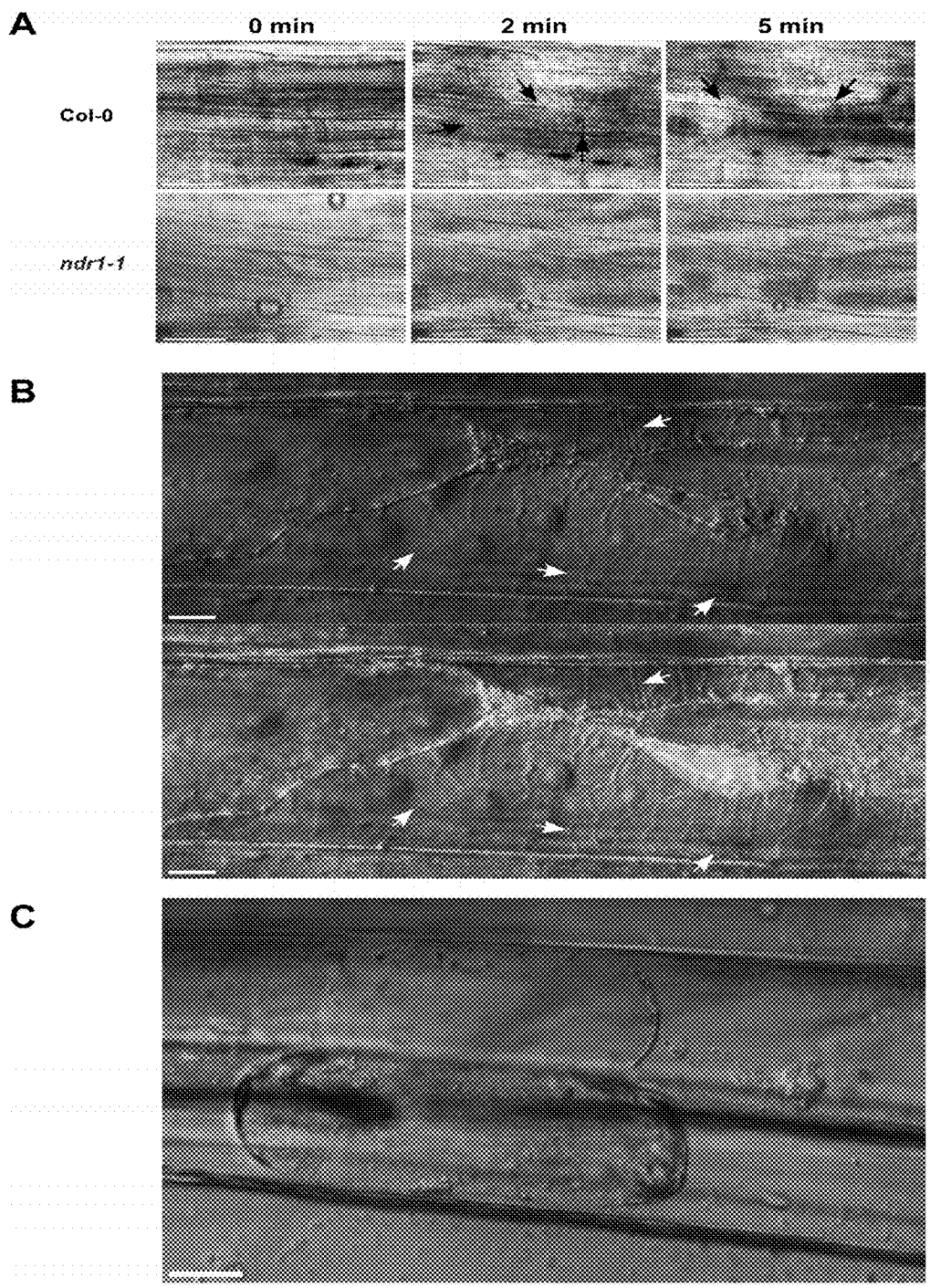
FIGS. 7A-7C are photographs showing ndr1-1 mutant plants exhibiting altered plasmolysis and plasma membrane-cell wall focal adhesions. (A) Time course (left to right: 0 (before), 2, and 5, min after treatment) of 8-day-old Col-0 or ndr1-1 CaCl$_2$-plasmolyzed hypocotyls. (B) Complemented ndr1-1 mutant line constitutively expressing a GFP:NDR1 protein exhibiting wild-type plasma membrane-cell wall adhesions (arrows). Differential interference contrast (DIC) (top panel) and confocal-DIC overlay (bottom panel) images of CaCl$_2$-induced plasmolysis. Arrows indicate Hechtian strand formation, illustrating significant physical linkages with the plasma membrane and cell wall. Scale bars=30 µm. (C) Hechtian strands are absent, or significantly reduced, in the ndr1-1 mutant plant. Scale bar=10 µm.

The role for NDR1 in the adhesion of the plasma membrane to the cell wall was tested by using 8-d-old ndr1-1 and Col-0 hypocotyls. These hypocotyls were visualized before and after $CaCl_2$-induced plasmolysis to assess the integrity of plasma membrane-cell wall adhesion. As shown in FIG. 7A, a distinctive concave shape was observed in the membranes of Col-0 hypocotyl cells undergoing plasmolysis, with obvious attachments to the cell wall still visible (FIG. 7A, arrows). $CaCl_2$-induced plasmolysis of the ndr1-1 mutant was significantly altered (FIGS. 7, A and C), resulting in the complete detachment of the plasma membrane from the cell wall, yielding spherical protoplasts with no remaining attachments (convex plasmolysis). Complementation of the ndr1-1 mutant with a constitutively expressed (i.e. 35S) GFP:NDR1 fusion protein restored the cell wall attachment phenotype to the wild type (FIG. 7B).

Figure 8:
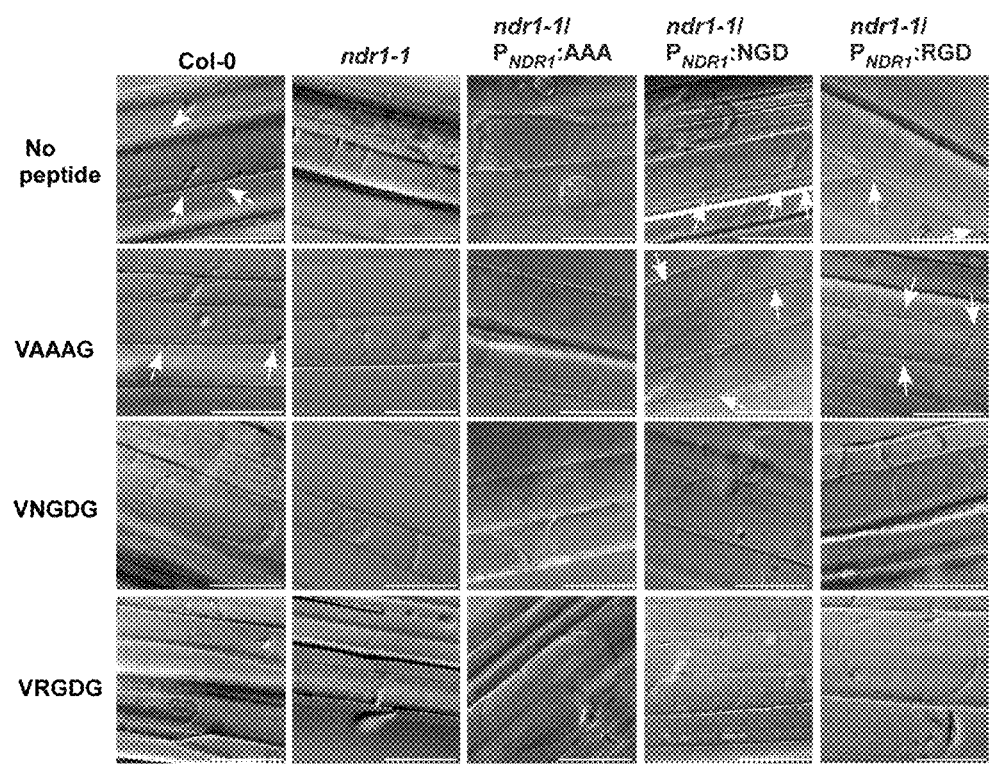
FIG. 8 shows application of exogenous peptides can alter the plasma membrane-cell wall adhesion in wild-type Col-0. Application of exogenous VNGDG or VRGDG peptide results in reduced plasma membrane-cell wall adhesions in Col-0, ndr1-1/PNDR1:NGD, and ndr1-1/PNDR1:RGD hypocotyl cells. Both ndr1-1 and ndr1-1/PNDR1:AAA hypocotyls are unaltered in adhesion phenotypes upon addition of purified VRGDG, VNGDG, and VAAAG peptides. Arrows indicate cell wall adhesion points. Differential interference contrast microscopy images were collected 5 min after the induction of plasmolysis. Bars=25 µm.

As shown in FIG. 8, addition of exogenous peptides did not alter the plasmolysis phenotype in ndr1-1 hypocotyls. Interestingly, the addition of the VNGDG peptide prior to the addition of $CaCl_2$ was able to alter the plasmolysis pattern of Col-0 hypocotyls from concave to convex in the same manner as the addition of the VRGDG peptide, suggesting that the NGD motif might function similarly to the RGD motif. In addition, complemented ndr1-1 lines expressing either PNDR1:NGD or PNDR1:RGD behaved similarly to Col-0 without peptide treatment as well as when treated with exogenous peptides. Conversely, PNDR1:AAA complemented lines responded in the same manner as ndr1-1 under both treatment conditions (FIG. 8), strengthening the case for the NGD motif functioning in adhesion in NDR1.

EXAMPLE 2

Relative Water Content, Water Loss Measurements, Seed Germination and Dormancy Assays in Col and Ndr1 Plants Material and Methods
Relative Water Content and Water Loss Measurements Arabidopsis thaliana Col-0 and ndr1 plants were grown in squared trays (weighed and adjusted for initial moisture content) during 4 weeks under standard watering conditions, in a growth chamber, at 20° C., with a 16 h/8 h light/dark cycle and a light intensity of 120 μmol photons $m^{-2}$ $s^{-1}$. After 4 weeks, the water content of the flats was adjusted to 100% (day 0) and plants were then subjected to 2 watering regimes: 1) control (C), where plants were watered three times weekly, and 2) drought stress (DS) conditions, where plants were not watered until the end of the experiment. Leaf samples were harvested at 0, 2, 6, 8, 10 and 12 days post drought stress (dps) and immediately frozen in liquid nitrogen and kept at −80° C.

We assayed two basic parameters related to water status in the leaves: 1) the relative water content (RWC %) and 2) electrolyte leakage.

RWC was measured in leaves from plants submitted to control and drought stress conditions as described: 4-8 leaves from 3-4 plants were harvest at 0, 2, 6, 8, 10 and 12 dps and immediately weighted to obtain the fresh weigh (FW). Next, the leaves were left to float on a covered Petri dish containing deionized water, during 24 hours, in the dark. The turgid weight (TW) of these leaves was then measured. Finally, the leaves were dried in an oven at 80° C., for 24 hours, taken out 15 minutes before the dry weight (DW) was measured. RWC was calculated according to the formula: RWC (%)=(TW)−(DW)/(FW)−(DW)×100.

Electrolyte leakage was performed as described below, with samples harvested at 0, 2, 4, 6, 8, 10 and 12 dps. In brief, a single leaf disc (0.7 cm diameter) was harvested from each plant. Four plants were used for each replicate. Leaf discs were quickly washed by submerging and gently swirling in sterile $dH_2O$ before being placed in a tube with 3 mL sterile $dH_2O$. Samples were rocked at 35 rpm for 3 h on an orbital shaker. After 3 h, the leaf disc was removed and the solution was measured using a conductance meter. The leaf discs were frozen for 1 h at −80° C., and then returned to the original tubes and rocked for an additional 3 hours before the disc is discarded and the final conductance measurement was taken. Readings were calculated as percent leakage of total (i.e. first reading—background/second reading) adjusted for background.

Seed Germination and Dormancy Assays

*Arabidopsis thaliana* Col-0 and ndr1-1 seeds were surface sterilized with 50% bleach and 0.1% Triton X-100 for 20 min, with shaking, and rinsed five times with sterile distilled water under horizontal laminar flow hood. Fifty seeds from each genotype, 100 seeds in total per plate, were sowed on petri dishes containing half-strength of Murashige and Skoog (MS) medium and different concentrations of ABA—0, 0.2, 0.5 and 0.1 μM. Plates were stratified at 4° C. for 4 days, in the dark, before being transferred to a growth chamber at 20° C., with a 12 h/12 h light/dark cycle and a light intensity of 120 μmol photons $m^{-2}$ $s^{-1}$.

During seed germination and dormancy assays, the radicle emergence was scored as germination and obvious cotyledons formation with green color was recorded as green cotyledons, respectively. The experiment was repeated five times, independently.

NRD1 is Required for Drought Tolerance

Both Col-0 and ndr1 lines demonstrated similar RWC and electrolyte leakage measurements over the course of the experiment, when soil moisture was maintained under control conditions. However, under drought stress conditions, differences in RWC was observed in a genotype-dependent manner (See Table 1). In Col-0 no changes in RWC were observed until day eight, but after this period, the RWC values in Col-0 fell to 47% and by day 12 Col-0 plants had lost all turgor pressure and were dead. The ndr1 mutant showed a decline in RWC beginning at day four. By day eight the RWC of ndr1 was reduced to 57%, and by day 11 the ndr1 mutant plants were dead.

These results were further supported by the observed electrolyte leakage patterns in the two lines measured. A dramatic spike in leakage was observed just before plants lose turgor pressure and could not be recovered from the drought stress. In ndr1 this sharp increase in electrolyte leakage was observed at day 10; in Col-0 a smaller increase also was observed at day 10 fitting nicely with the observed plant death for both lines; Col-0 at day 11 and ndr1 mutant at day 10. This finding further supports the hypothesis that NDR1 is involved in tolerance to drought stresses.

| | RWC (%) | |
|---|---|---|
| Dps | Col-0 | ndr1 |
| 0 | 81.52 ± 3.00 | 81.78 ± 5.28 |
| 2 | 79.03 ± 4.86 | 80.30 ± 3.07 |
| 4 | 79.42 ± 2.78 | 75.44 ± 3.69 |
| 6 | 80.87 ± 2.34 | 73.98 ± 6.50 |
| 8 | 71.18 ± 3.74 | 56.66 ± 10.49 ** |
| 10 | 46.64 ± 17.02 | 34.20 ± 4.85 ** |

Relative water content (RWC %) measured in leaves of *Arabidopsis* Col-0 and ndr1 plants, during drought stress treatment. Data shown are means±SD (n=6 to 8). Asterisks indicate significant differences determined by two way ANOVA test ( $P<0.01$). Dps, days post stress NDR1 Mutant Antagonizes ABA Suppression of Seed Germination Wild type Col-0 and ndr1 mutant were analyzed for seed germination, in response to different concentrations of ABA. The germination was scored by radical emergence and ndr1 mutant was found to be ABA-insensitive up to 0.5 μM, when compared with Col-0 plants. At this concentration, the germination rate decreased only to 90% in ndr1 while in Col-0, the decrease was statistically different (n=250; two way ANOVA test; *$P<0.001$), reaching 65%. At 1.0 μM of ABA, the germination rate was still statistically higher in ndr1 mutant (65%) than in wild type Col-0 (36%; n=250; two way ANOVA test; ***$P<0.001$).

ABA also controls seed dormancy. To address this issue, we followed the germination rate and the emergence of green cotyledons, during 14 days on MS medium plates amended with 1.0 μM of ABA. During the time course, the germination rate of ndr1 mutant was always statistically higher when compared with the wild type. This was also true for the assay measuring the emergence of green cotyledons. In all of these assays, ndr1 mutant performed much better than Col-0, with higher levels of tolerance to ABA, supported by a decreased seed dormancy.

EXAMPLE 3

Abiotic Stresses Screening of Col-0 and Ndr1 Plants Transformed with Pddndr1::GUS Construct Material and Methods Flowering Col-0 and ndr1 plants were transformed with *Agrobacterium tumefaciens* containing the native promoter of NDR1::GUS fusion constructs (pDDndr1::GUS lines). They were selected for homozygosity (Clough and Bent 1998), on MS media containing 1% Bacto agar and 50 μg $mL^{-1}$ kanamycin. Four homozygous lines from Co1/pDDndr1::GUS (labeled as 5, 6, 7, and 8) and ndr1/pDDndr1::GUS (labeled as 13, 14, 15 and 16) were grown in a growth chamber at 20° C. under a 12 hour/12 hour light/dark cycle and 60% of relative humidity. After four weeks, transgenic lines were submitted to different abiotic stresses, namely heat shock (i), cold (ii) and drought stress (iii) and wounding (iv; see method description below), and leaf samples were collected for histochemical GUS staining following standard protocols.

Heat Shock Treatment:

Col and ndr1 transgenic lines were incubated at 28° C. under ambient lights for two hours. As a control, a parallel set of transgenic plants were maintained in the original growth chamber, under non-stress conditions. At the end of the heat shock treatment, three leaves per three transgenic plants (n=9) from heat shock treated and control plants were harvested and immediately processed for GUS staining. The remained Col and ndr1 transgenic lines submitted to heat shock were placed back in the growth chamber and allowed to recover for three days. Leaf samples were also collected at this time.

Cold Stress:

Col and ndr1 transgenic lines were transferred to a growth chamber maintained at 4° C. for 24 hours with identical light conditions as described above. As a control, a parallel set of transgenic plants were maintained in the original growth chamber, under non-cold stress conditions. After 24 hours, 9 leaves were harvested for GUS staining, as described above. The remaining cold stress treated Col and ndr1 transgenic lines were returned to the original growth chamber for a 3-day recovering period. Leaf samples were collected following recovery.

Drought Stress:

Drought stress was performed according to standard protocols described in Harb et al, 2010. Before initiating drought conditions, plants were grown for four weeks. After 4 weeks, the water content of the flats was adjusted to 100% (1 g water $g^{-1}$ dry soil; Day 0) and plants were then subjected to 2 watering regimes: 1) control (C), where plants were watered three times weekly, and 2) drought stress (DS) conditions, where plants did not receive further watering. Leaf samples were harvested from each transgenic line, as well as from control plants for GUS histochemical staining purposes.

Wounding:

Col and ndr1 transgenic lines were wounded by making two small cuts with scissors. Control leaves for both Col and ndr1 were kept unwounded. Nine leaf samples from wounded and control transgenic plants were harvested at 0, 6, 12, 24, 48 and 72 hours after treatments and checked for GUS staining.

The GUS expression detected on leaf samples from Col (5, 6, 7, and 8) and ndr1 (13, 14, 15 and 16) transgenic lines submitted to heat shock, cold stress and wounding, did not show clear results when compared with their respective controls. Transgenic leaves from Col and ndr1 lines treated with cold showed a light GUS accumulation. For plants subjected to drought stress a reduction in the GUS staining was observed compared with transgenic controls in Col and ndr1 backgrounds.

EXAMPLE 4

Figure 10A:
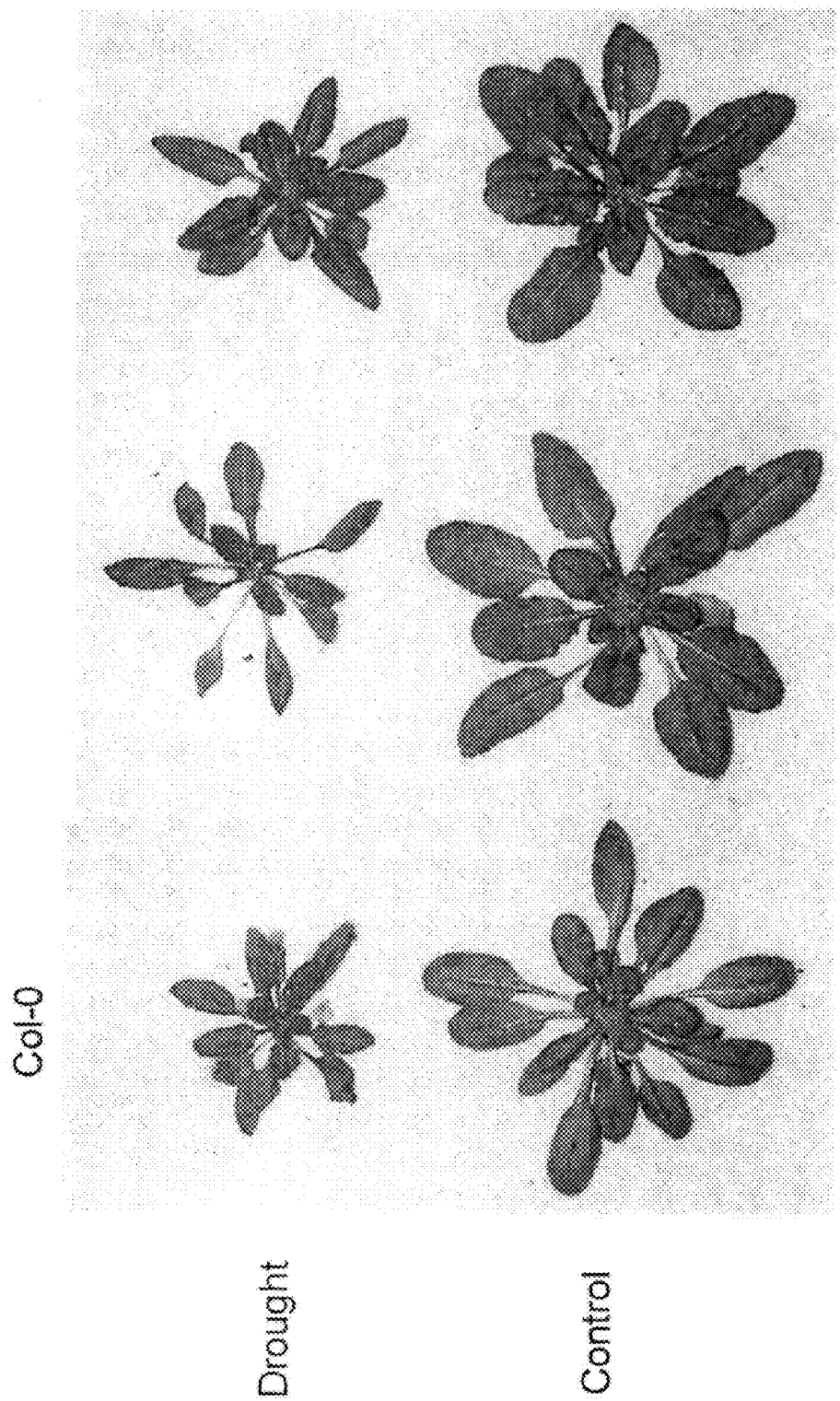
FIG. 10A-10C are (A) photographs of Col-0, ndr1-1 and 347 plants under control conditions and when exposed to drought; and (B-C) graphs showing relative water content (RWC) under (B) drought conditions and (C) control conditions.
Figure 10B:
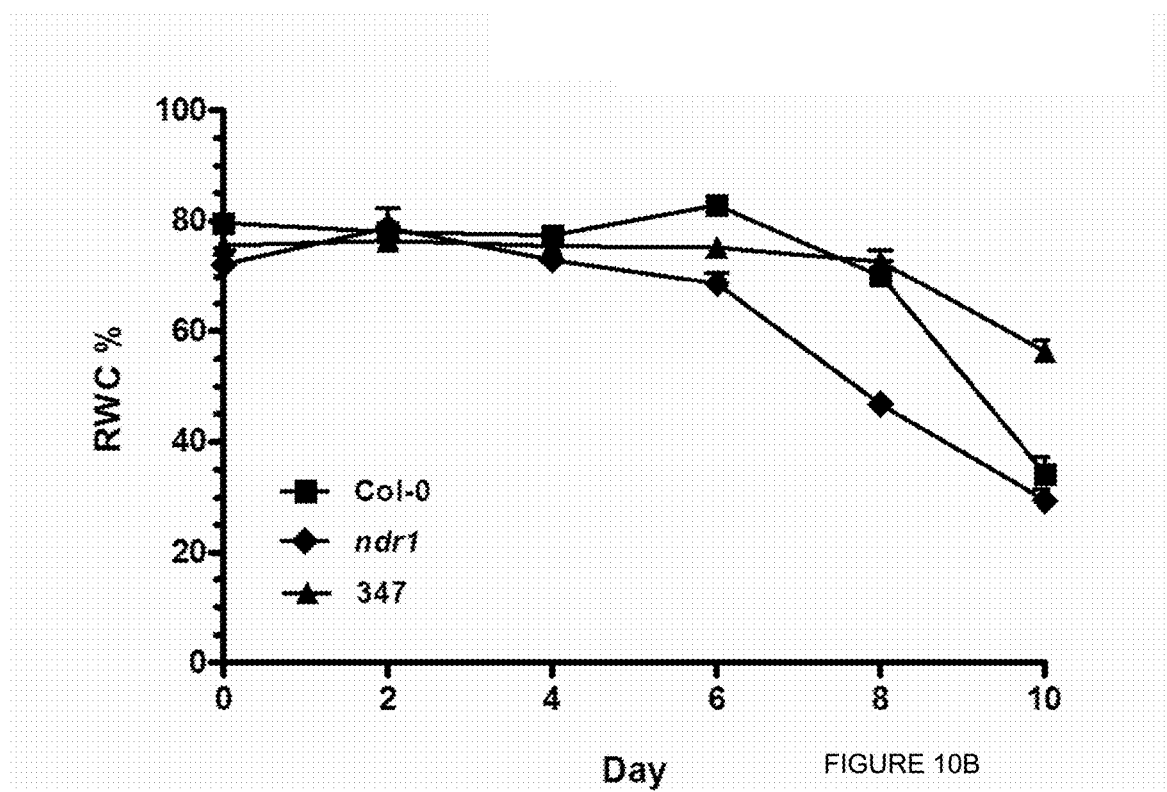
Figure 10C:
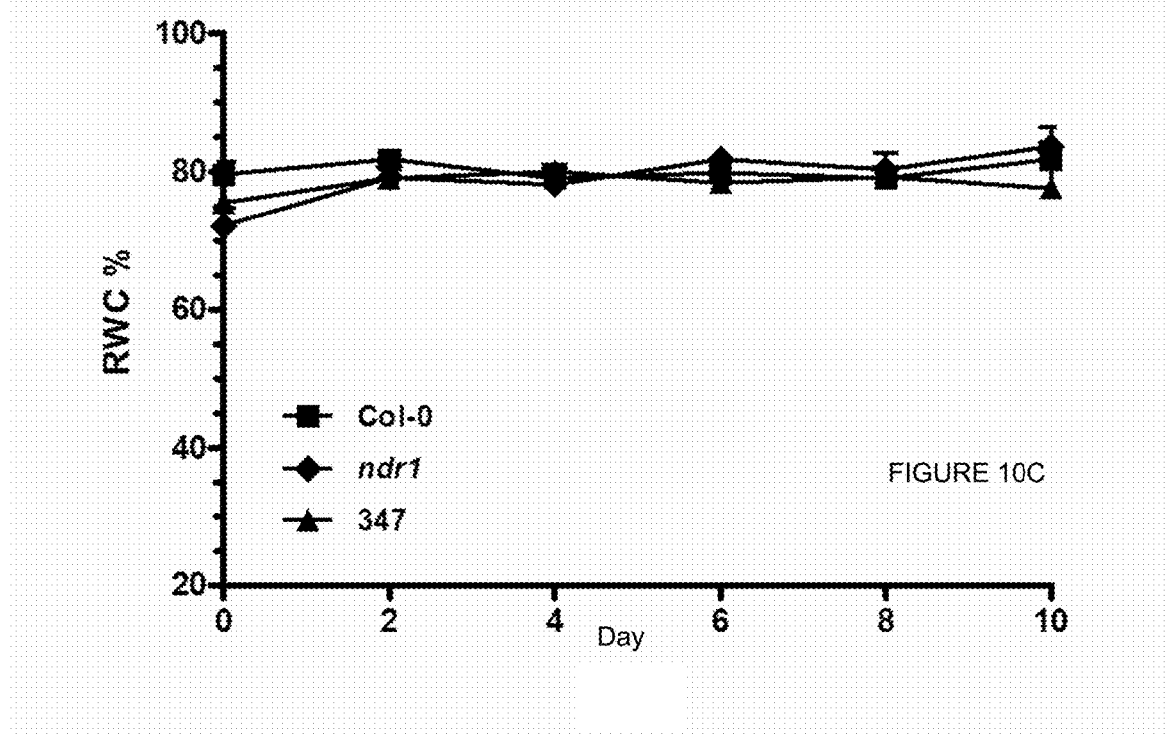

NDR1 over-expressor lines "347' (with 35S constitutive promoter driving the expression of the NDR1 coding sequence; published in Coppinger, J. P, Repetti, P., Day, B., Dahlbeck, D., Mehlert, A., and Staskawicz, B. (2004) "Overexpression of the plasma membrane-localized NDR1 protein results in enhanced bacterial disease resistance in *Arabidopsis thaliana*" *Plant J.* 40: 225-237) was analyzed for the ability to overcome drought stress. Lines of "347" were germinated as described above and subjected to drought (described above). As shown in FIGS. 10A-10C, an increased drought tolerance was observed, with a relative water content (RWC) of >50% being sustained to at least 12 day post-stress, compared with <40% RWC in wild-type *Arabidopsis* plants and the ndr1-1 mutant plant at 10 days post-drought.

EXAMPLE 5

Figure 11:
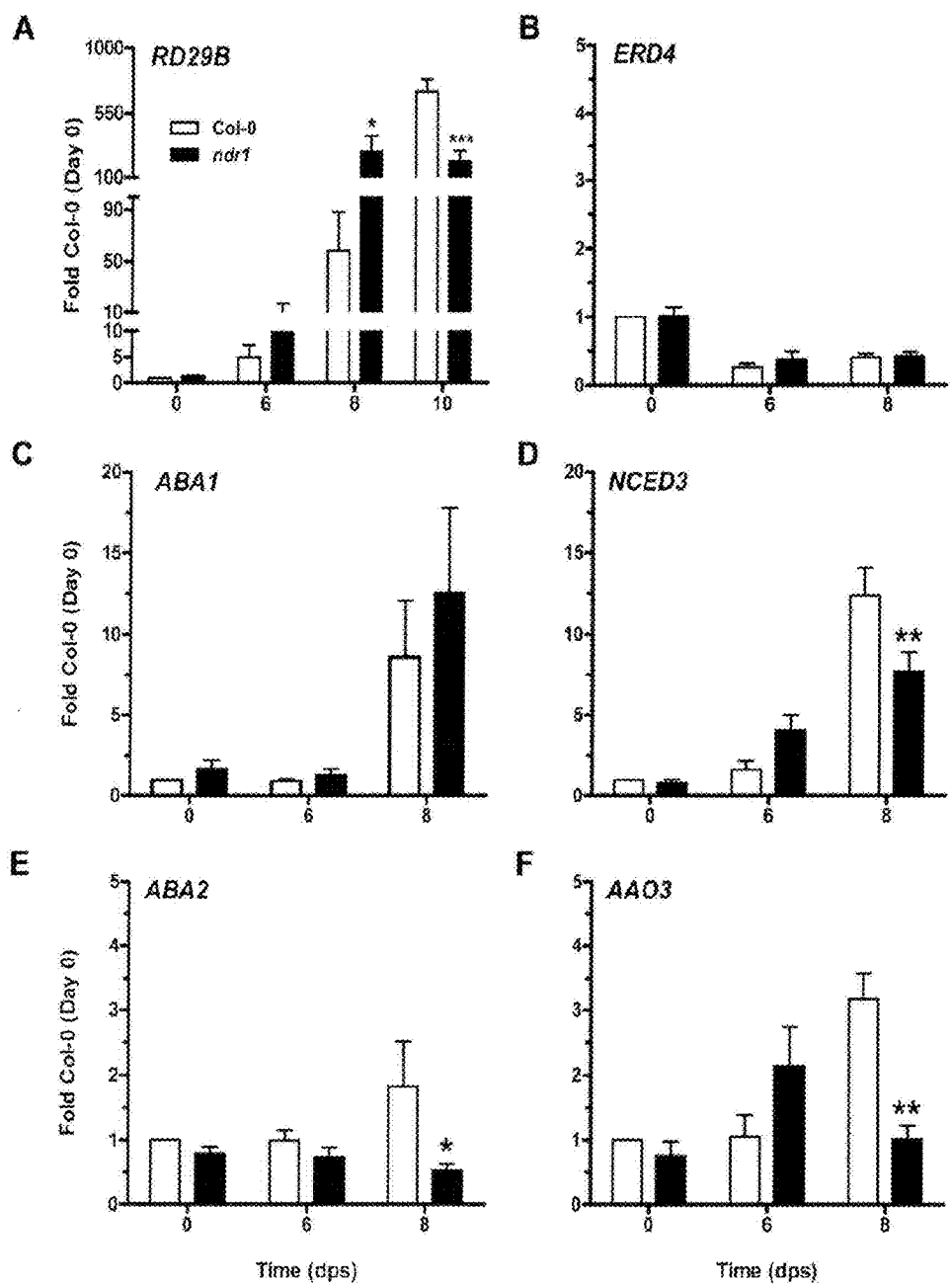
FIG. 11A-11F show expression levels of ABA-dependent and ABA-independent genes by qRT-PCT in Co2-0 and ndr1-1 in response to drought.

NDR1-Mediated Drought Stress Signaling is Regulated Through an ABA-Dependent Pathway An induction of a suite of genes associated with the activation of ABA-dependent drought stress was studied to see if ABA metabolism was altered in the ndr1 mutant. Analysis was performed using qRT-PCR utilizing two common marker genes for drought stress: the abscisic acid (ABA)-dependent responsive to desiccation gene, RD29B and the ABA-independent early responsive to dehydration gene, ERD4. As shown in FIG. 11A, the accumulation of RD29B mRNA at 8 dpi was significantly increased (P<0.001) in the ndr1-1 mutant as compared to WT Col-0. No differences were observed in mRNA expression of the ABA-independent drought marker ERD4 between genotypes FIG. 11B, confirming that NDR1-mediated drought stress signaling is regulated through an ABA-dependent pathway. See also FIG. 11C (ABA1), FIG. 11D (NCED3), FIG. 11E (ABA2) and FIG. 11F (AAO3).

EXAMPLE 6

ABA-Induced Stomata Closure is Abrogated in the NDR1 Mutant

Figure 12:
FIGS. 12A and 12B show stomata aperture size between mock-treated and ABA treated in Col-0 and ndr1-1 mutant. (A) is a graph of stomata aperture opening and (B) a photograph of the stomata aperture of ABA-treated Col-0 and ndr1-1 mutant.
Figure 1:
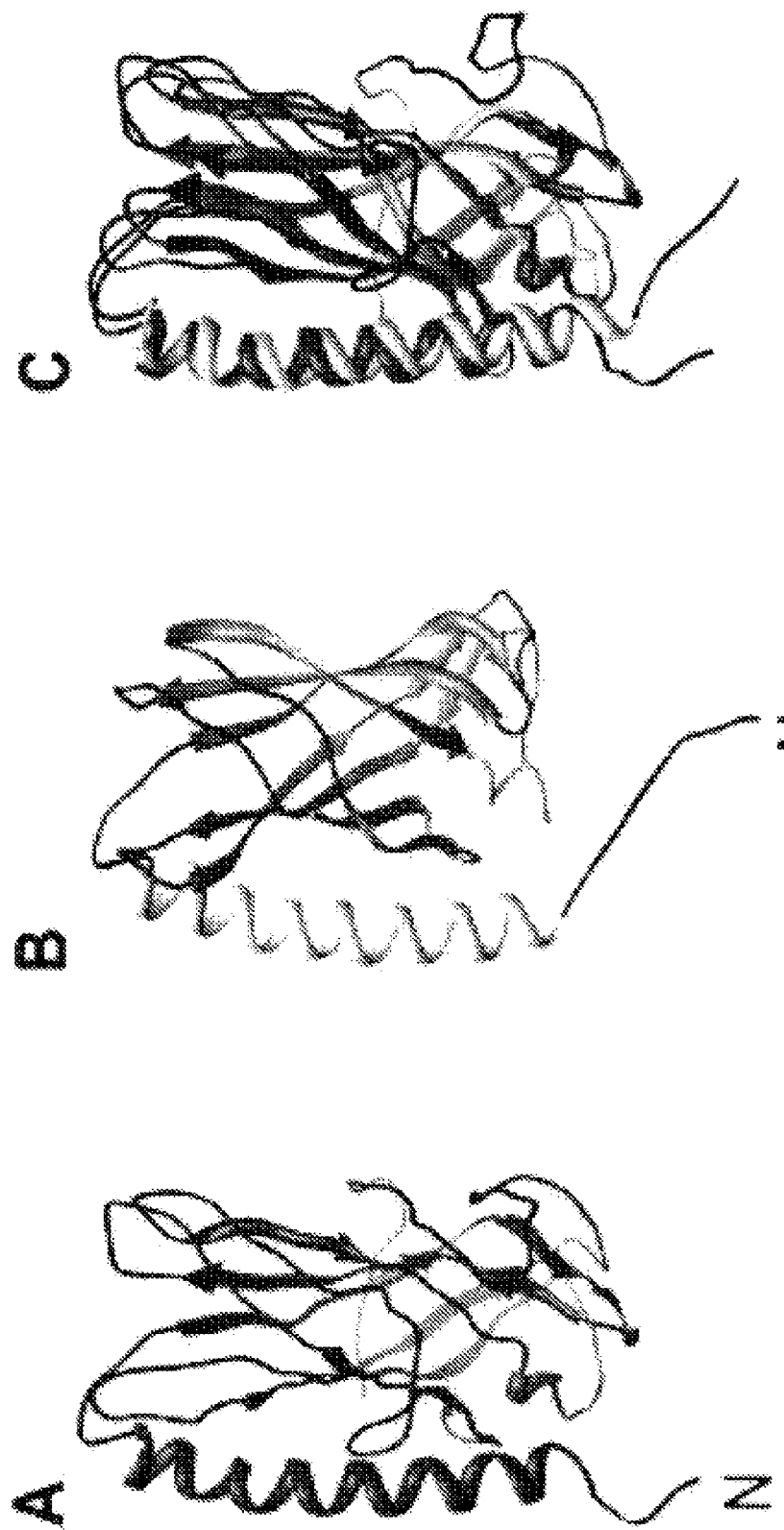
Figure 2:
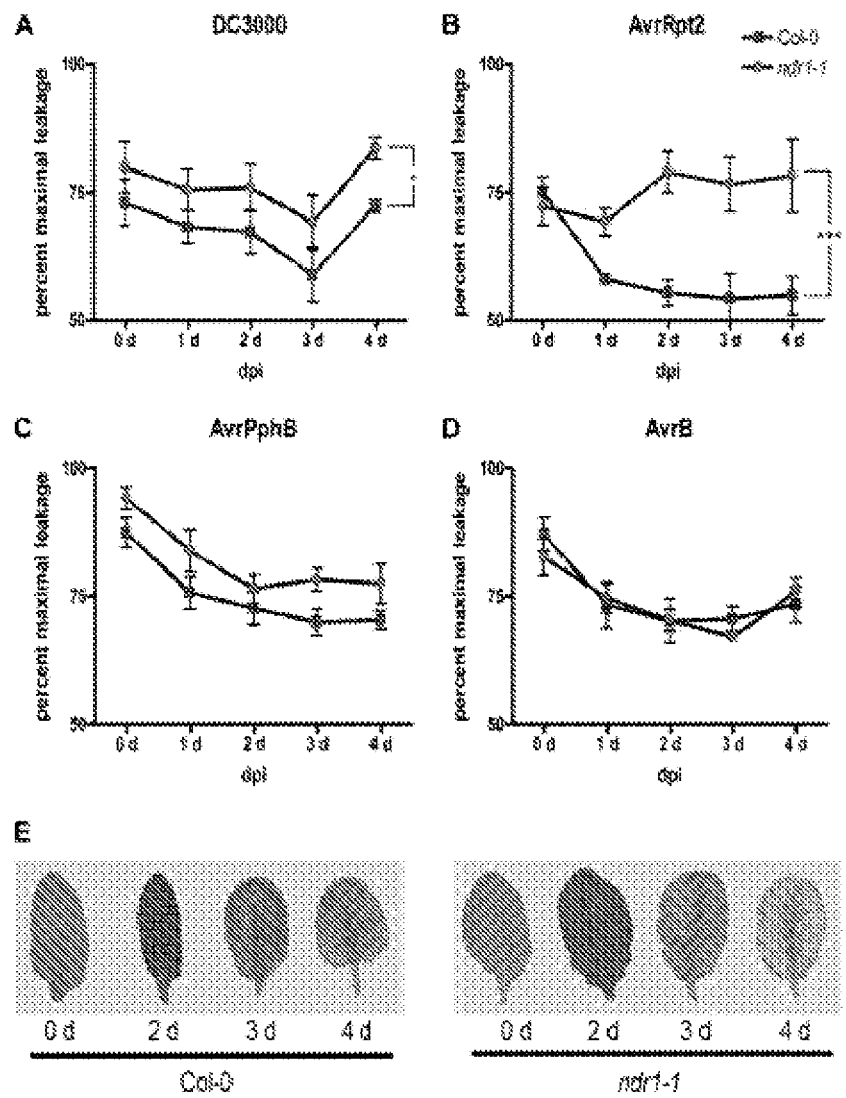
Figure 3:
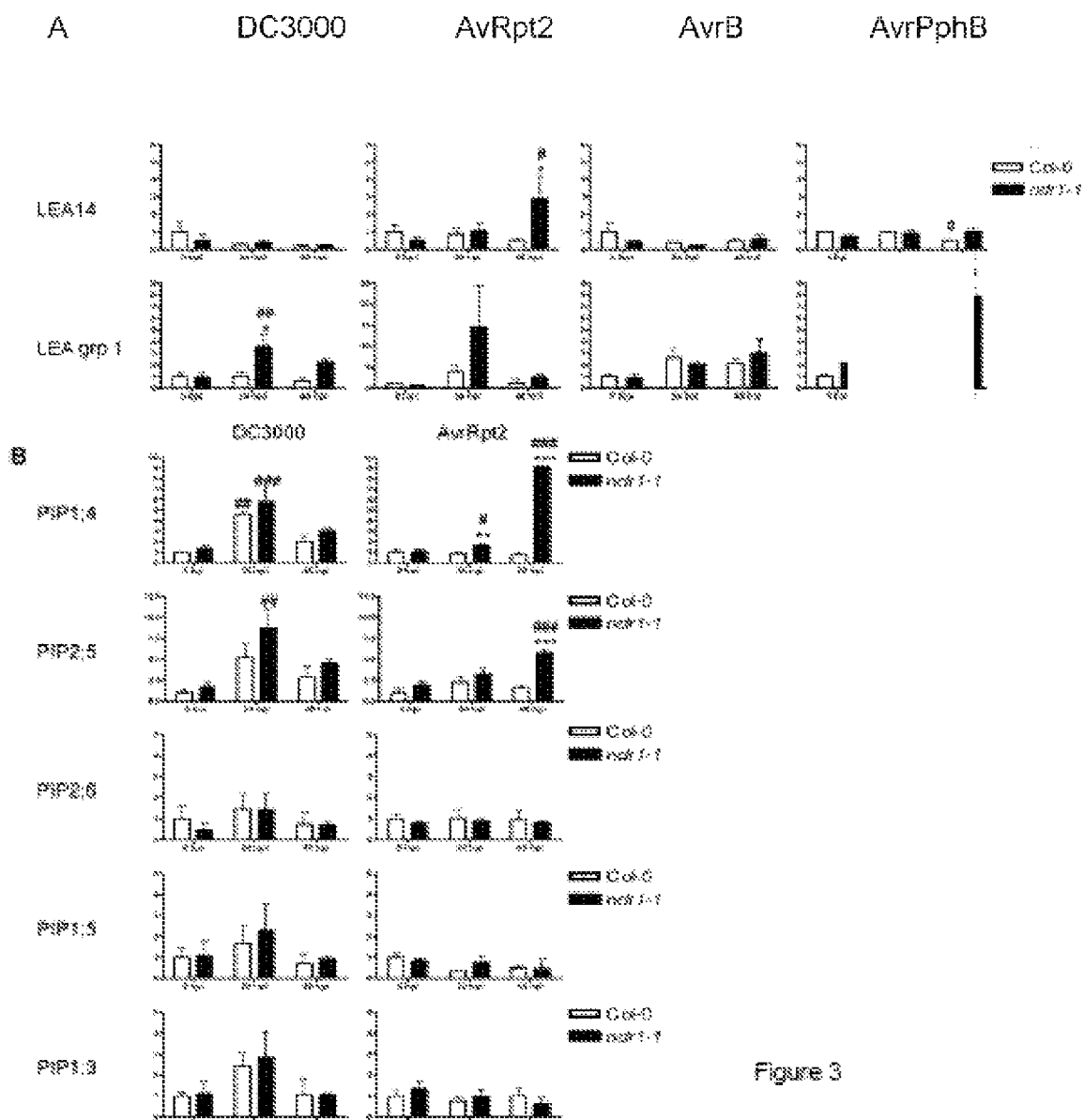
Figure 4:
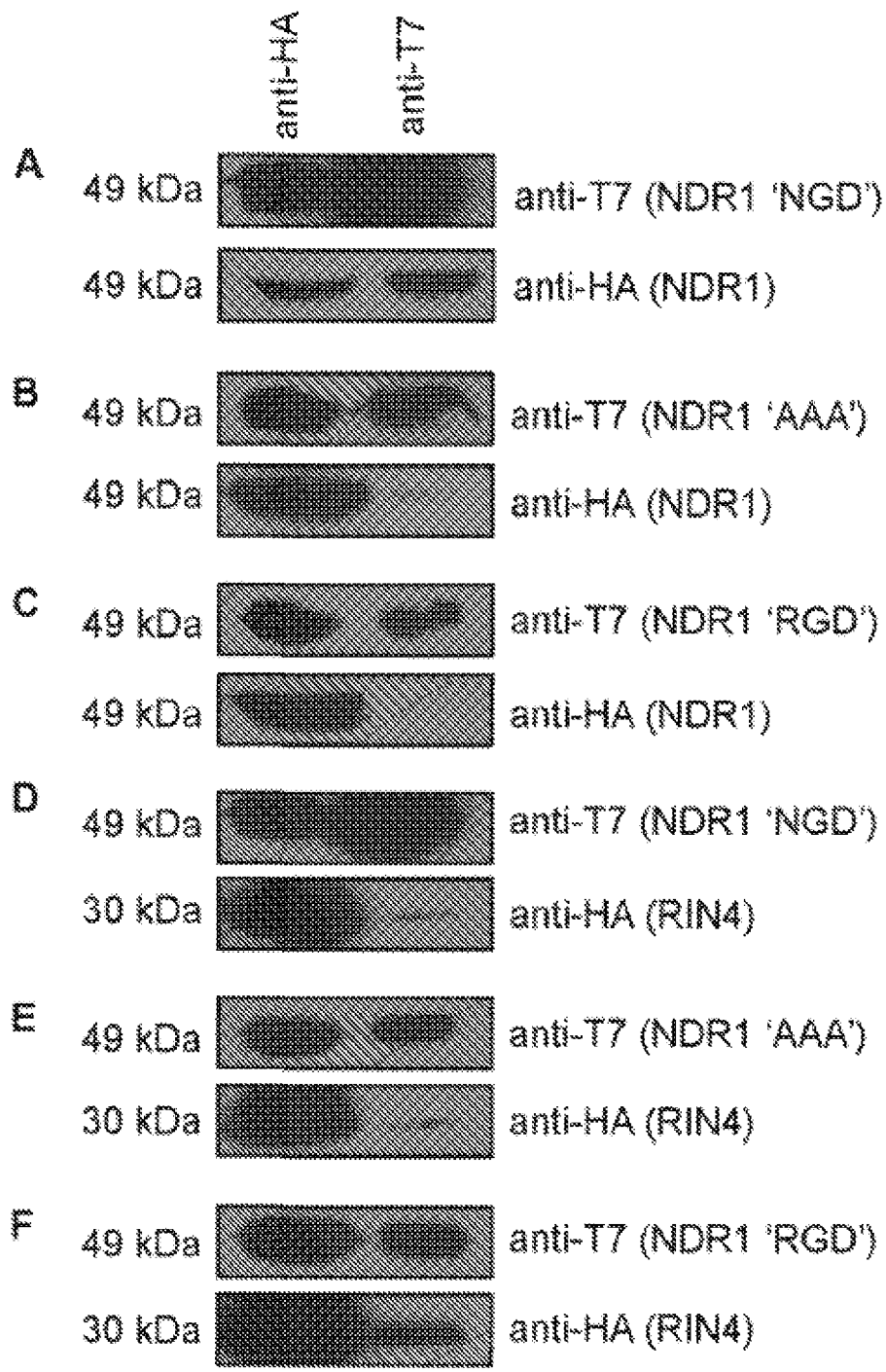
Figure 5:
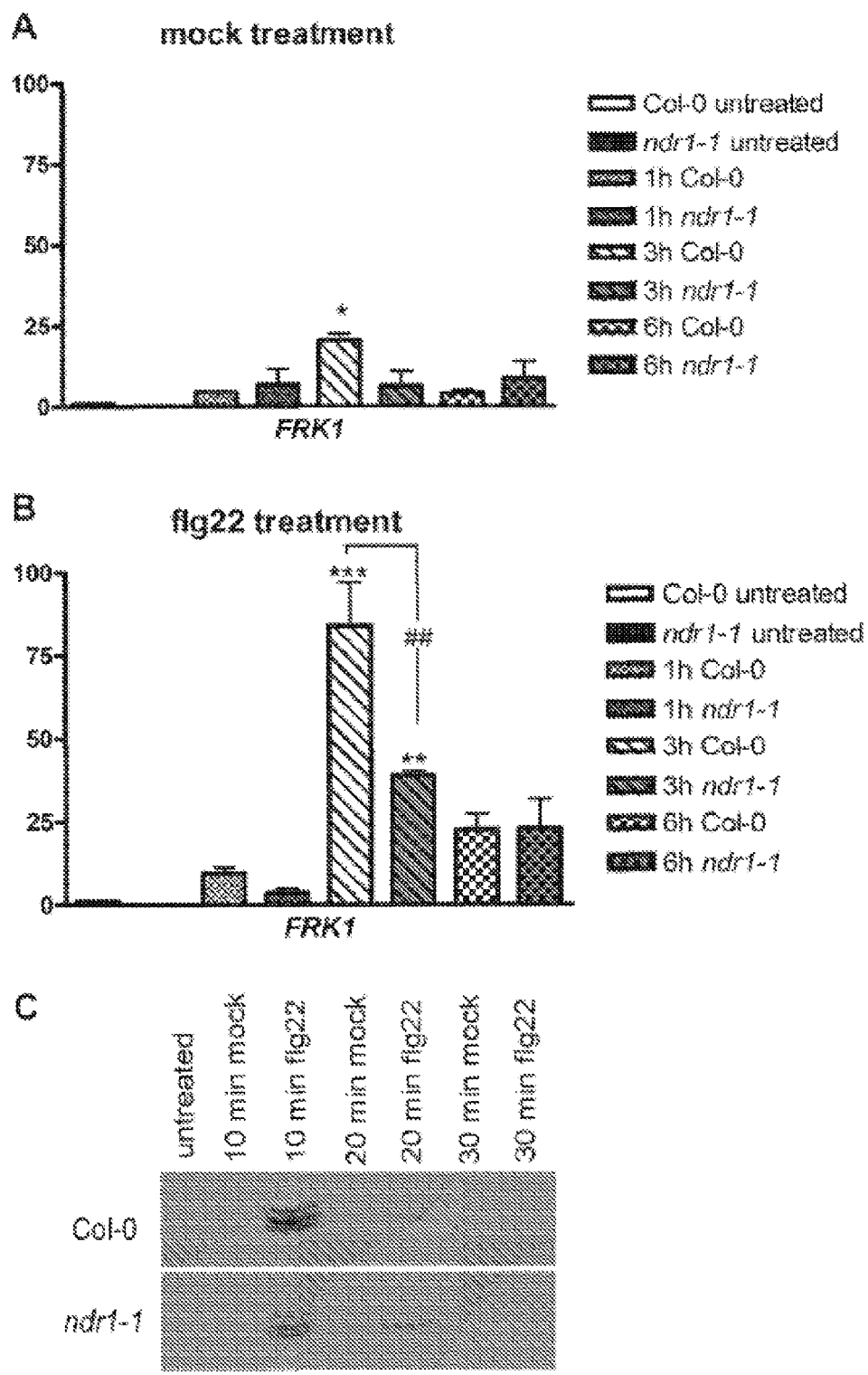
Figure 6:
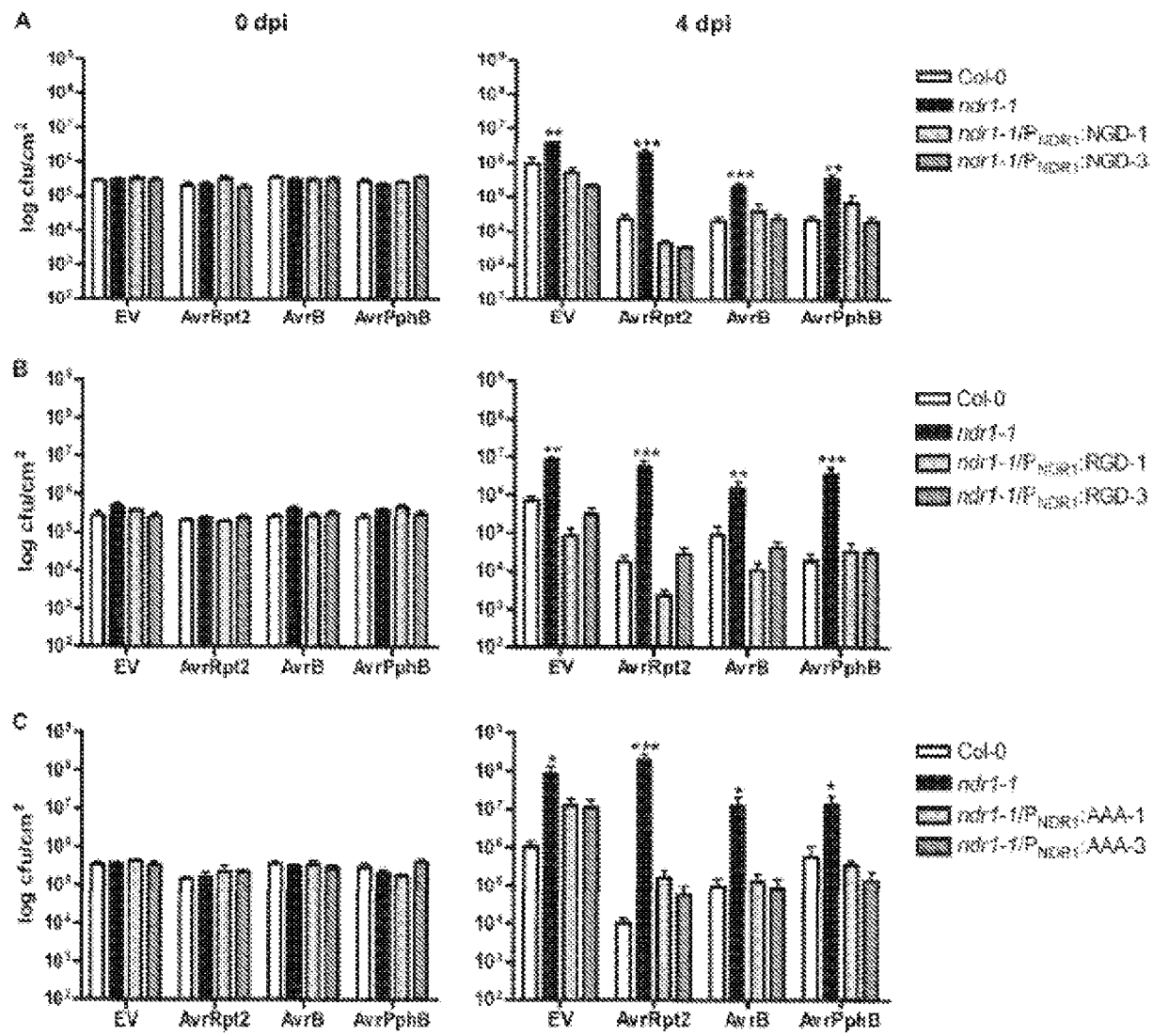
Figure 7:
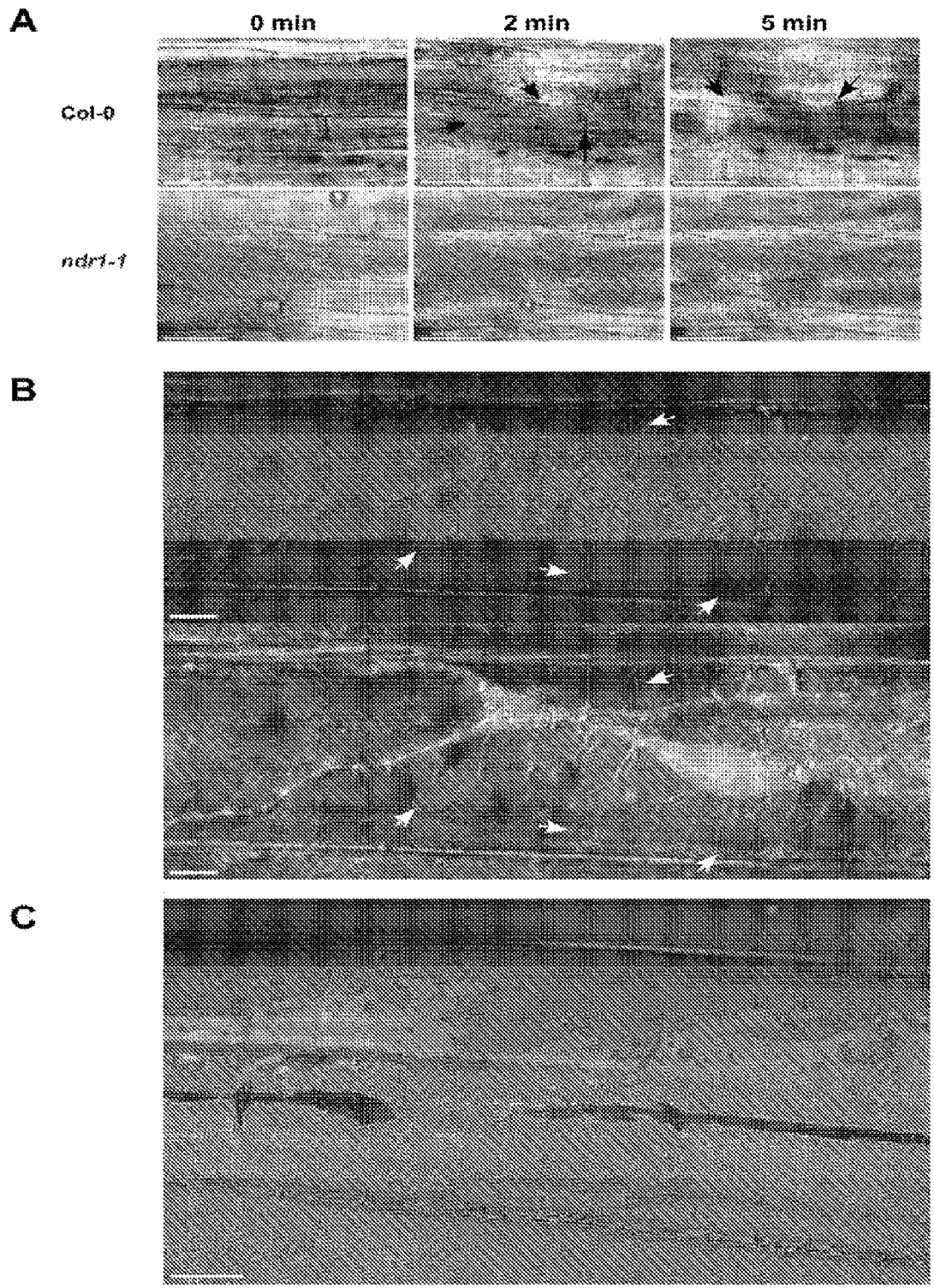
Figure 8:
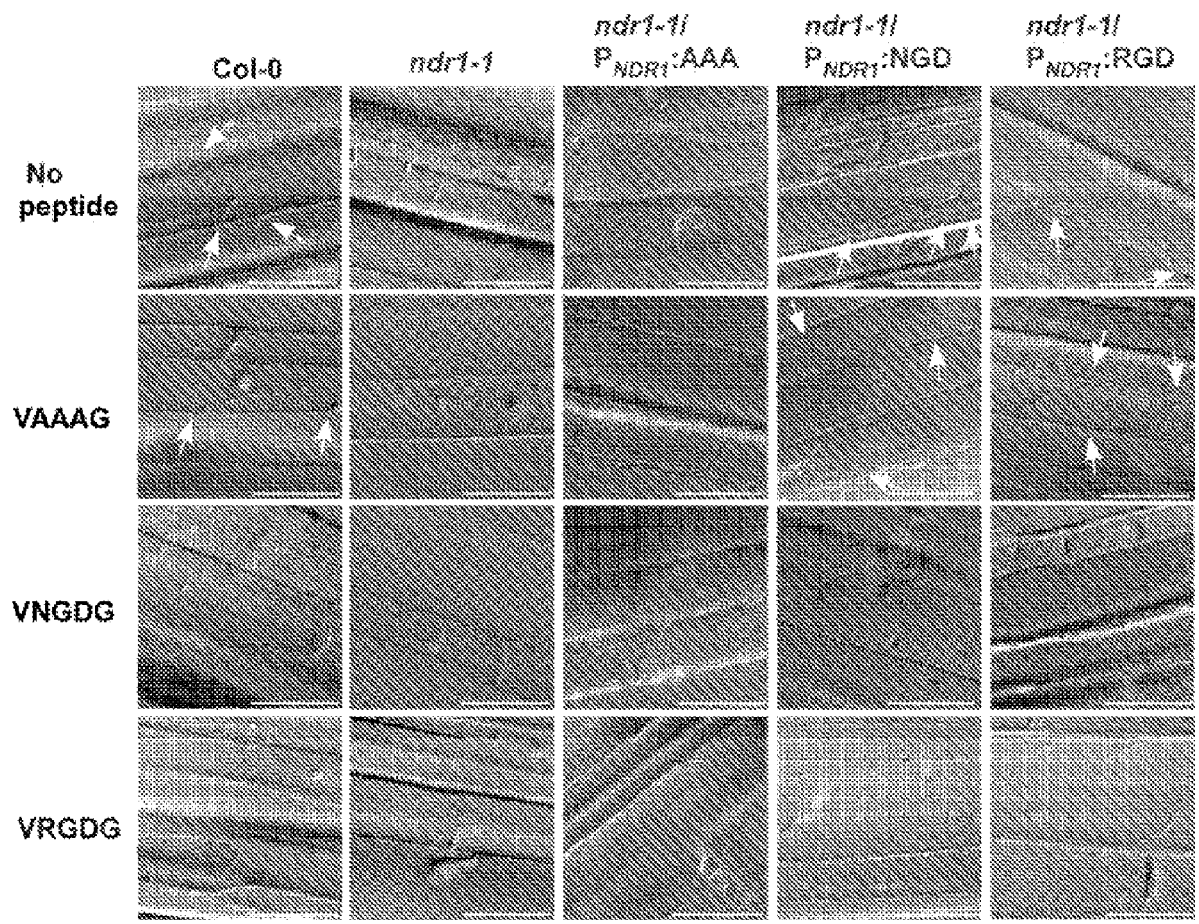
Figure 10A:
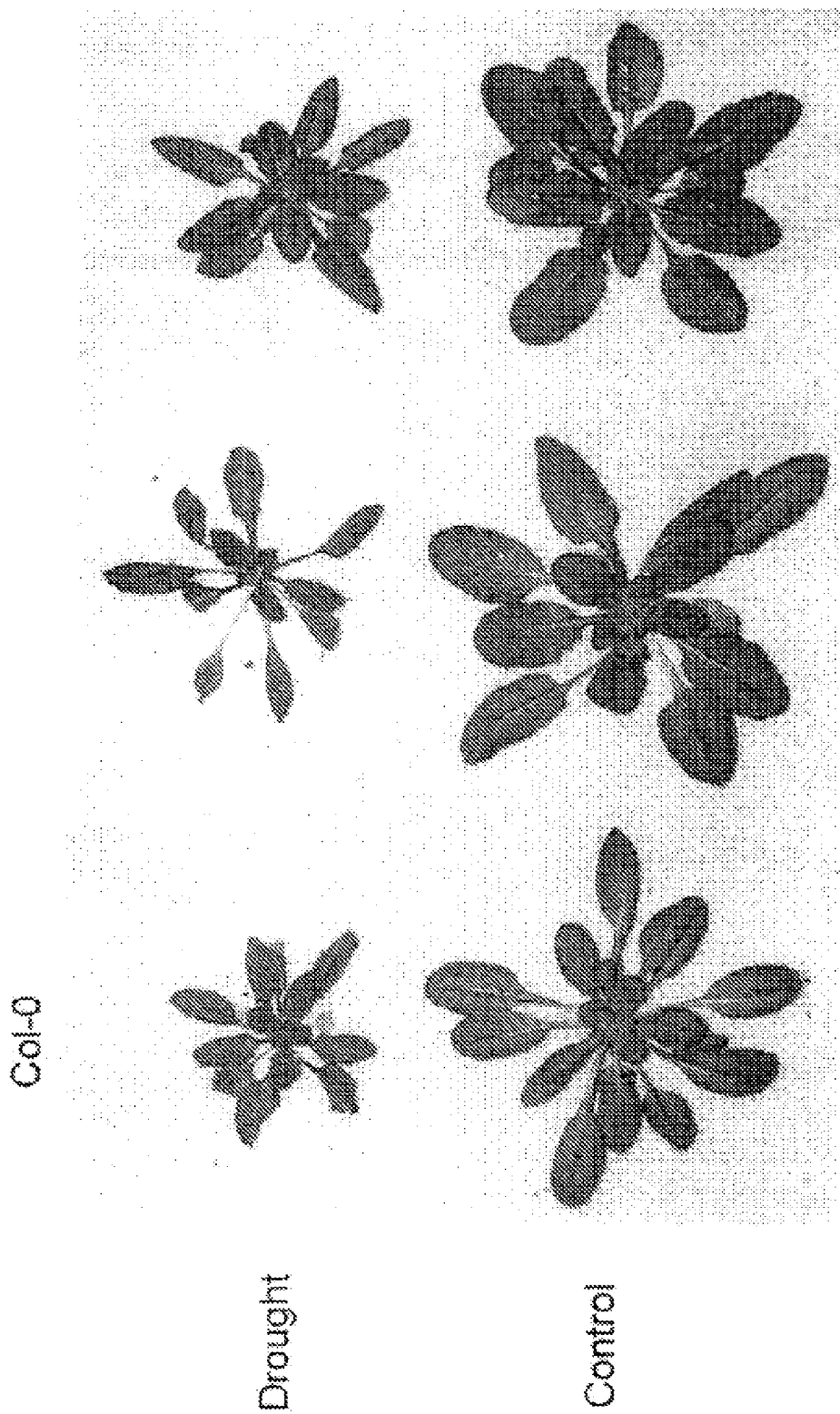
Figure 10B:
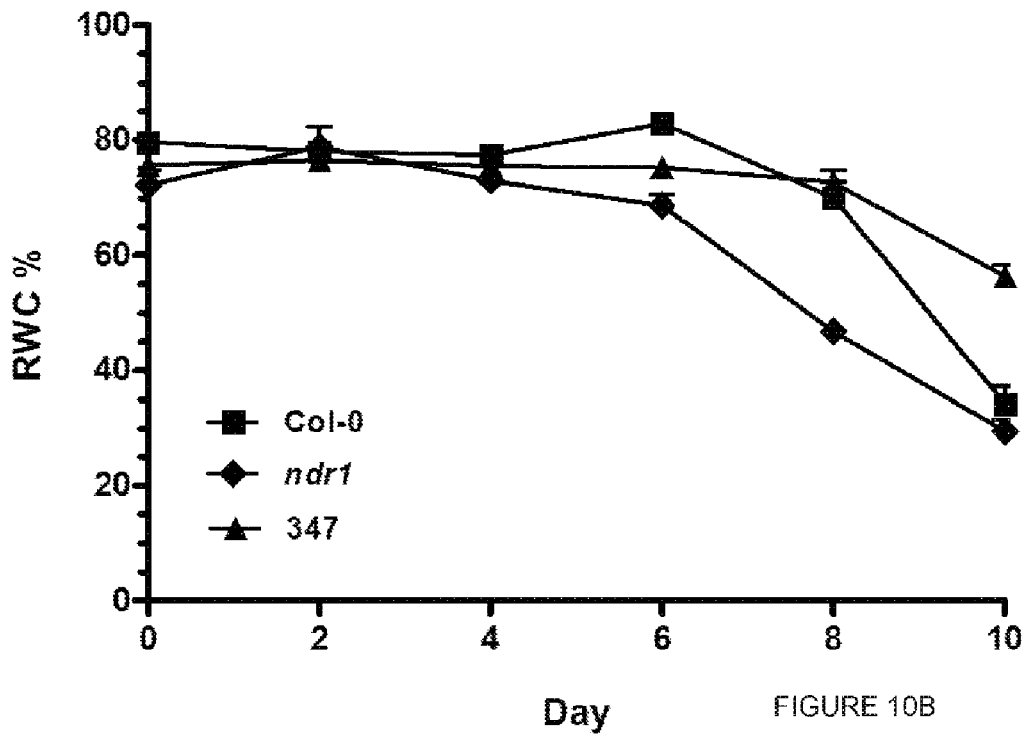
Figure 10C:
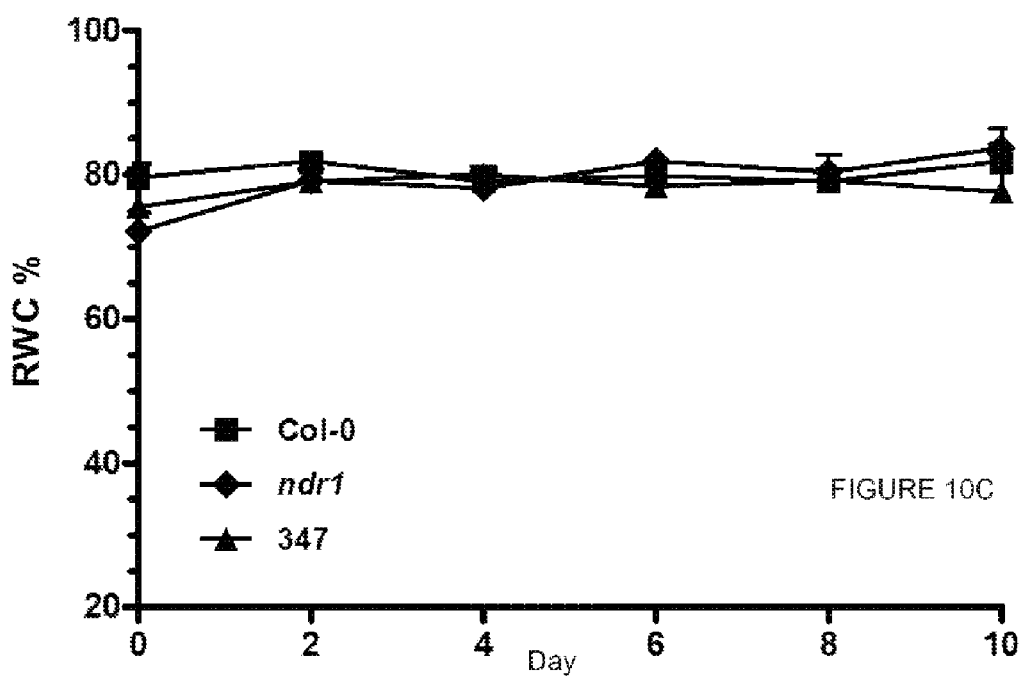
Figure 11:
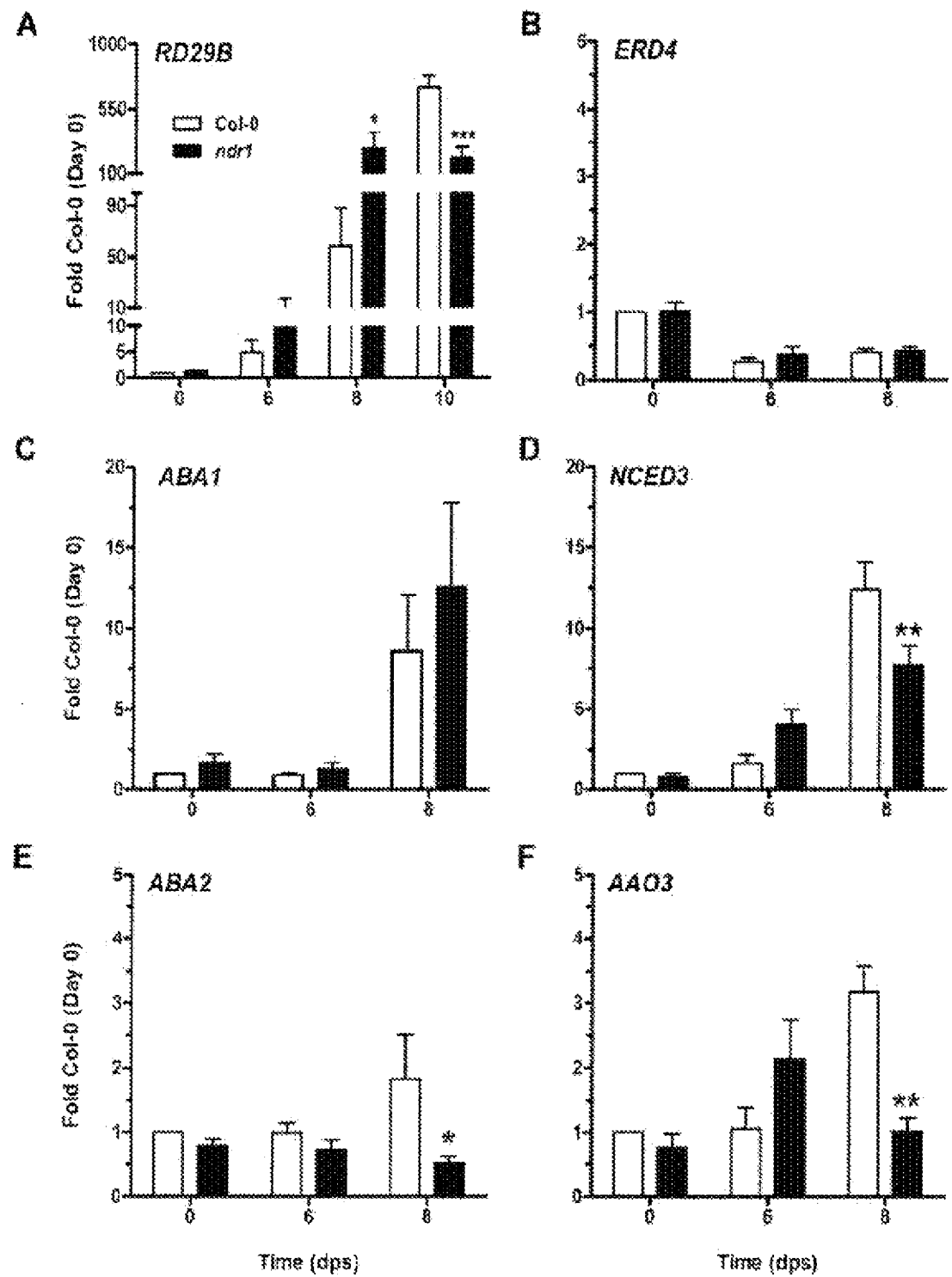
Figure 12:
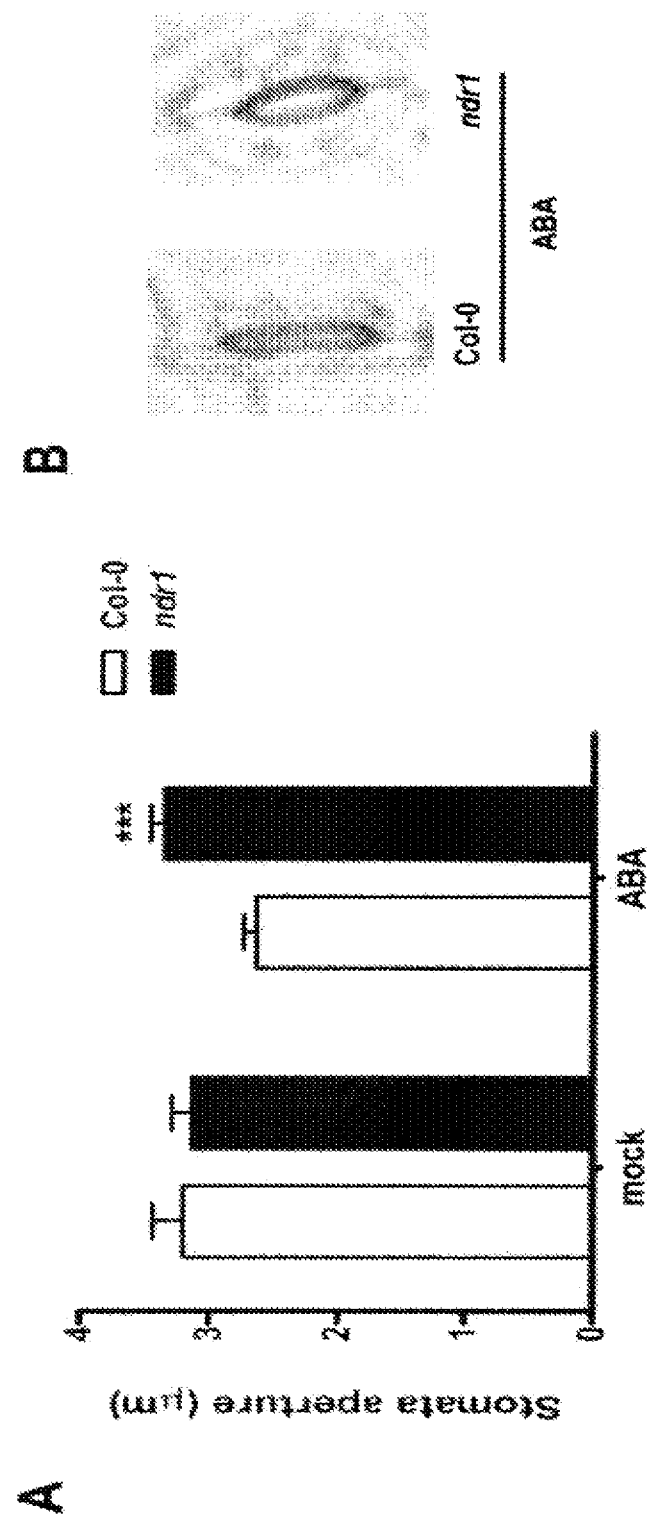

Stomata serve an important function in response to water stress, in large part by regulating transpiration rates. As an integral part of water stress, the regulation of stomatal aperture is a mechanism through which ABA-mediated signaling drives the conformational change in the shape of the guard cells, leading to a decrease in aperture size. To determine its putative role in linking ABA and stomata response, the NDR1 function was assayed. Epidermal peels of WT Col-0 and the ndr1 mutant were treated with 10 μM ABA, and after 1 hour, the stomata apertures were measured. As shown in FIGS. 12A and 12B, at 1 h following ABA treatment, WT Col-0 stomata exhibited a significant reduction in aperture (P<0.0001), while ndr1 stomata did not show a change in aperture following ABA treatment as compared to the mock treated control.

Although specific embodiments have been illustrated and described herein, it will be appreciated by those of ordinary skill in the art that any procedure that is calculated to achieve the same purpose may be substituted for the specific embodiments shown. For example, although the method has been discussed using an NDR1 from a particular plant or a particular regulatory element other plant species or regulatory elements, may be used. This application is intended to cover any adaptations or variations of the present subject matter. Therefore, it is manifestly intended that embodiments of this invention be limited only by the claims and the equivalents thereof.

What is claimed is:

1. A method of producing a plant having drought tolerance comprising:
    a) introducing into at least one plant or plant part a vector comprising a nucleic acid molecule which expresses or increases expression of a polypeptide that confers drought tolerance, wherein the nucleic acid molecule comprises nucleic acid sequences selected from:
        i) a nucleotide sequence of SEQ ID NO: 2 or functional variants thereof;
        ii) a nucleotide sequence that encodes a polypeptide comprising the amino acid sequence of SEQ ID NO: 1;
        iii) a nucleotide sequence encoding a NON-RACE-SPECIFIC DISEASE RESISTANCE1 (NDR1); and
        iv) a nucleotide sequence encoding variants of the amino acid sequence of SEQ ID NO:1 having at least 95% identity to the amino acid sequence of SEQ ID NO: 1 wherein the variants maintain the drought tolerance of SEQ ID NO:1;
    b) exposing the plants to drought stress conditions for greater than 6 days; and
    c) selecting at least one plant or plant part having improved drought tolerance from a plurality of plants or plant parts into which the vector has been introduced compared to a plant in which no vector has been introduced.

2. The method of claim 1, wherein the plant or plant part is a monocot or dicot.

3. The method of claim 1, wherein the plant or plant part is selected from corn, soybean, sunflower, sorghum, canola, wheat, alfalfa, cotton, rice, barley, tobacco, potato and sugar beet.

4. The method of claim 1, wherein the plant part is a plant cell.

5. The method of claim 1, wherein the vector comprises a regulatory element operably linked to the nucleic acid molecule encoding the polypeptide and wherein the regulatory element comprises an inducible promoter.

6. The method of claim 5, wherein the regulatory element comprises SEQ ID NO:3.

7. A plant or plant part having improved drought tolerance comprising a recombinant DNA construct comprising a polynucleotide operably linked to at least one regulatory element, wherein the at least one regulatory element comprises SEQ ID NO: 3 and wherein the polynucleotide comprises a nucleotide sequence selected from:
    i) a nucleotide sequence comprising SEQ ID NO: 2;
    ii) a nucleotide sequence encoding a polypeptide with drought tolerance activity,
    wherein the polypeptide has an amino acid sequence of at least 95% sequence identity to SEQ ID NO: 1; and
    wherein the plant or plant part exhibits improved drought tolerance under drought stress conditions for greater than 6 days when compared to a plant or plant part not comprising the recombinant DNA construct.

8. The plant or plant part of claim 7, wherein the plant is a monocot or dicot.

9. The plant or plant part of claim 7, wherein the plant is selected from corn, soybean, sunflower, sorghum, canola, wheat, alfalfa, cotton, rice, barley, tobacco, potato and sugar beet.

10. The plant or plant part of claim 7, wherein the at least one regulatory element is an NDR1 promoter.

11. The plant or plant part of claim 7, wherein the regulatory element is an inducible, developmentally-regulated, or tissue-preferred promoter.

12. The plant or plant part of claim 7, wherein the polynucleotide sequence is a synthetic sequence designed for expression in the plant.

13. The plant or plant part of claim 7, wherein the plant part is a plant cell or a seed.

* * * * *

UNITED STATES PATENT AND TRADEMARK OFFICE
CERTIFICATE OF CORRECTION

| | | |
|---|---|---|
| PATENT NO. | : 9,644,213 B2 | Page 1 of 15 |
| APPLICATION NO. | : 14/384094 | |
| DATED | : May 9, 2017 | |
| INVENTOR(S) | : Brad Day, Patricia Santos and Caleb Knepper | |

It is certified that error appears in the above-identified patent and that said Letters Patent is hereby corrected as shown below:

In the Drawings
Replace Drawing Sheets 1-13 with Replacement Drawing Sheets 1-13

In the Specification
Column 3/Line 11: Error reads as "in Co2-0 and" and should read as "in Col-0 and"
Column 3/Line 31: Error reads as "the NRD1" and should read as "the NDR1"
Column 17/Line 15: Error reads as "and paromycin" and should read as "and paromomycin"
Column 20/Line 66: Error reads as "expressing NRD1 may" and should read as "expressing NDR1 may"
Column 21/Line 1: Error reads as "of NRD1" and should read as "of NDR1"
Column 21/Line 46: Error reads as "(*Ipomoea batatus*)," and should read as "(*Ipomoea batatas*),"
Column 21/Line 47: Error reads as "(*Cofea* spp.)," and should read as "(*Coffea* spp.),"
Column 21/Lines 50-51: Error reads as "(*Ficus casica*)," and should read as "(*Ficus carica*),"
Column 21/Lines 63-64: Error reads as "(*Hibiscus rosasanensis*)," and should read as "(*Hibiscus rosasinensis*),"
Column 22/Line 2: Error reads as "(*Pinus elliotii*)," and should read as "(*Pinus elliottii*),"
Column 22/Line 3: Error reads as "(*Pinus contotta*)," and should read as "(*Pinus contorta*)"
Column 23/Line 33: Error reads as "detassling," and should read as "detasseling,"
Column 24/Line 15: Error reads as "RESISTANCE" and should read as "RESISTANCE1"
Column 24/Line 20: Error reads as "RESISTANCE" and should read as "RESISTANCE1"
Column 24/Line 25: Error reads as "RESISTANCE" and should read as "RESISTANCE1"
Column 26/Line 8: Error reads as "Table 51." and should read as "Table S1."
Column 26/Lines 44-45: Error reads as "Table 51." and should read as "Table S1."
Column 30/Line 56: Error reads as "in FIG. 2A" and should read as "in FIGS. 2A"
Column 31/Line 26: Error reads as "summarize the summarizing" and should read as "summarize the"
Column 33/Line 57: Error reads as "NRD1 is" and should read as "NDR1 is"

Signed and Sealed this
Eighteenth Day of July, 2017

Joseph Matal
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 9,644,213 B2

In the Claims

Column 41/Claim 1: Error reads as "NO: 1wherein" and should read as "NO: 1 wherein"

Column 42/Claim 7: Error reads as "NO: 3and" and should read as "NO: 3 and"

AGTTATCTTAACTTTCAAGATCGATACTAACCAATTGAATATTGTATTGT
TAACTGTGCAAAATATTTTAGTACGACTTTGCGAGTCAGTTTAGTCTGTT
AAAAATTATTTTGTTTGGGTCATAAAAACTATCTATATCTTTGCATGAAA
CAGCACTACAGTCTACATCAGATTTATAATTTAAAAAGACGCGGTAGTAT
TTTAAAACATTTTGTTTCGTTTATTCATTTATTGTGAAAGTTGACATCGA
TTACATCAAACAATAATCTTTTCTAGATCATTTTCCTAACGAATCTATTC
AGTGAACCATGTGACACAATTTACATTGGTTGGTAGTAATATAAGAATTT
CACATGTGGTATATTATAAATAATTTTAGTTTCACATAATTTTAATCAA
AGAAATTTAATTTGATATGTTTAATATTAATAATGTTAAAAATATAAAAT
AAATATTAAAGCTTAGAGTTAATAATATTTTAAAC:TTTTACTATAGTTG
ACACTTTTAAAAATCTAATATAAACTATACCTGGTAAAACTAAATAGTTT
AACTAAAAAATGAATCAAACAATATAAGAGATATTCAAAGCAGTTTAACA
ATATCTAGTCTTAGATTTACTCATGCGGATTCCAGAATAATTTGGATACT
AGTTCTCTGTTTCAGTTCAGAGTTATTGCATTTTCATAAATAAAGCGAAT
ATGAATTTAGTTTTATCAATCTAGTAGATTTTCAGTTTTTATTTATCAA
ACAATTATTTCAGTTTCTTTTTTCAGGTTTTATCAATCTAGTAGATTTTC
AGTTTTTTGTTTATCAAACAATTATTTCAGTTTCTTTTTTCAGTTTATGT
TCGATAACAATGTTTTAGATATACGATAATCAAGTAGTTCGAATTACCTT
GACATTTCTAGATTGAATTTTCCAAACAAAGTTTACATATATATATATAT
ATATATATATAGCGGATTGCTCATTGCCATTGGTTGTGAAATCAAGAATT
AATGTGGATGGTAAGATGTAAACTTCTTACAAAAAGTCTATTTAGGAGAA
CGAAAACGTGTGAAGGTCTTGTTTTCCTAAGGTTTCGTTTGGGTCTCTT
TTATTTTGTACCTTGTAATTCTCTTGGCCCTTTAGCCAACTAAGCACATT
TTGGGATTGAATATATATTTAAAAAAATATATATATATATATATATATTA
AGAAAATTACTTTTGAAATTTGTATTTTGATTAGTGTTGCTAATTATGGT
TTAAGCATGAGAGTCCATCCAATTCGACCCGAGTCCTATATACAGTATGG
TTCAGCAAAAGGGTTTGGGCCTGGCCATAGTTTTTTATGGCAACAAGCTA
TATGAAACCATATATAATAAATA*CAAT*TTCGTATTTTGATACAGTCAGTA
TGAGACTAGAAAAACTAGCCACTAGGCCACTGACCAAAAAATAAAATAAG
AAAAAAACTAATCTTTATCTCACCATATTTTAGATCTTTGAAATTCCAA
AAACATAATTAGAGTTTCTCTTTCCTTAGTTTCTTGTGTAGTTTGTATGT
TTCAGTAGGGTTTTTTTCCTTATTTTATGTAAATAAATGGAATAAGATTC
AGTTTTCTGTTATGGGACATCCCTCGTTAATTCTTGTTTTGGTTCTTTTT
GATAACCCAAAGTTTATATAGGTTTTTTTTAATTTATCTTCTTACGTCC
ATTAATTTGTTTTTGTTTTGTTATGTATTTGGCTAAACGCGTGTGTGCGT
GTGTGTCCTACTGAGTCGTCTCTTTGAGTCAACTTGAAATATCAACCAA
TCAGCAAACCAAAATCTTATAACATCATCTTCTTCATCTTTCCGACAAAA
ATACCAAATTCTTGAAAACAAAAAAAAAATG
                              +1

Figure 9